(12) United States Patent
Kriesel

(10) Patent No.: US 8,231,575 B2
(45) Date of Patent: Jul. 31, 2012

(54) FLUID DELIVERY DEVICE

(75) Inventor: Marshall S. Kriesel, St. Paul, MN (US)

(73) Assignee: BioQuiddity, Inc., San Francisco, CA (US)

(*) Notice: Subject to any disclaimer, the term of this patent is extended or adjusted under 35 U.S.C. 154(b) by 214 days.

(21) Appl. No.: 12/456,153

(22) Filed: Jun. 12, 2009

(65) Prior Publication Data

US 2009/0254067 A1     Oct. 8, 2009

Related U.S. Application Data

(62) Division of application No. 10/855,436, filed on May 26, 2004, now abandoned.

(51) Int. Cl.
*A61M 37/00* (2006.01)

(52) U.S. Cl. .................. 604/133; 604/131; 604/132

(58) Field of Classification Search .......... 604/131–133, 604/246, 82, 83
See application file for complete search history.

(56) References Cited

U.S. PATENT DOCUMENTS

| | | | | |
|---|---|---|---|---|
| 5,336,188 A | * | 8/1994 | Kriesel ..................... | 604/132 |
| 2001/0007932 A1 | * | 7/2001 | Kamen et al. .............. | 604/132 |

* cited by examiner

*Primary Examiner* — Laura Bouchelle
(74) *Attorney, Agent, or Firm* — James E. Brunton

(57) ABSTRACT

A compact fluid dispenser for use in controllably dispensing fluid medicaments, such as antibiotics, oncolytics, hormones, steroids, blood clotting agents, analgesics, and like medicinal agents from prefilled containers at a uniform rate. The dispenser uniquely includes a stored energy source that is provided in the form of a compressible-expandable elastomeric member of novel construction that provides the force necessary to continuously and uniformly expel fluid from the device reservoir. The device further includes a fluid flow control assembly that precisely controls the flow of the medicament solution to the patient.

14 Claims, 48 Drawing Sheets

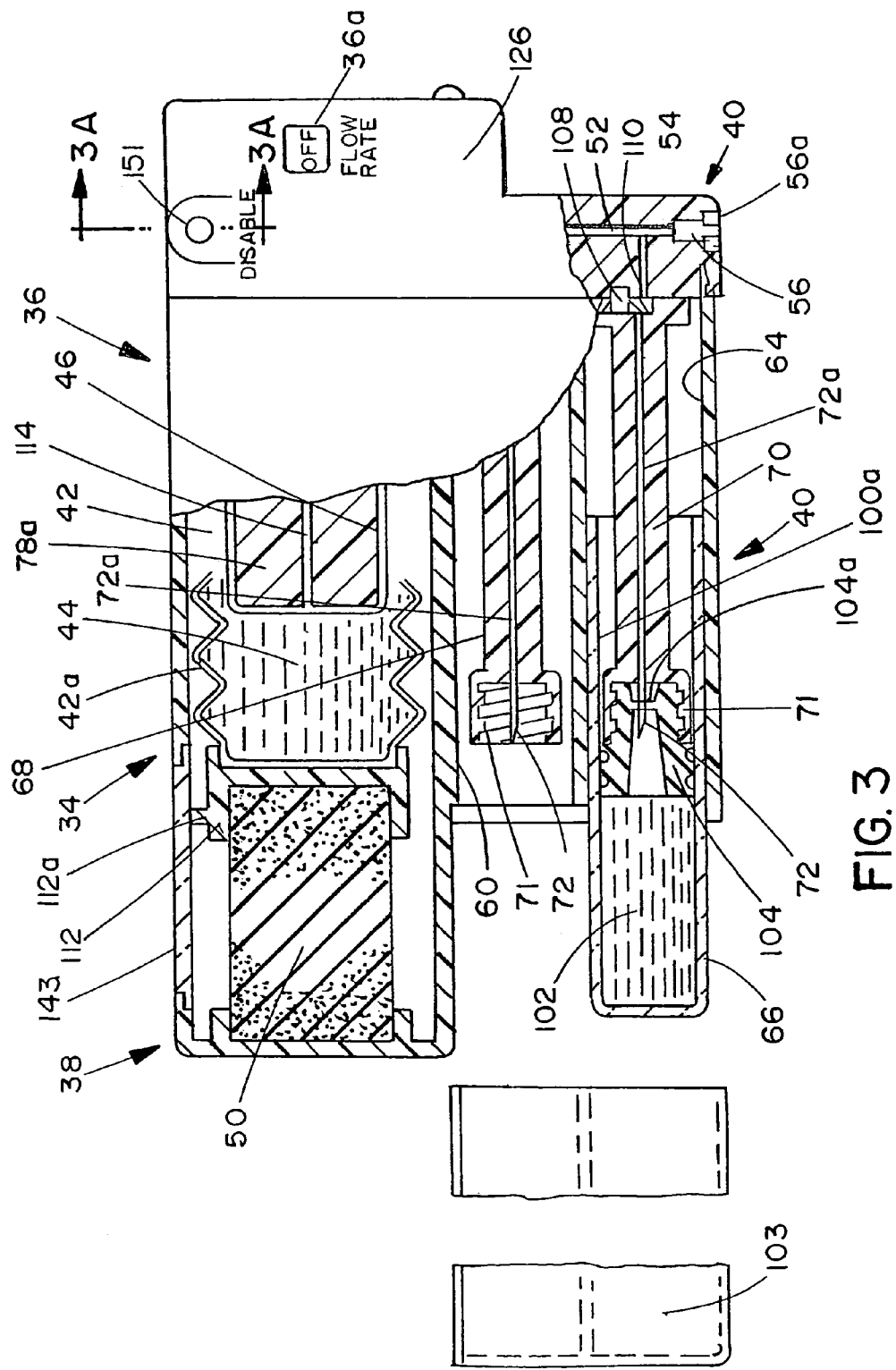

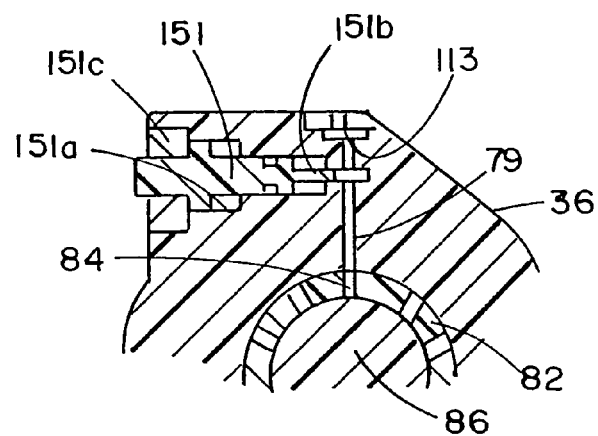
FIG. 3A
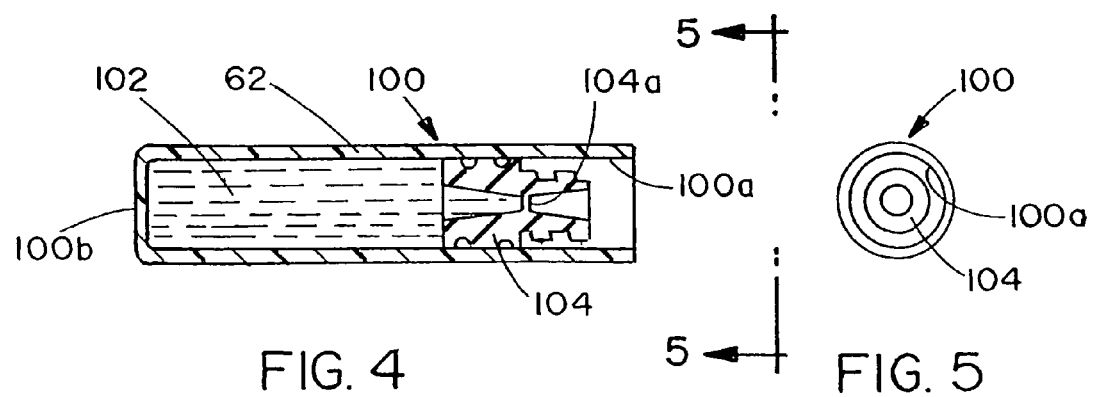
FIG. 4
FIG. 5

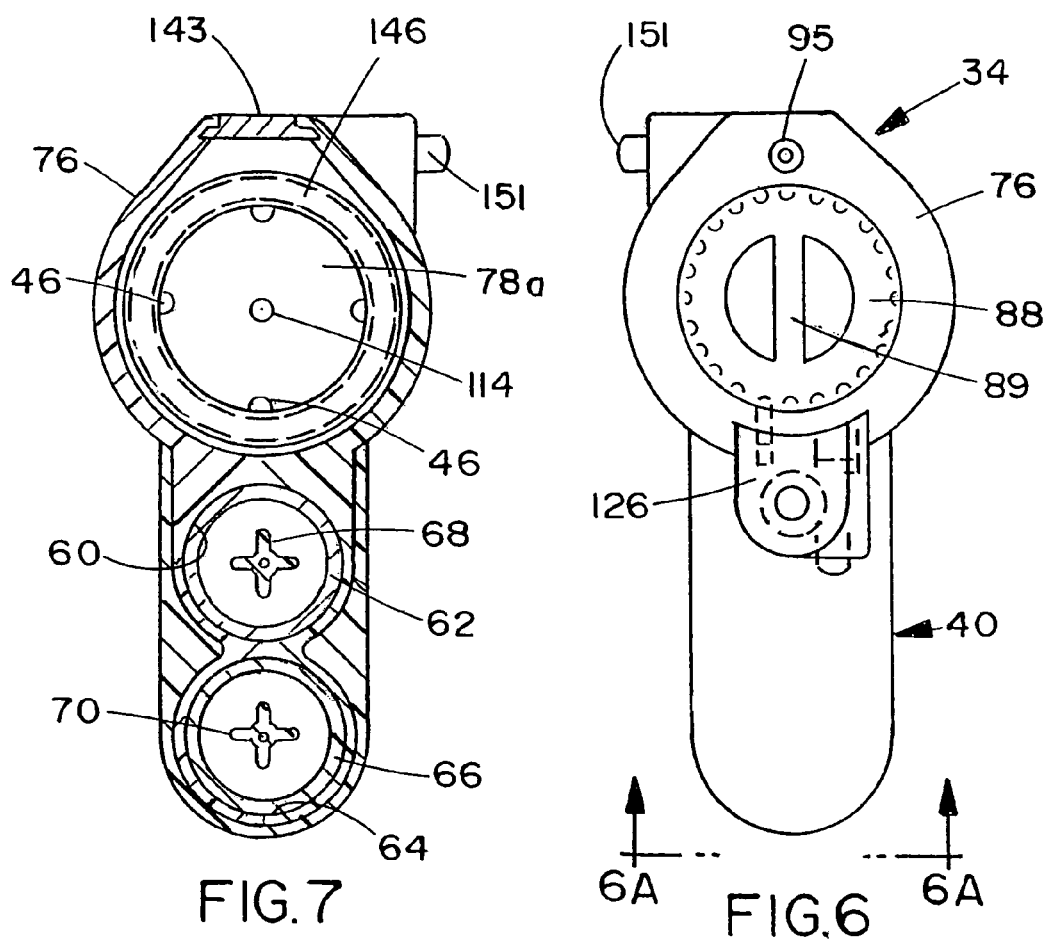
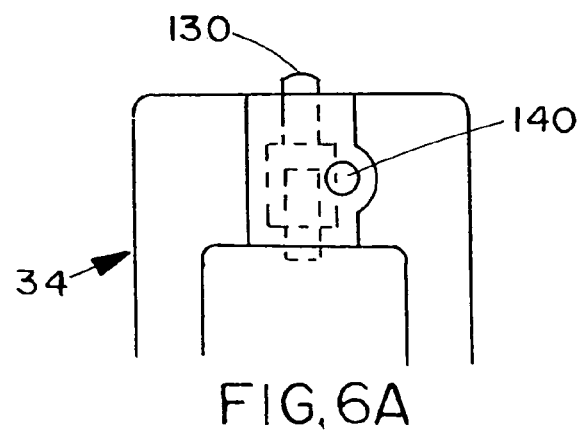

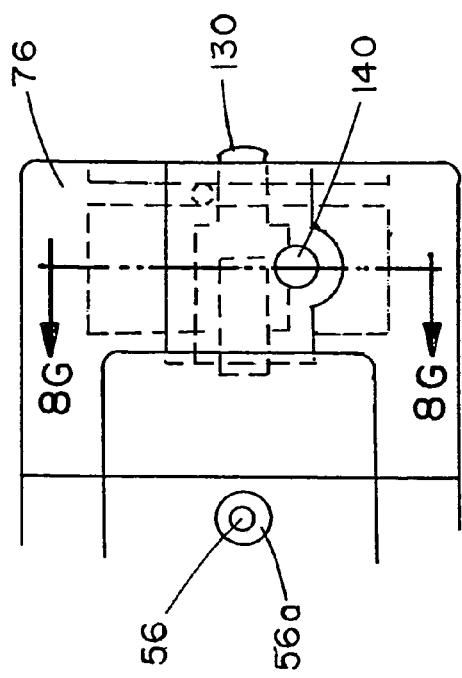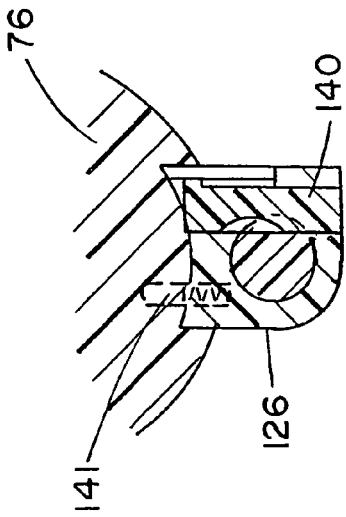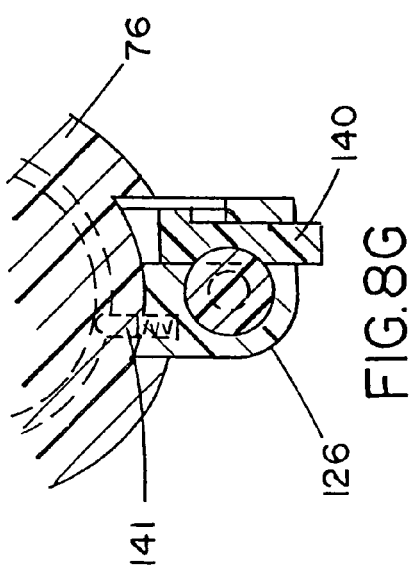

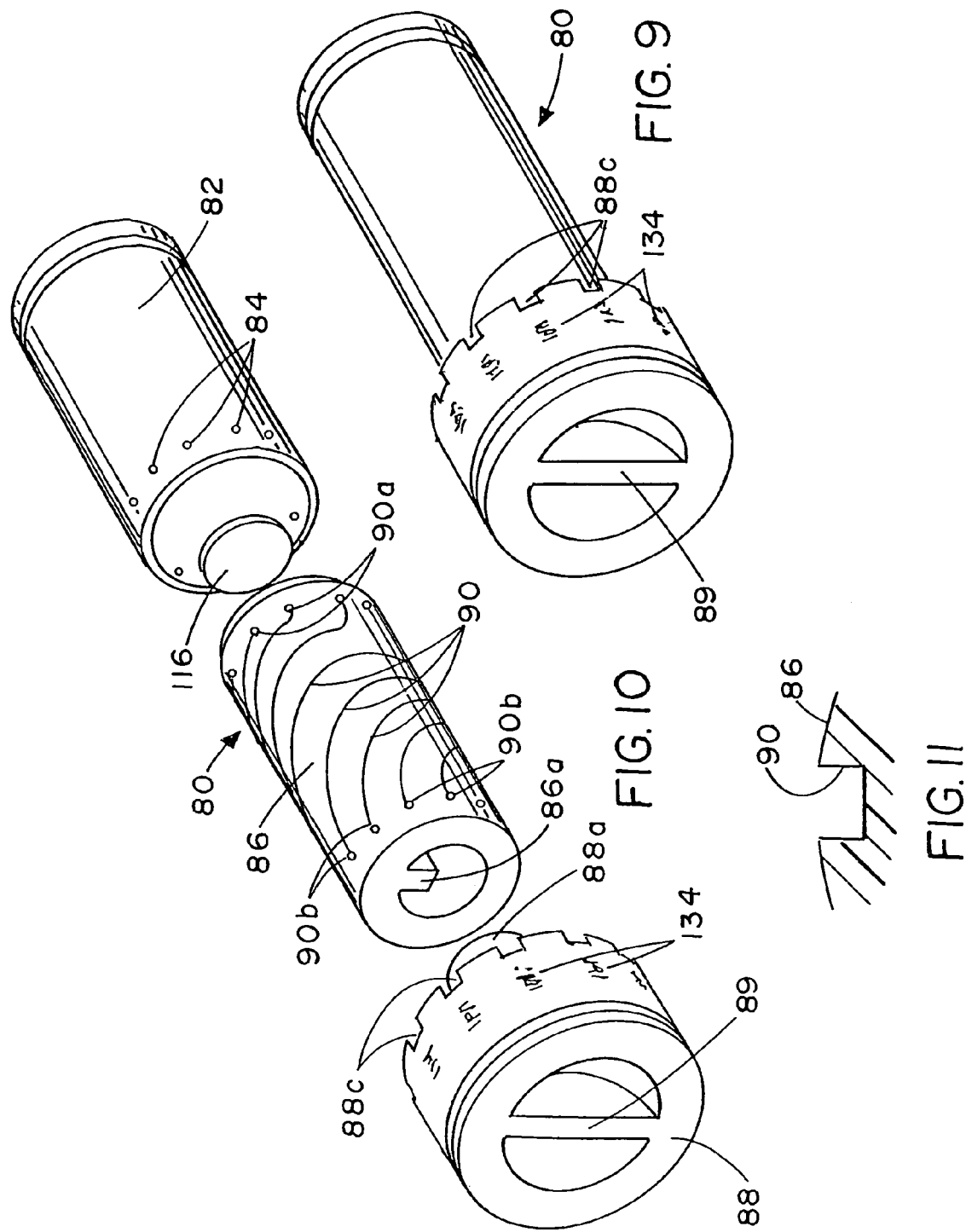

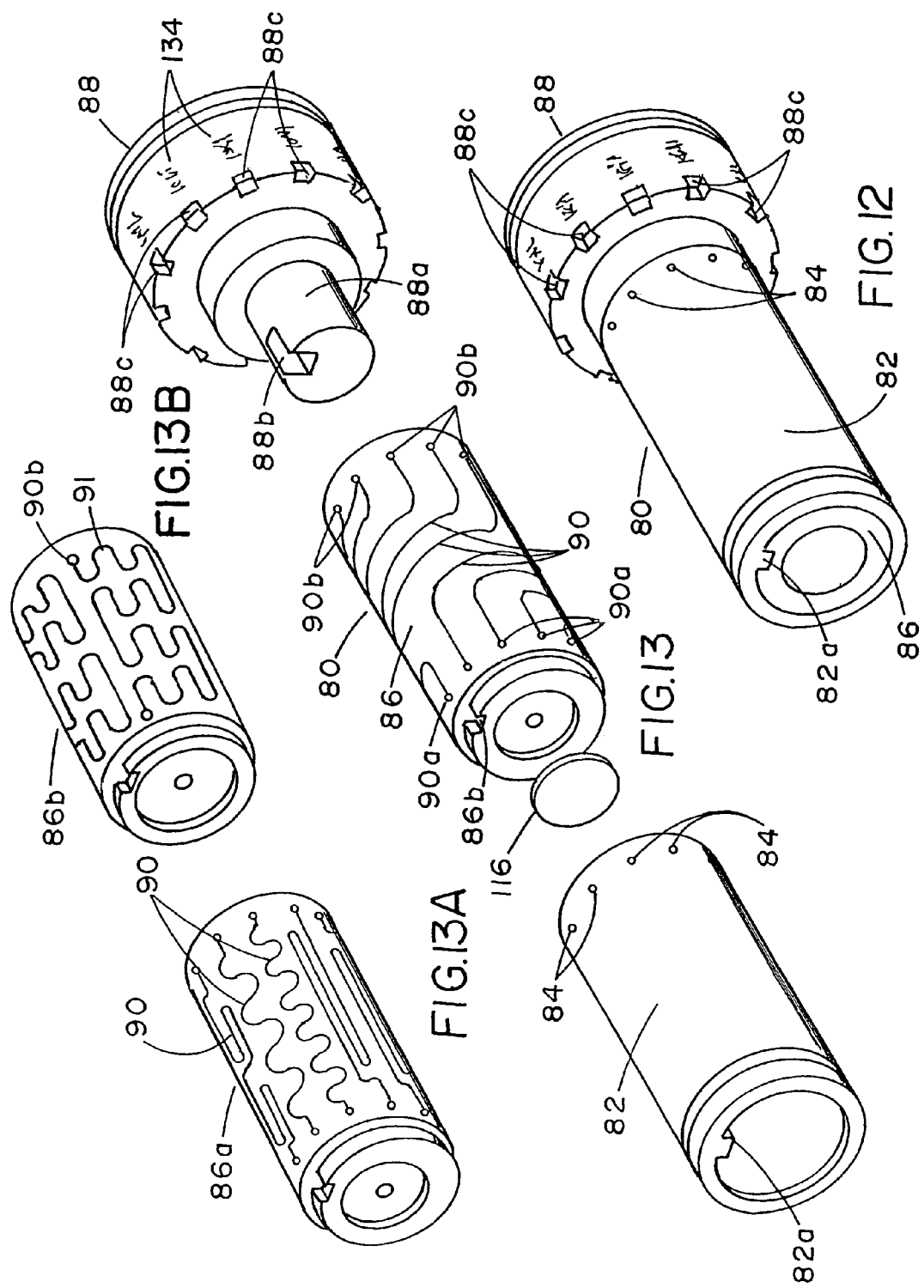

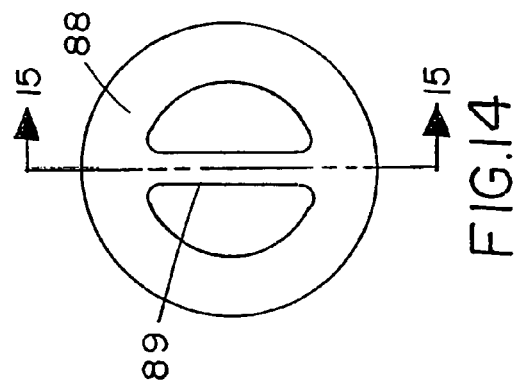
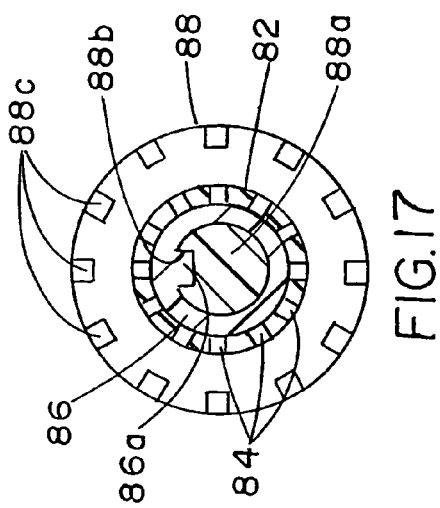
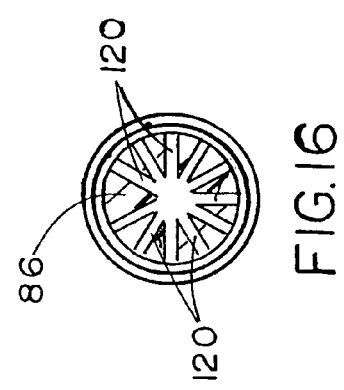
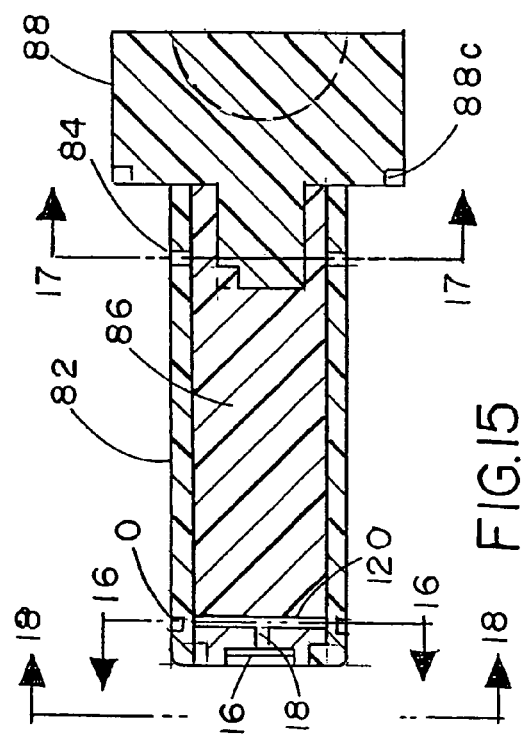
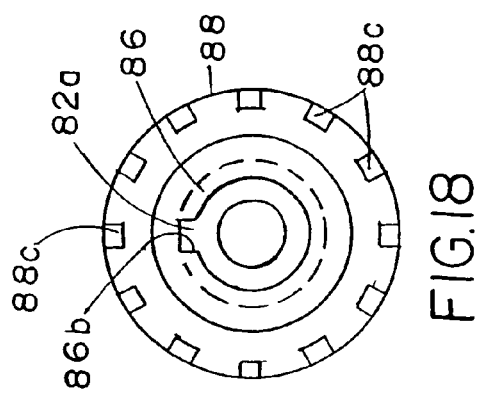

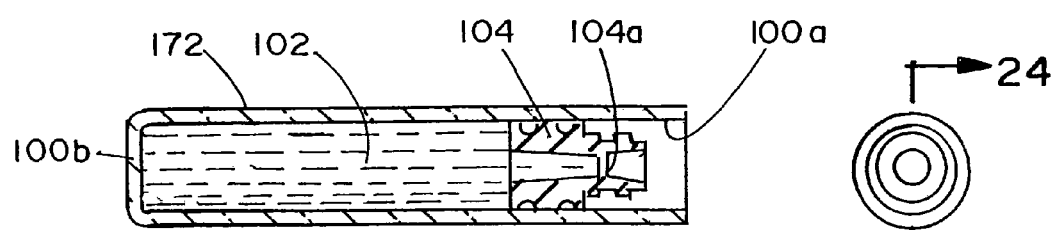
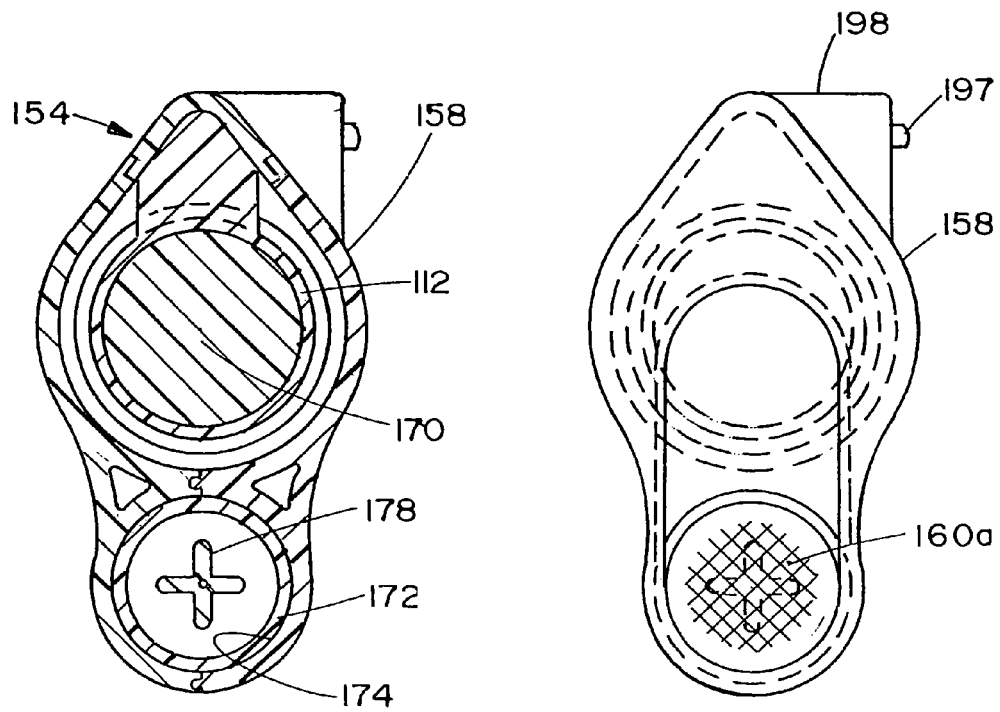

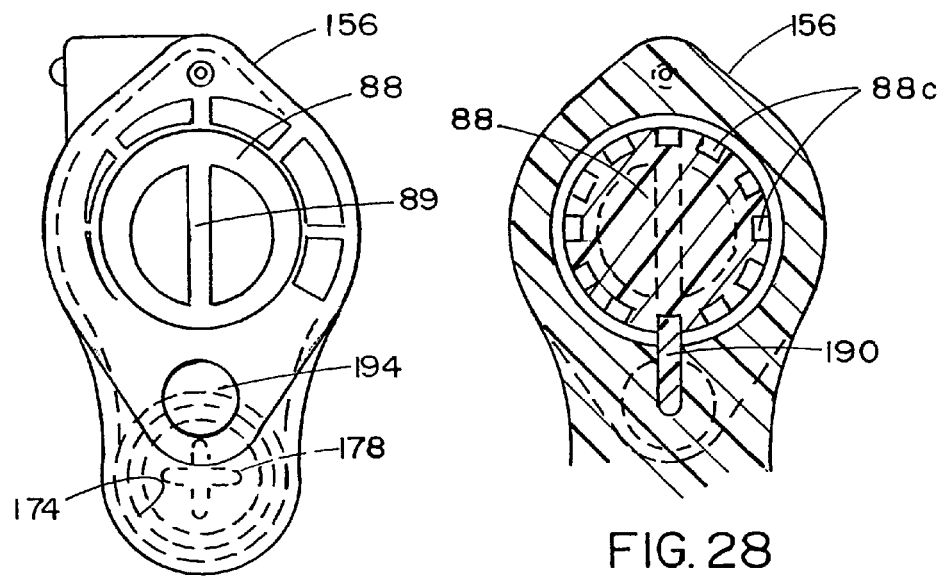
FIG. 27
FIG. 28
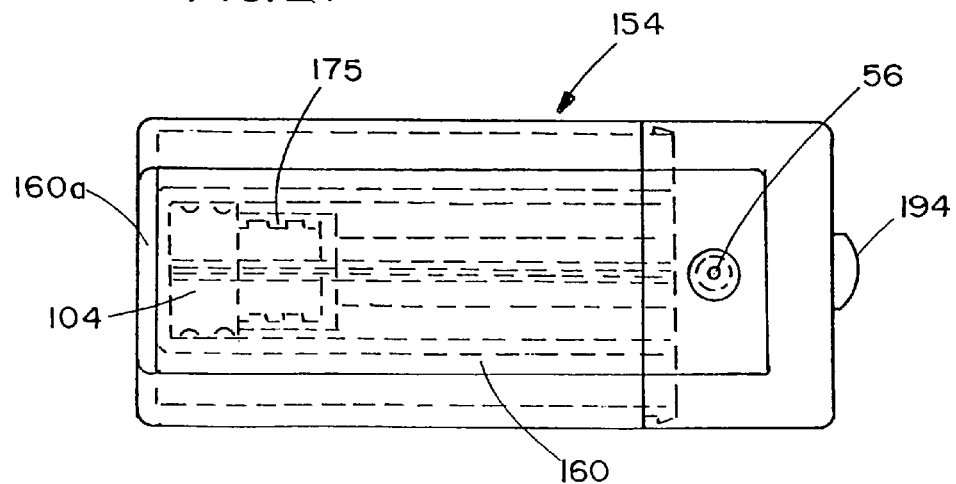
FIG. 29

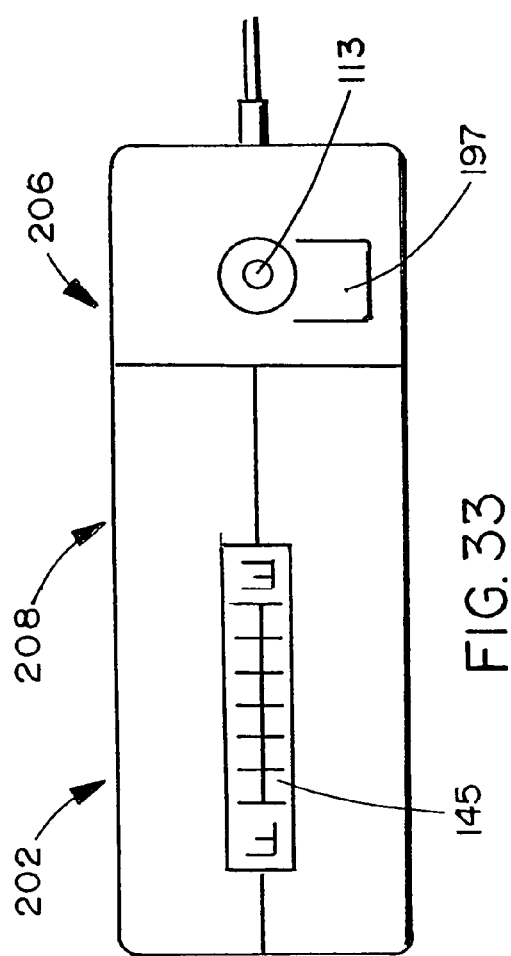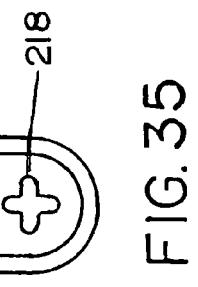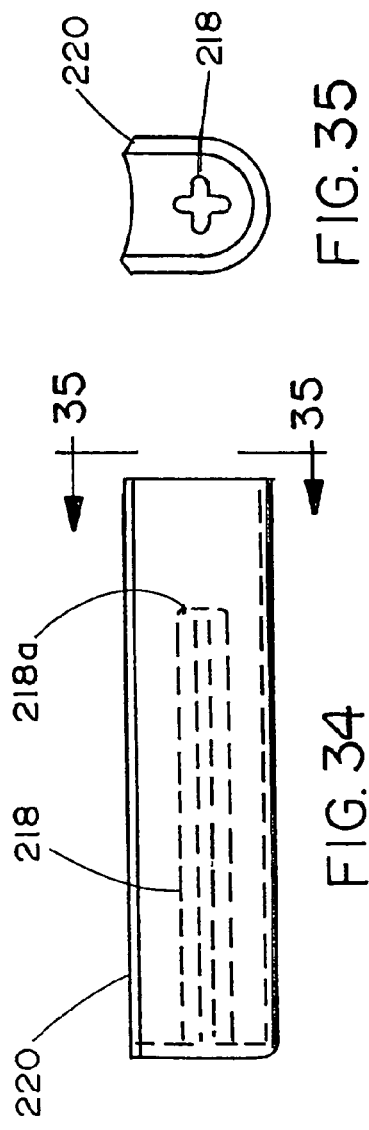

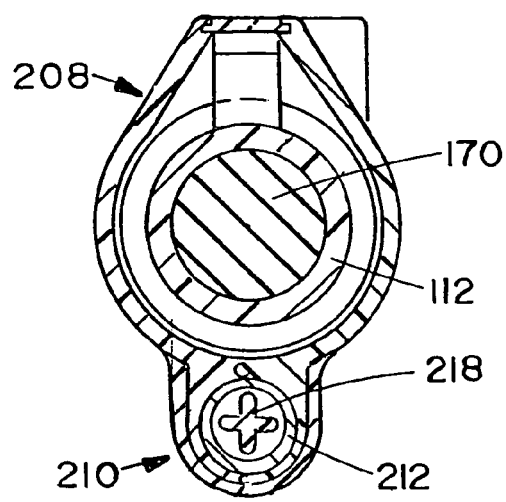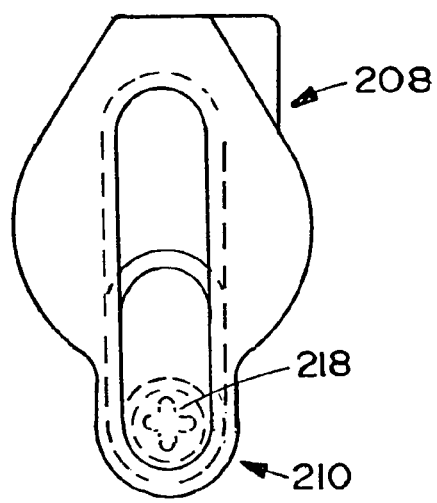
FIG. 39  FIG. 40
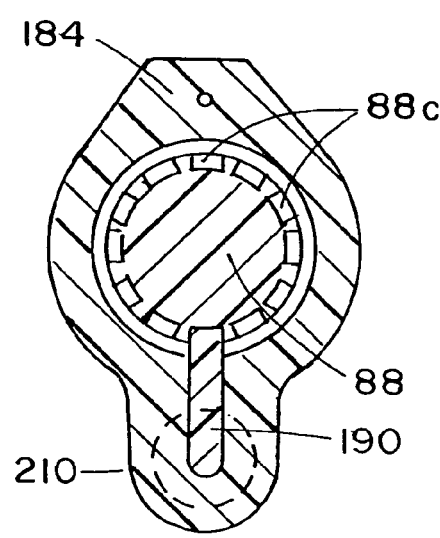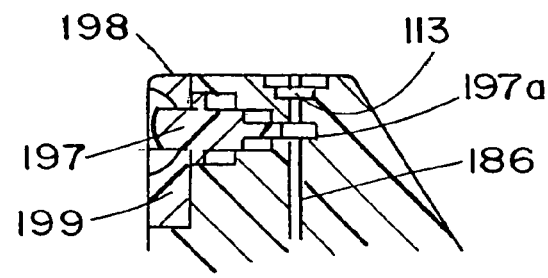
FIG. 41  FIG. 42

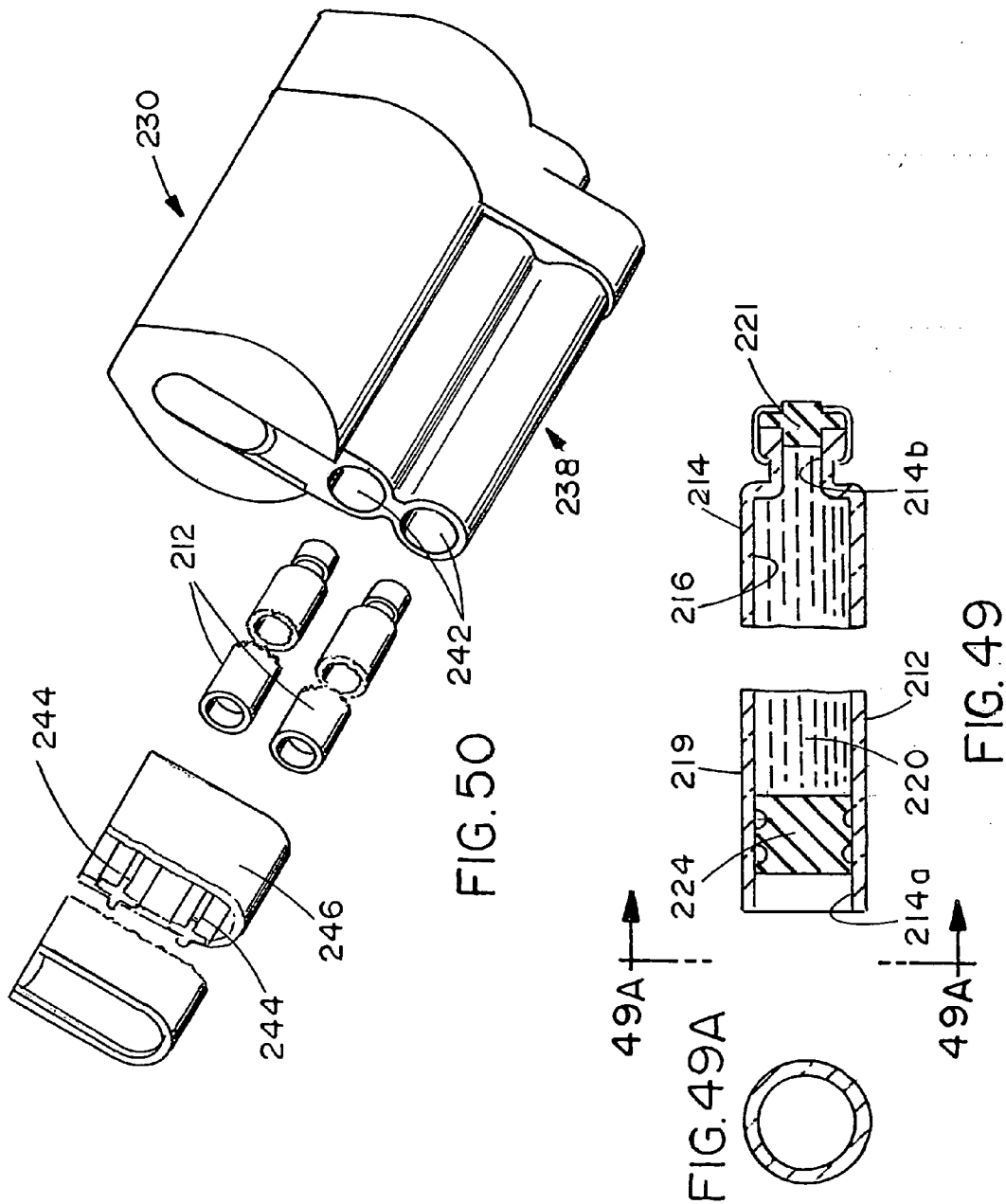

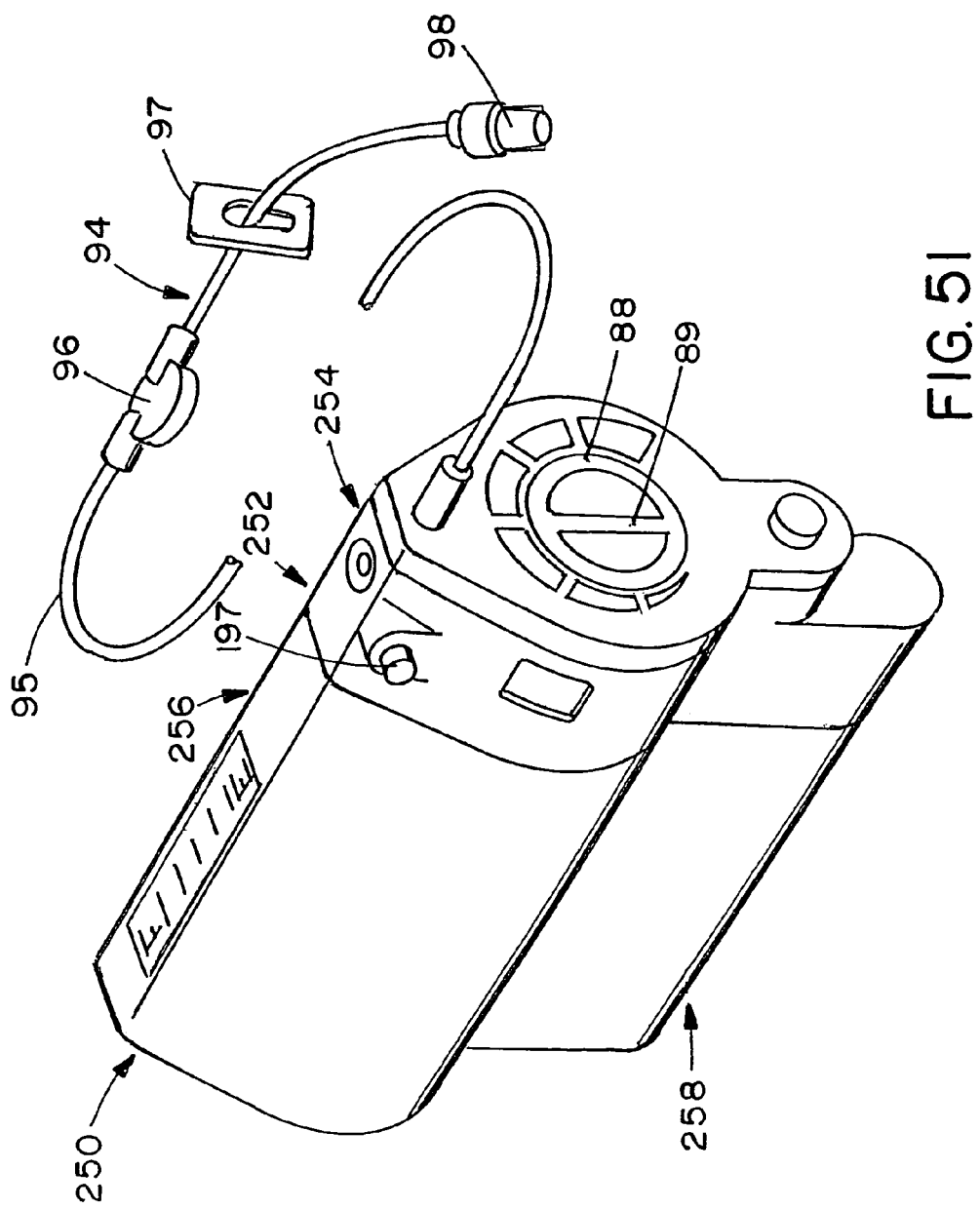

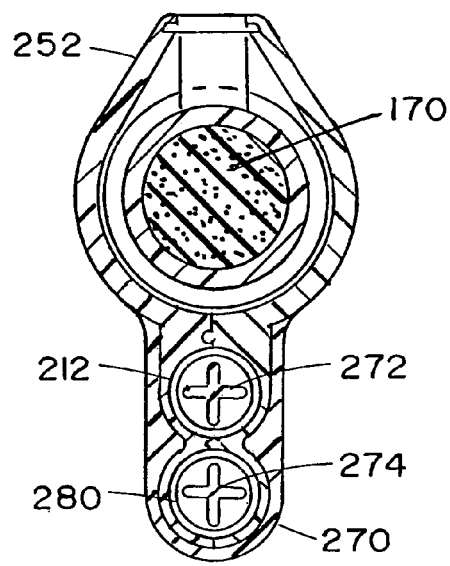
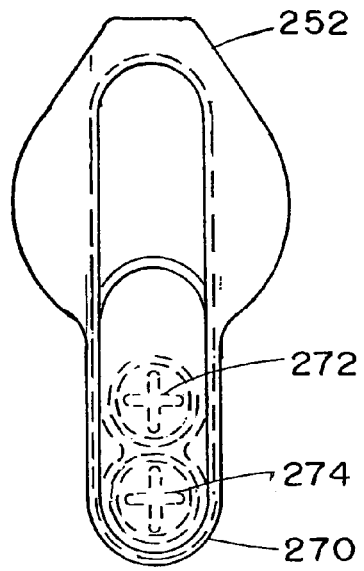
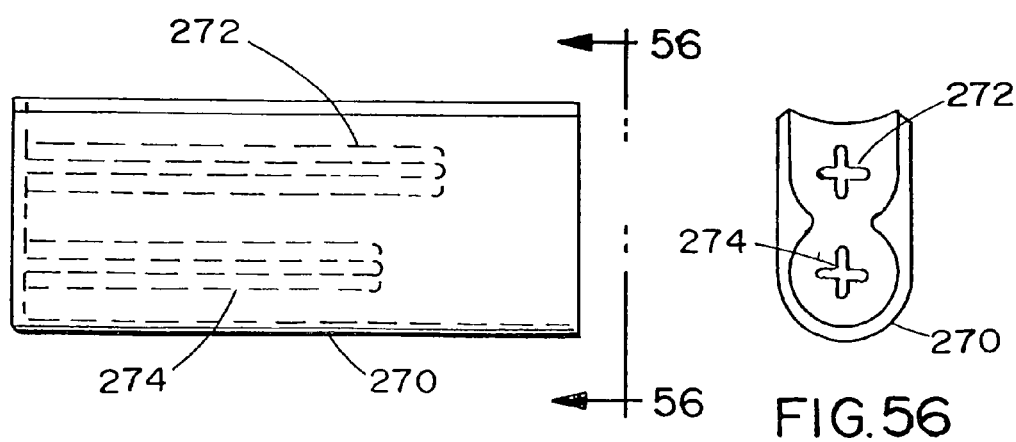

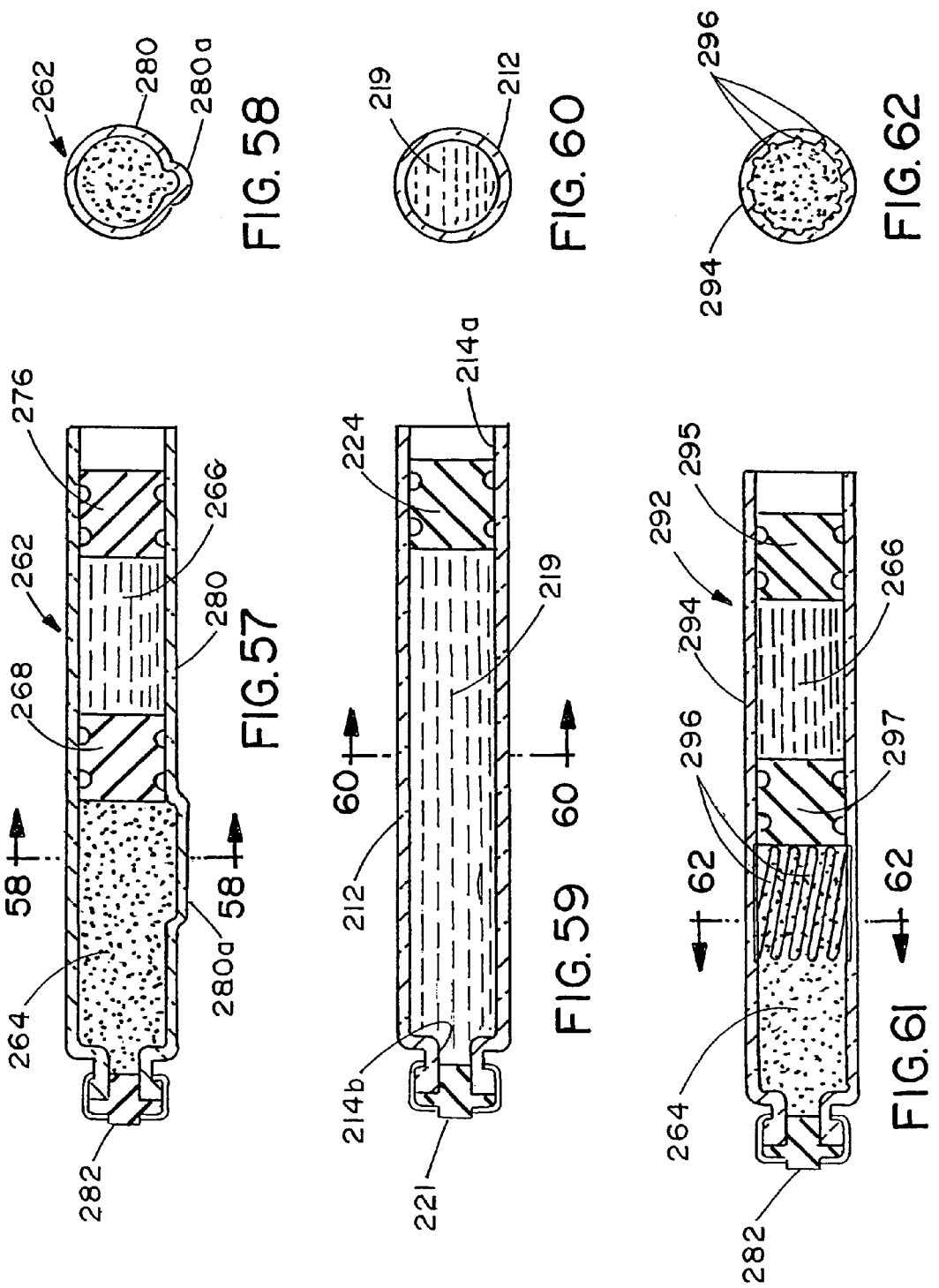

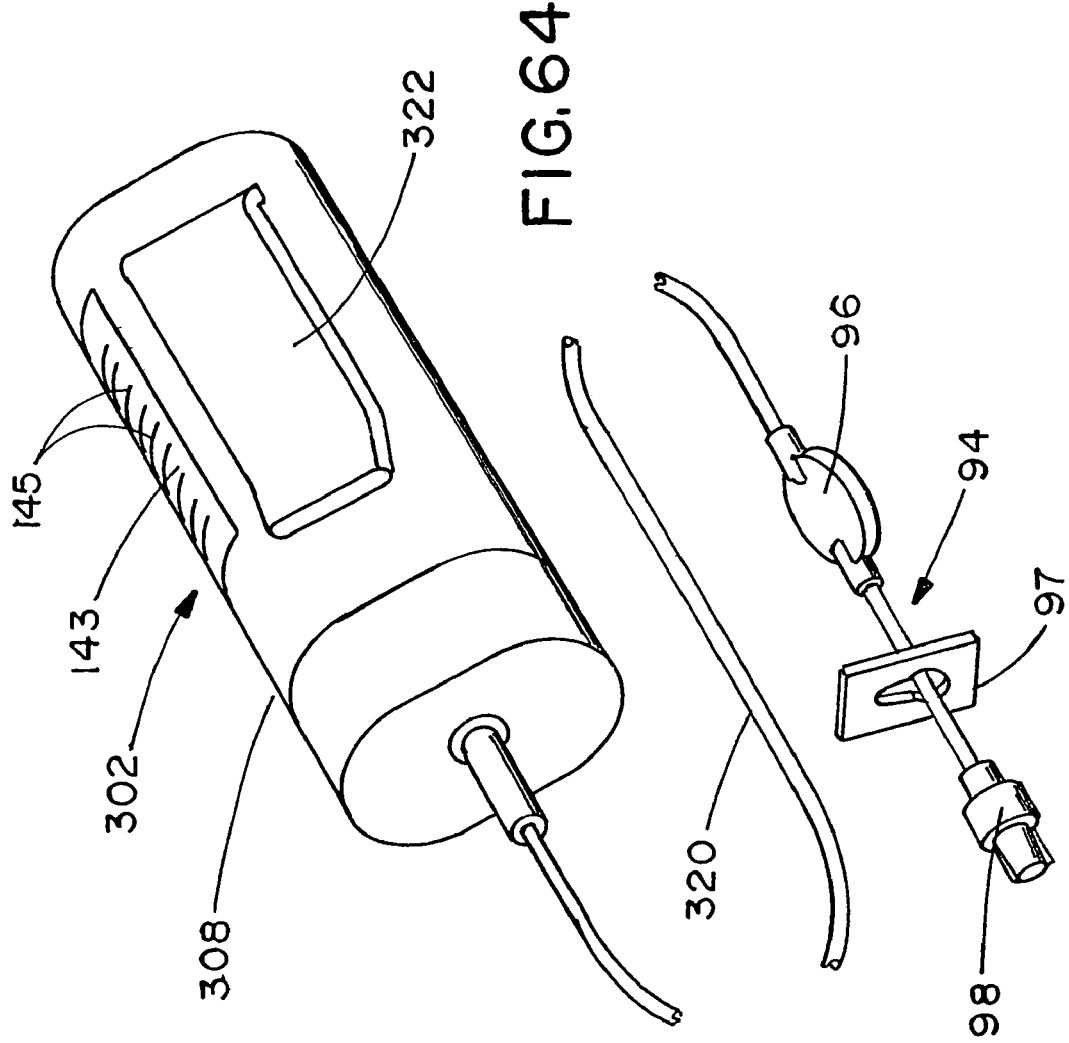

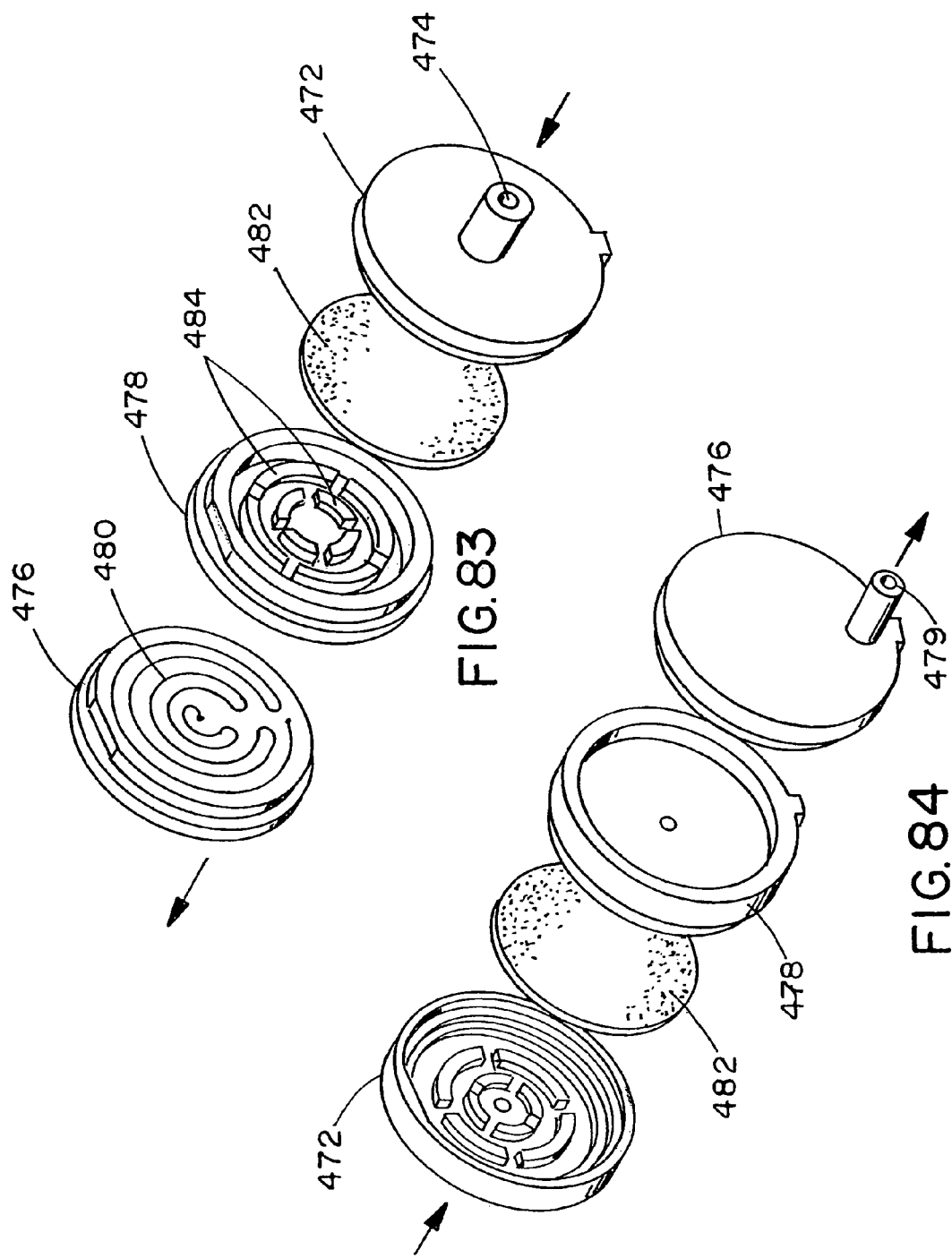

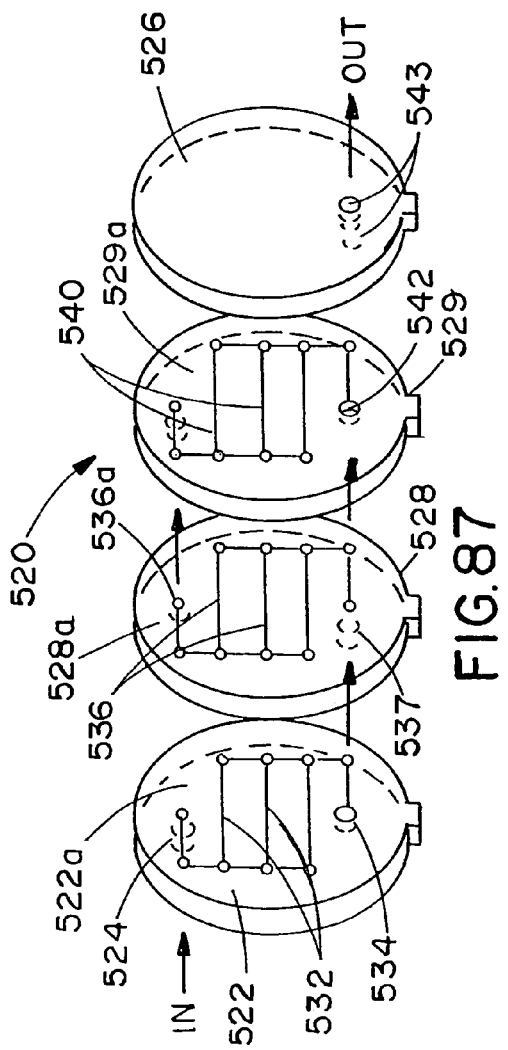
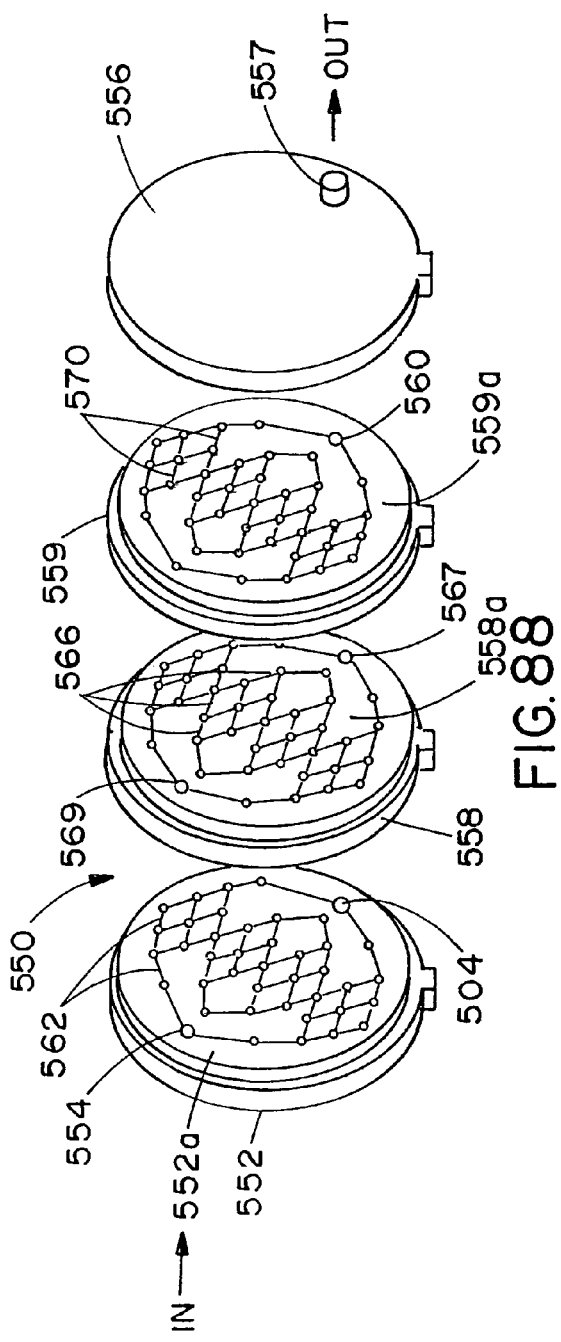
FIG. 87
FIG. 88

FLUID DELIVERY DEVICE

CROSS-REFERENCE TO RELATED APPLICATIONS

This is a Divisional application of U.S. Ser. No. 10/855,436 filed May 26, 2004 now abandoned.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time, which apparatus includes a novel energy source, a novel fill means for filling the reservoir of the apparatus and a unique, adjustable, multichannel flow rate control means for precisely adjustably controlling the rate of fluid flow from the reservoir of the device.

2. Description of Related Art Including Information Disclosed Under 37 CFR 1.97 and 1.98

A number of different types of medicament dispensers for dispensing medicaments to ambulatory patients have been suggested. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravimetric methods are cumbersome, imprecise and require bed confinement of the patient. Periodic monitoring of the apparatus by the nurse or doctor is required to detect malfunctions of the infusion apparatus.

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose can result in a toxic reaction.

For those patients that require frequent injections of the same or different amounts of medicament, the use of the hypodermic syringe method of delivery is common. However for each injection, it is necessary to first draw the injection dose into the syringe, then check the dose and, after making certain that all air has been expelled from the syringe, finally, inject the dose either under bolus or slow push protocol. This cumbersome and tedious procedure creates an unacceptable probability of debilitating complications, particularly for the elderly and the infirm.

As will be appreciated from the discussion which follows, the apparatus of the present invention is uniquely suited to provide precise fluid delivery management at a low cost in those cases where a variety of precise dosage schemes are of utmost importance. An important aspect of the apparatus of the present invention is the provision of novel fill means for filling the reservoir of the device using a conventional medicament vials or cartridge containers of various types having a pierceable septum. Another unique feature of the apparatus of the present invention is an embedded microcapillary multichannel flow rate control means which enables precise control of the rate of fluid flow of the medicament to the patient. More particularly, the apparatus of the present invention includes a unique, adjustable fluid flow rate mechanism which enables the fluid contained within the reservoir of the device to be precisely dispensed at various selected rates.

The apparatus of the present invention can be used with minimal professional assistance in an alternate health care environment, such as the home. By way of example, devices of the invention can be comfortably and conveniently removably affixed to the patient's body or clothing and can be used for the continuous infusion of injectable anti-infectives, hormones, steroids, blood clotting agents, analgesics, and like medicinal agents. Similarly, the devices of the invention can be used for most I-V chemotherapy and can accurately deliver fluids to the patient in precisely the correct quantities and at extended microfusion rates over time.

By way of summary, the apparatus of the present invention uniquely overcomes the drawbacks of the prior art by providing a novel, disposable dispenser of simple but highly reliable construction. A particularly important aspect of the apparatus of the present invention resides in the provision of a novel, self-contained energy source in the form of a substantially constant-force compressible-expandable elastomeric member that provides the force necessary to uniformly and precisely dispense various solutions from standard prefilled vial containers that can be conveniently loaded into the apparatus. Because of the simplicity of construction of the apparatus of the invention and the straightforward nature of the energy source, the apparatus can be manufactured at low cost without in any way sacrificing accuracy and reliability.

With regard to the prior art, one of the most versatile and unique fluid delivery apparatus developed in recent years is that developed by the present inventor and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to the present applicant, namely U.S. Pat. No. 5,743,879, discloses an injectable medicament dispenser for use in controllably dispensing fluid medicaments from a prefilled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a prefilled container which is housed within the body of the device. After having been deformed, the polymeric, elastomeric member will return to its starting configuration in a highly predictable manner.

Another important prior art fluid delivery device is described in U.S. Pat. No. 6,063,059 also issued to the present inventor. This device, while being of a completely different construction, embodies a compressible-expandable stored energy source somewhat similar to that used in the apparatus of the present invention.

Still another prior art fluid delivery device, in which the present inventor is also named as an inventor, is described in U.S. Pat. No. 6,086,561. This latter patent incorporates a fill system that makes use of conventional vials and cartridge medicament containers.

BRIEF SUMMARY OF THE INVENTION

It is an object of the present invention to provide a compact fluid dispenser for use in controllably dispensing fluid medicaments such as, antibiotics, oncolytics, hormones, steroids, blood clotting agents, analgesics, and like medicinal agents from prefilled containers at a uniform rate.

Another object of the invention is to provide a small, compact fluid dispenser that includes a housing to which fill vials can be connected for filling the dispenser reservoir with the injectable fluid.

Another object of the invention is to provide a dispenser in which a stored energy source is provided in the form of a substantially constant-force, compressible-expandable elastomeric member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser which is adapted to be used with conventional prefilled drug containers to deliver beneficial agents therefrom in a precise and sterile manner.

Another object of the invention is to provide a fluid dispenser of the class described which is compact, lightweight, is easy for ambulatory patients to use, is fully disposable, and is extremely accurate so as to enable the infusion of precise doses of medicament over prescribed periods of time.

Another object of the invention is to provide a device of the character described which embodies a novel fluid volume indicator that provides a readily discernible visual indication of the volume of fluid remaining in the device reservoir Another object of the invention is to provide a point of care, self-contained medicament dispenser which is of very simple construction and can be filled at will at time of use.

Another object of the invention is to provide a fluid dispenser as described in the preceding paragraphs which is easy and inexpensive to manufacture in large quantities.

BRIEF DESCRIPTION OF SEVERAL VIEWS OF THE DRAWINGS

FIG. 3 is a cross-sectional view similar to FIG. 2, but showing the apparatus in a fluid fill mode.

FIG. 3A is a cross-sectional view taken along lines 3A-3A of FIG. 3.

FIG. 4 is a cross-sectional view of one of the prefilled medicament shell vials that can be used to fill the fluid reservoir of the apparatus.

FIG. 5 is a view taken along lines 5-5 of FIG. 4.

FIG. 6 is a view taken along lines 6-6 of FIG. 2B.

FIG. 6A is a view taken along lines 6A-6A of FIG. 6.

FIG. 7 is a cross-sectional view taken along lines 7-7 of FIG. 2A.

FIG. 8F is an enlarged, fragmentary, bottom view of the forward portion of the apparatus shown in FIG. 3.

FIG. 8G is a cross-sectional view taken along lines 8G-8G of FIG. 8F.

FIG. 8H is a fragmentary cross-sectional view similar to FIG. 8G but showing the indexing means in a locked position.

FIG. 9 is a generally perspective front view of one form of the fluid flow control assembly of the apparatus of the invention.

FIG. 10 is a generally perspective exploded front view of the fluid flow control assembly shown in FIG. 9.

FIG. 11 is a fragmentary cross-sectional view of one of the flow control channels formed in the flow control member shown in the central portion of FIG. 10.

FIG. 12 is a generally perspective rear view of the fluid flow control assembly of the apparatus of the invention shown in FIG. 9.

FIG. 13 is a generally perspective exploded rear view of the fluid flow control assembly shown in FIG. 10.

FIG. 13A is a generally perspective view of an alternate form of the flow control member of the invention.

FIG. 13B is a generally perspective view of yet another form of the flow control member of the invention.

FIG. 14 is a front view of the assembly shown in FIG. 9.

FIG. 15 is a cross-sectional view taken along lines 15-15 of FIG. 14.

FIG. 16 is a cross-sectional view taken along lines 16-16 of FIG. 15.

FIG. 17 is a cross-sectional view taken along lines 17-17 of FIG. 15.

FIG. 18 is a view taken along lines 18-18 of FIG. 15.

FIG. 23 is an end view of one of the prefilled medicament shell vials that can be used to fill the fluid reservoir of the apparatus.

FIG. 24 is a view taken along lines 24-24 of FIG. 23.

FIG. 25 is cross-sectional view taken along lines 25-25 of FIG. 22.

FIG. 26 is a view taken along lines 26-26 of FIG. 22.

FIG. 27 is a view taken along lines 27-27 of FIG. 22.

FIG. 28 is a cross-sectional view taken along lines 28-28 of FIG. 22.

FIG. 29 is a bottom view of the apparatus shown in FIG. 19.

FIG. 33 is a top plan view of the alternate form of the invention shown in FIG. 32.

FIG. 34 is a side elevational view of the fill vial cover assembly of the alternate form of the invention shown in FIG. 32.

FIG. 35 is a view taken along lines 35-35 of FIG. 34.

FIG. 39 is a cross-sectional view taken along lines 39-39 of FIG. 37.

FIG. 40 is a view taken along lines 40-40 of FIG. 37.

FIG. 41 is a cross-sectional view taken along lines 41-41 of FIG. 37.

FIG. 42 is a cross-sectional view taken along lines 42-42 of FIG. 37.

FIG. 49 is an enlarged view of one of the fill vial assemblies shown in FIG. 44.

FIG. 49A is a view taken along lines 49A-49A of FIG. 49.

FIG. 50 is a generally perspective exploded view of the alternate form of the invention shown in FIG. 43.

FIG. 51 is a generally perspective view of still another embodiment of the fluid delivery apparatus of the present invention for dispensing fluids at a uniform rate.

FIG. 53 is a cross-sectional view taken along lines 53-53 of FIG. 52.

FIG. 54 is a left-end view of the apparatus shown in FIG. 52.

FIG. 55 is a side view of the vial cover assembly of the apparatus of the invention.

FIG. 56 is a view taken along lines 56-56 of FIG. 55.

FIG. 57 is an enlarged, longitudinal, cross-sectional view of one of the fill vial assemblies shown in FIG. 52.

FIG. 58 is a cross-sectional view taken along lines 58-58 of FIG. 57.

FIG. 59 is an enlarged, longitudinal, cross-sectional view of the other fill vial assembly of the apparatus of the invention.

FIG. 60 is a cross-sectional view taken along lines 60-60 of FIG. 59.

FIG. 61 is a cross-sectional view of an alternate form of fill vial assembly of the invention.

FIG. 62 is a cross-sectional view taken along lines 62-62 of FIG. 61.

FIG. 64 is a generally perspective view of still another embodiment of the fluid delivery apparatus of the present invention for dispensing fluids at a uniform rate.

FIG. 83 is a generally perspective, exploded front view of the rate control assembly shown in FIG. 81.

FIG. 84 is a generally perspective exploded rear view of the rate control assembly shown in FIG. 81.

FIG. 87 is an exploded view of still another form of the rate control assembly of the invention.

FIG. 88 is an exploded view of yet another form of the rate control assembly of the invention.

DETAILED DESCRIPTION OF THE INVENTION

Figure 1:
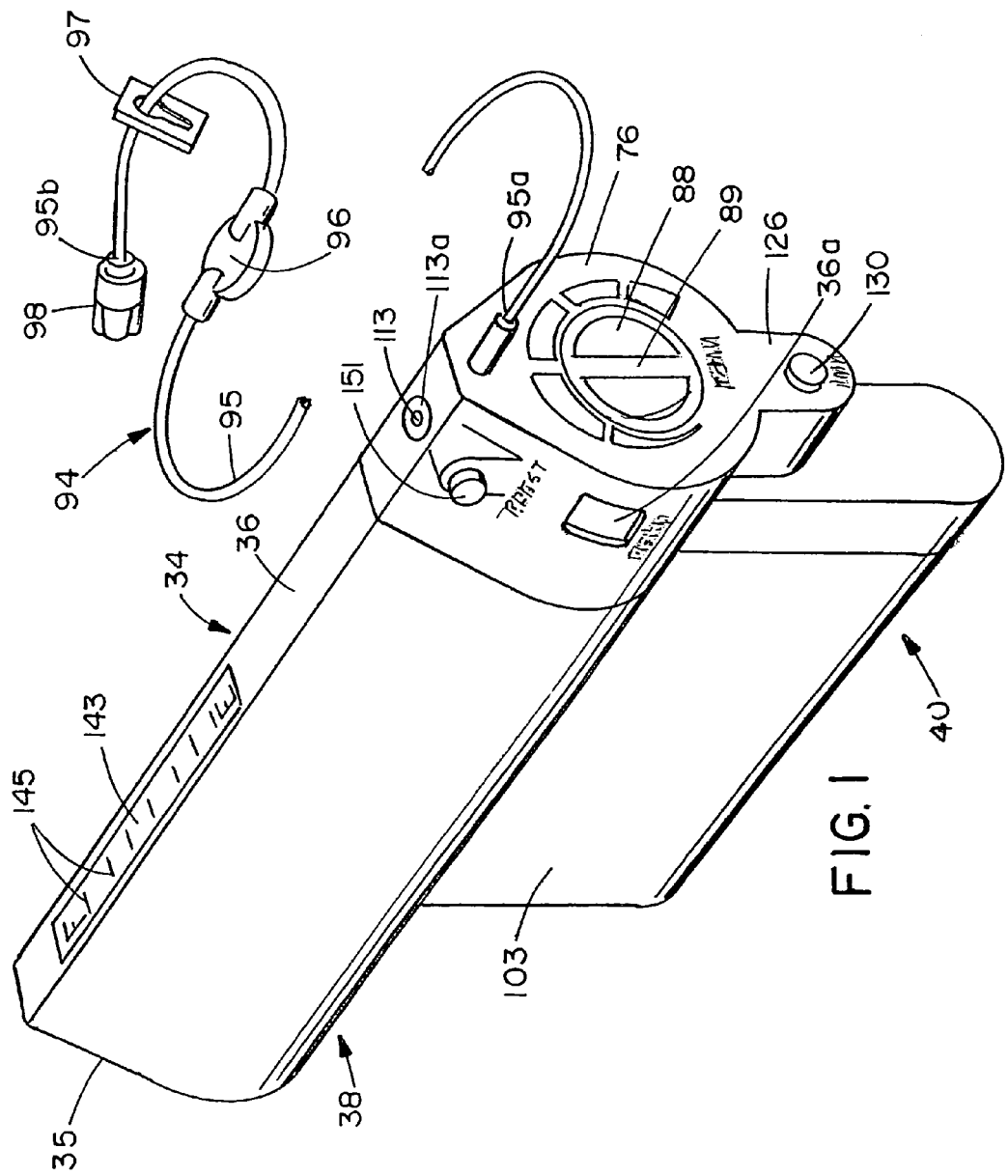
FIG. 1 is a generally perspective view of one embodiment of the fluid delivery apparatus of the present invention for dispensing fluids at a uniform rate.

Referring to the drawings and particularly to FIGS. 1 through 8H, one embodiment of the dispensing apparatus of the present invention is there illustrated and generally designated by the numeral 34. As best seen in FIGS. 1 and 2A and 2B, the apparatus here comprises a snap-together plastic outer housing 35 having a first, second and third portions 36, 38 and 40 respectively. Disposed within outer housing 34 is an inner, expandable housing 42 having a fluid reservoir 44 provided with an inlet 46 (FIG. 2B) for permitting fluid flow into the fluid reservoir and an outlet 48 for permitting fluid flow from the fluid reservoir. Expandable housing 42, which can be constructed from a metal or plastic material, comprises a bellows structure having an expandable and compressible, accordion-like, annular-shaped sidewall 42a, the configuration of which is best seen in FIG. 3. If the internal materials interface of the bellows structure and other fluid channels or surfaces are not sufficiently compatible with the planned beneficial agent to be delivered, either in terms of its biocompatibility or drug up-take characteristics, application of a surface modification process is appropriate. This surface modification methodology which may involve one or more layers, may take one of several forms. One process that is extremely clean, fast and efficient is plasma processing. In particular this technique allows for any of the following: plasma activation, plasma induced grafting and plasma polymerization of molecular entities on the internal drug surface of the bellows. For cases where an inert hydrophobic interface is desired, plasmas using fluorine-containing molecules may be employed. That is, the bellows surface as well as other surfaces that may be contacted by the beneficial agent may be cleaned with an inert gas plasma and subsequently a fluorine-containing plasma may be used to graft these molecules to the surface. Alternatively, if a hydrophilic surface is desired (e.g. for drug solutions that are highly corrosive or in oil-based solvents) an initial plasma cleaning may be done, followed by a plasma polymerization using hydrophilic monomers.

Figure 2A:
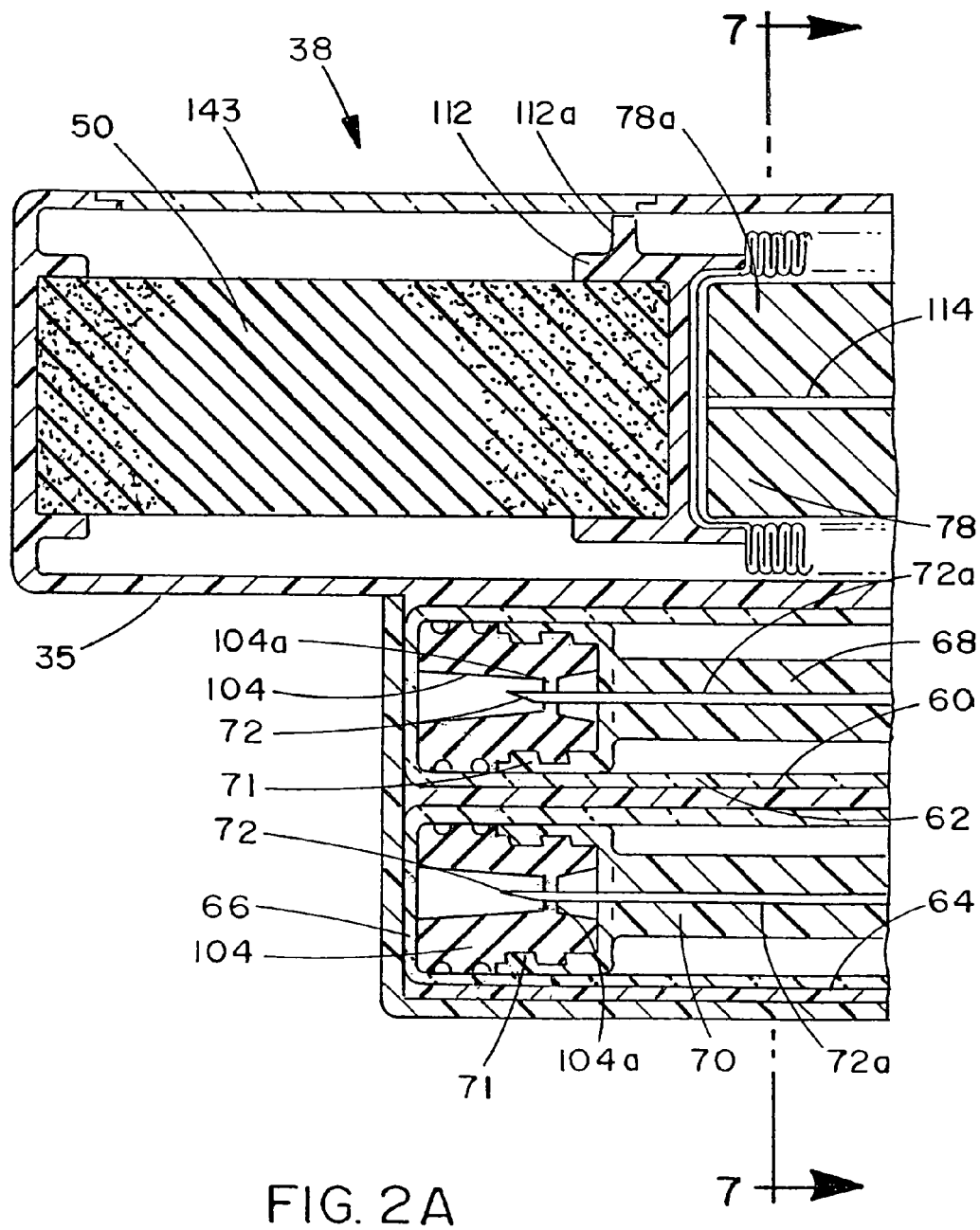
FIG. 2A is an enlarged longitudinal cross-sectional rear view of the apparatus shown in FIG. 1.
Figure 2B:
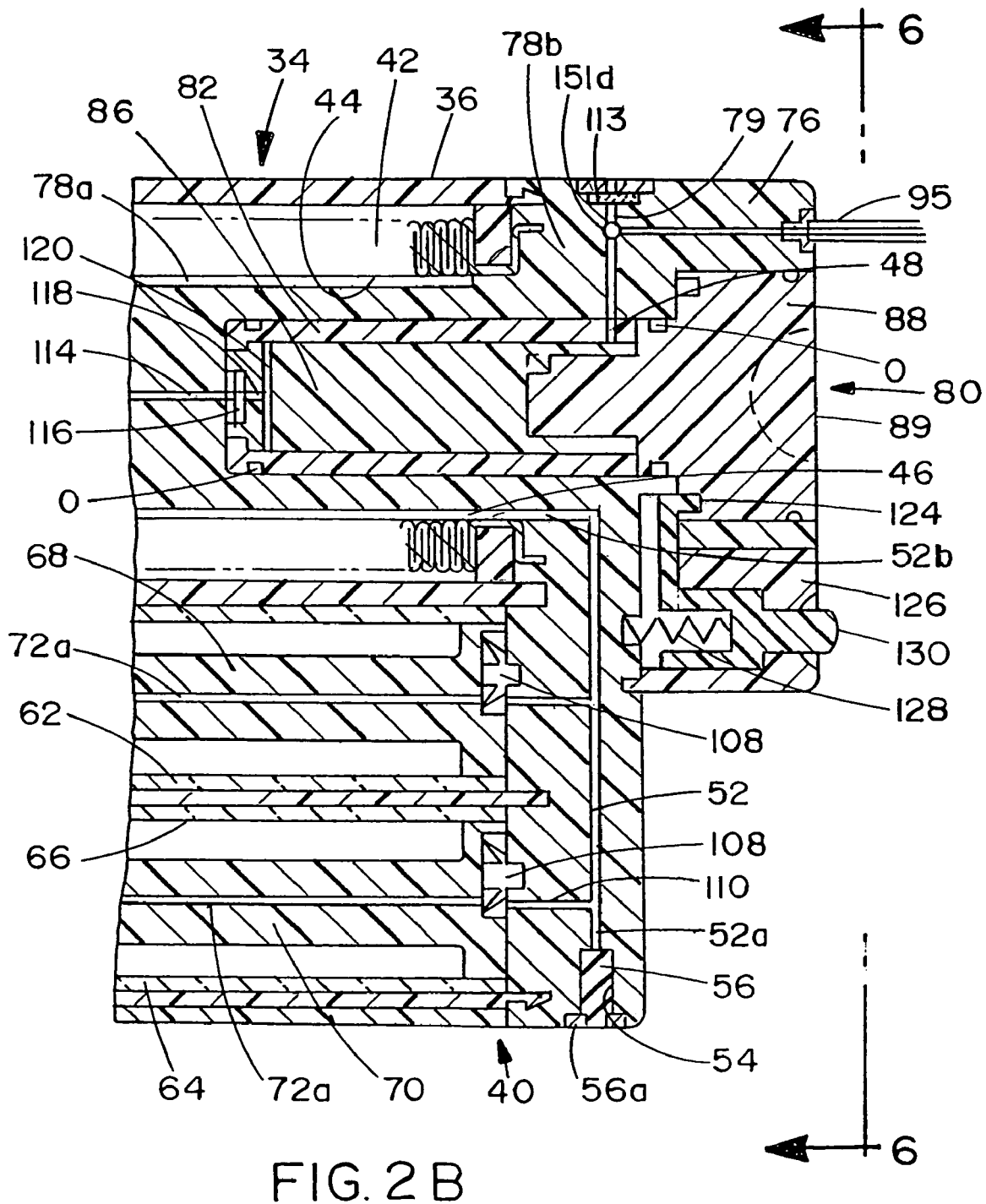
FIG. 2B is an enlarged longitudinal cross-sectional front view of the apparatus shown in FIG. 1.

Disposed within second portion 38 of outer housing 34 is the novel stored energy means of the invention for acting upon expandable housing 42 in a manner to controllably collapse the expandable housing so as to cause the fluid contained within fluid reservoir 44 to controllably flow outwardly of the housing. In the present form of the invention, this important stored energy means here comprises a compressively deformable, generally homogeneous member 50 that is carried within the second portion 38 of the outer housing. As used herein, the term "homogeneous" means a member of the same general composition or structure throughout, that is, of the same kind and nature as opposed to a member consisting of different elements. In a manner presently to be described, member 50 which is depicted in FIG. 2A as an elastomeric polymeric member, is first compressed by fluid flowing into reservoir 44 and then is controllably expanded to cause fluid to flow from the outer housing through the dispensing means of the invention. It is to be understood that the stored energy means can be constructed from a wide variety of solid, semi-solid, and cellular materials including open cell, closed cell, syntactic forms with micro spheres, rubbers, foams, sponges, metalized foams, plastics and other thermoplastic elastomers (TPE). Other suitable materials include latex rubber, rubber polyolefins, polyisoprene (natural rubber), butyl rubber, nitrile rubber, polystyrene, polyethylene, polyvinyl chloride polyurethane, vinyls, vinyl-end-blocked polydimethylsiloxanes, other homopolymer, copolymers (random alternating, block, graft, cross-link and star block), silicones and other flouropolymers, mechanical poly-blends, polymer alloys and interpenetrating polymer networks. Suppliers of elastomeric materials suitable for construction of member 50 include "2 and 5 Plastics" of Newark, N.J.; Ludlow Composite Corp. of Fremont, Ohio and Polymer Technologies, Inc. of Newark, Del. Member 50 can also comprise a ductile metalized foam of the character available from various sources, including "Chemetall" of Frankfurt, Germany Forming an important aspect of the apparatus of the present invention is fill means carried by the third portion 40 of outer housing 34 for filling the reservoir 44 with the fluid to be dispensed. As best seen in FIG. 2B, third portion 40 includes a fluid passageway 52 in communication with inlet 46 of fluid reservoir 44. Proximate its lower end 52a, fluid passageway 52 communicates with a cavity 54 formed within the third portion of the housing 34. Disposed within cavity 54 is a pierceable septum 56 that comprises a part of one form of the fill means of the invention. Septum 56 is held in position by a retainer 56a and is pierceable by the needle of the syringe which contains the medicinal fluid to be dispensed and which can be used in a conventional manner to fill or partially fill reservoir 44 via passageway 52 or to retrieve fluid from reservoir 44. Septum 56 can be a slit or a solid septum constructed from an elastomeric material such as silicone rubber. Additionally, a mechanical check valve can function as a septal interface, for drug filling and for residual drug recovery such as valves available from C. R. Bard of Murray Hill, N.J.

Third portion 40 of housing 34 also includes a first chamber 60 for telescopically receiving a first medicament containing fill vial 62 such as a closed-end glass or plastic shell vial, and a second chamber 64 for telescopically receiving a similarly constructed second medicament containing vial 66. An elongated support 68 is mounted within said first chamber 60 and a second elongated support 70 is mounted within second chamber 64. Each of the elongated supports 68 and 70 has an integrally threaded end portion 71 and carries a longitudinally extending, elongated hollow needle or cannula 72. Each of the hollow needles 72 has a flow passageway 72a that communicates with fluid passageway 52. First chamber 60, second chamber 64, elongated support 68, elongated support 70 and hollow needles 72 together comprise an alternate form of the fill means of the apparatus of the invention. The method of operation of this alternate form of fill means will presently be described.

Forming another very important aspect of the apparatus of the present invention is a novel flow control means that is connected to first portion 36 of outer housing 34. This flow control means functions to precisely control the outwardly rate of fluid flow from reservoir 44 and toward the patient. In the form of the invention shown in FIGS. 1 through 18 the flow control means comprises a flow control assembly generally designated in the drawings by the numeral 76. This novel flow control assembly here comprises an ullage defining member 78 having a first portion 78a disposed within inner, expandable housing 42 and a second portion 78b to which the bellows is bonded. Portion 78b extends outwardly from housing 42 in the manner shown in FIG. 2B. Bellows 42 cooperates with and is slidably movable relative to ullage portion 78a in the manner shown in FIGS. 2B and 3. For a purpose presently to be described, member 78b has a fluid passageway 79 that is in communication with an outlet of the flow control subassembly 80, the character of which will next be described. Portion 78a of the ullage member functions to ensure that substantially all of the medicinal fluid contained within the bellows reservoir will be dispensed from the device.

Referring to FIGS. 10 through 13, it can be seen that flow control subassembly 80, which comprises a part of flow control assembly 76, includes an outer casing 82 having a plurality of circumferentially spaced apart fluid outlets 84 (see FIG. 10), a flow control member 86 telescopically receivable within casing 82 and a selector knob 88 that is interconnected with control member 86 in the manner shown in FIGS. 9 and 12. O-rings generally designated in the drawings as "O" sealably interconnect the various components (see FIG. 15). As best seen in FIGS. 10 and 13, flow control member 86 is uniquely provided with a plurality of elongated flow control channels 90, each having an inlet 90a and an outlet 90b. The flow channels 90 may be of different sizes, lengths, width and depth and configurations as shown by FIGS. 13A and 13B which depict alternate patterned forms of the flow control member, here identified as 86a and 86b. The flow control channels identified in FIG. 13B by the numeral 90b are formed in individual, spaced-apart capillary segments 91 and define the circuitous flow path depicted in FIG. 13B. Further, the flow control channels may be rectangular in cross-section as illustrated in FIG. 11, or alternatively, they can be semicircular in cross-section, U-shaped in cross-section, or they may have any other cross-sectional configuration that may be appropriate to achieve the desired fluid flow characteristics. As indicated by the designation "C", when necessary for drug compatibility reasons, the flow channels can be appropriately coated in the manner indicated in FIG. 11. Coating "C" can be of various types and the coating can be applied by several techniques including the earlier-described cold plasma processing technique. When the flow control member is properly positioned within outer casing 82, the inner surface of the outer casing wall sealably cooperates with channels 90 to form a plurality of individual shaped fluid flow passageways of different overall lengths and flow capacities. When the flow control member is positioned within the outer casing in the manner shown in FIG. 12, a notch 86b formed in member 86 receives a tongue 82a provided on casing 82 so as to precisely align the outlets 90b of the flow channels 90 with fluid outlets 84 formed in casing 82 (see FIG. 10).

The flow control channels 90 can be made by several techniques including (micro) injection molding, injection-compression molding, hot-embossing and casting. The techniques used to make these imbedded fluid channels are now common-place in the field of microfluidics, which gave rise to the lab-on-a-chip, bio-MEMS and micro-total analysis systems (m-TAS) industries. Additionally, depending on the size of the fluid channels required for a given flow rate, more conventional injection molding techniques can be used.

The first step in making the channels using an injection molding or embossing process is a lithographic step, which allows a precise pattern of channels to be printed on a "master" with lateral structure sizes down to 0.5 mm. or less. Subsequently, electroforming is performed to produce the negative metal form, or mold insert. Alternatively for larger channel systems, precision milling can be used to make the mold insert directly. Typical materials for the mold insert or embossing tool are nickel, nickel alloys, steel and brass. Once the mold insert of the embossing tool is fabricated, the polymer of choice may be injection molded or embossed to yield the desired part with imprinted channels.

Alternatively, channels can also be made by one of a variety of casting processes. In general, a liquid plastic resin (e.g. a photopolymer) can be applied to the surface of a metal master (made by the techniques described above) and then cured via thermal or UV means. After hardening, the material is then "released" from the mold to yield the desired part. Additionally, there are similar techniques available that utilize CAD data (of the desired channel configuration) and direct laser curing of a liquid monomer to yield a polymerized and solidified part with imbedded channels. This process is available from multiple sources including MicroTEC MbH of Duisburg, Germany.

A number of materials can be used to fabricate flow control member 86. While medical grade polymers are the most appropriate materials, other materials can be used including: Thermoplastics (embossing & injection molding); Duroplastics (injection molding); Elastomers (injection compression molding and soft lithography); Polyurethanes (castings); and Acrylics and Epoxies.

Selector knob 88, which comprises a part of the selector means of the invention, is rotatably connected to second portion 78b of ullage defining member 78 and, in a manner presently to be described, functions to rotate the assembly made up of outer casing 82 and flow control member 86. In this way, a selected outlet 84 in casing 82 can be selectively aligned with flow passageway 79 provided in the ullage defining member (see FIG. 2B).

Turning once again to FIG. 1, also forming a part of the fluid dispensing apparatus of the present invention is dispensing means for dispensing fluid to the patient. In the present form of the invention this dispensing means comprises an administration set 94 that is connected to the first portion 36 of housing 34 in the manner shown in the drawings. The proximal end 95a of administration line 95 of the administration set or channel 94 is in communication with fluid passageway 79 in the manner best seen in FIG. 2B. Disposed between the proximal end 95a and the distal end 95b of the administration line is a conventional gas vent and particulate filter 96 and clamp 97. Provided at the distal end 95b is a luer connector 98 of conventional construction.

Turning now to FIGS. 4 and 5, the details of construction of a glass or plastic shell vial 62, which vial is identical in construction to fill vial 66, is there shown. As indicated in these Figures, each of the fill vials includes a body portion 100, having a fluid chamber 102 for containing an injectable fluid. Chamber 102 is provided with a first open end 100a and second closed end 100b. First open end 100a is sealably closed by closure means here provided in the form of an externally threaded elastomeric plunger 104 which is telescopically movable within the vial from a first location shown in FIG. 4, where the plunger is disposed proximate first open end 100a, to a second device-fill location shown in FIG. 2A where the plunger is disposed proximate second closed end 100b.

After opening of closure 103, which forms a part of the third portion 40 of housing 34 (FIG. 3), vials 62 and 66 can be inserted into chambers 60 and 64 respectively. As the fill vials are so introduced and the plungers 104 are threadably interconnected with ends 71 of supports 68 and 70, the sharp ends of the elongated needles will pierce the central walls 104a of the elastomeric plungers. Continuous longitudinal movement of the vials into chambers 60 and 64 will cause the structural supports 68 and 70 to move the elastomeric plungers inwardly of the vial chambers in a direction toward the second closed end 100b of the vials. As the plunger is moved inwardly of the vial in the manner shown in the lower portion of FIG. 3, wherein only vial 66 is shown being used, the fluid contained within the vial chamber will be expelled therefrom into the passageway 72a of hollow elongated needles 72. As best seen in FIG. 2B, the fluid will then flow past umbrella type check valves 108 and into passageways 110 formed in third portion 40 of the apparatus housing. Elastomeric umbrella type check valves 108 will function to substantially block reverse fluid flow from fluid passageways 110. From passageways 110 the fluid will flow into passageway 52, into stub passageway 52b and then into the reservoir portion 44 of the bellows component 42 via inlet 46 which comprises micro-channels formed in ullage 78a. It is to be understood that the vials 62 and 66 can contain the same or different medicinal fluids or diluents and can be installed into their respective chambers in the manner shown in FIGS. 2A and 3.

As the fluid flows into the reservoir portion of the bellows, the bellows will be expanded from the collapsed configuration shown in FIG. 2A into an expanded configuration such as shown in FIG. 3. As the bellows member expands it will simultaneously urge a telescopically movable volume indicator member 112 that is carried within second portion of the housing into engagement with the stored energy source, or compressible-expandable member 50 causing it to compress. It is also to be understood that, if desired, the reservoir portion of the bellows component can also be filled by alternate filling means of the character previously described which comprises a syringe having a needle adapted to pierce the pierceable septum 56 which is mounted within third portion 40 of the apparatus housing. Fluid can also be retrieved from the reservoir using a syringe in conjunction with a mechanical septum or, alternatively, septum 56.

Figure 8A:
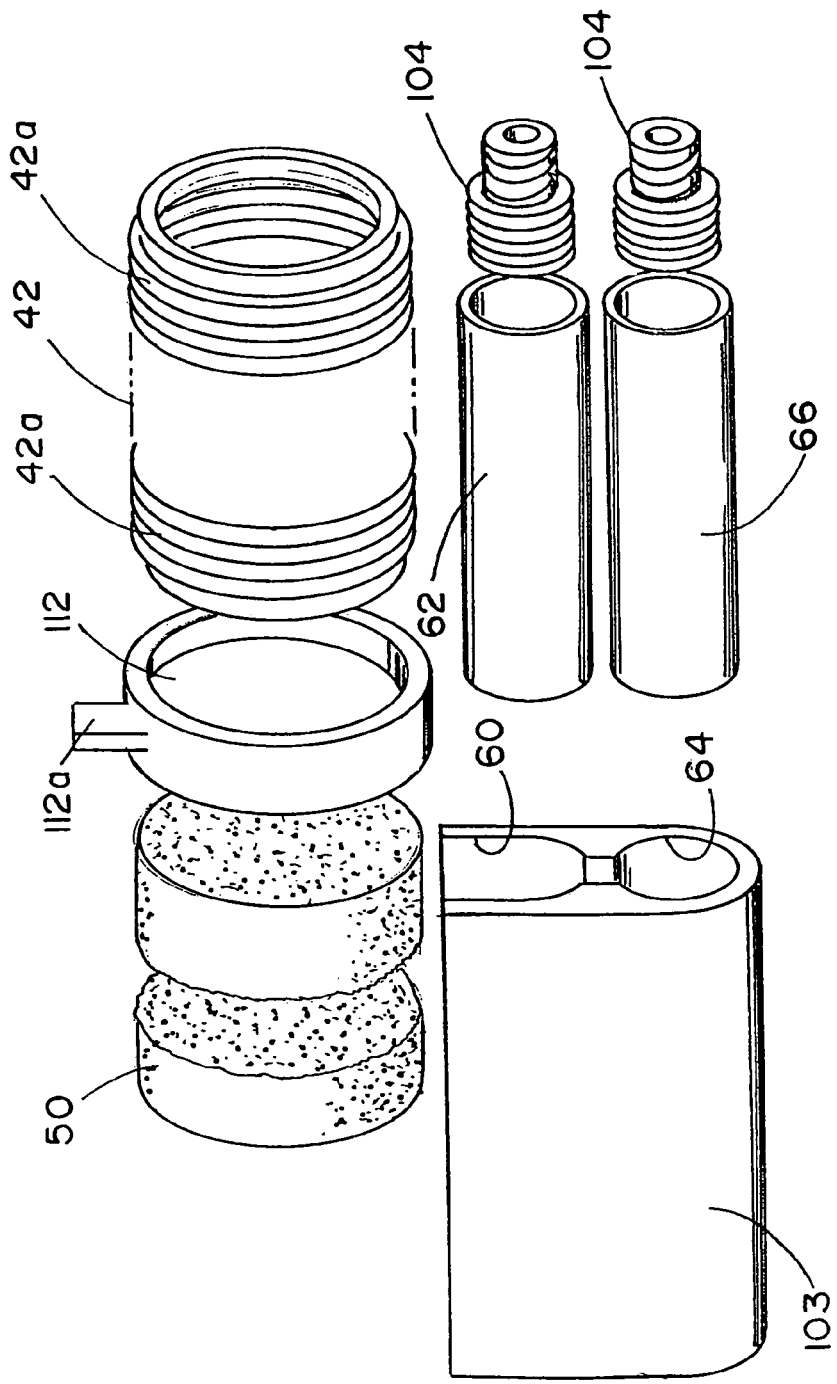
FIGS. 8A and 8B, when considered together comprise a generally perspective, exploded view of the various internal operating components of the apparatus of the invention.
Figure 8B:
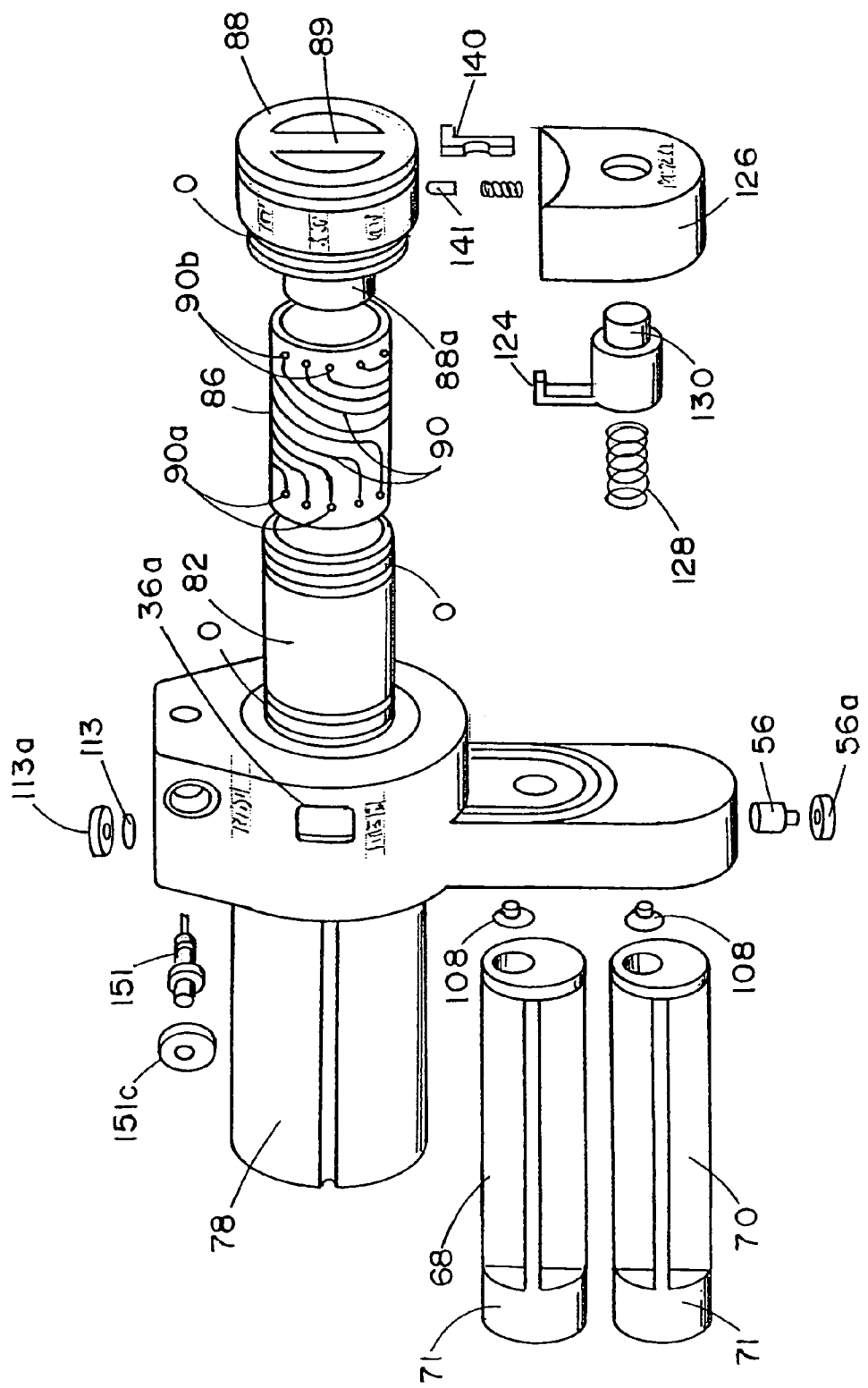
Figure 8C:
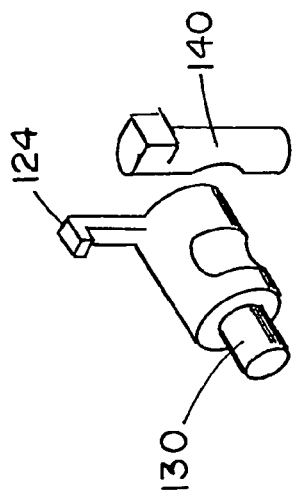
FIG. 8C is a generally perspective exploded view of one form of the indexing means of the invention.
Figure 8E:
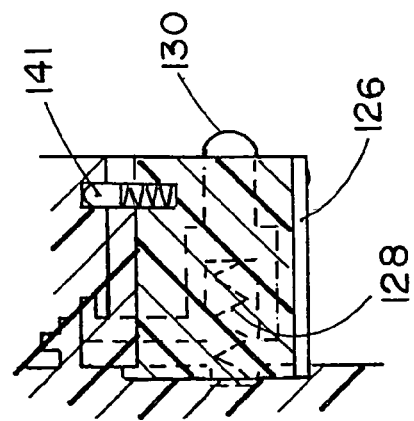
FIG. 8E is a cross-sectional view taken along lines 8E-8E of FIG. 8D.
Figure 8D:
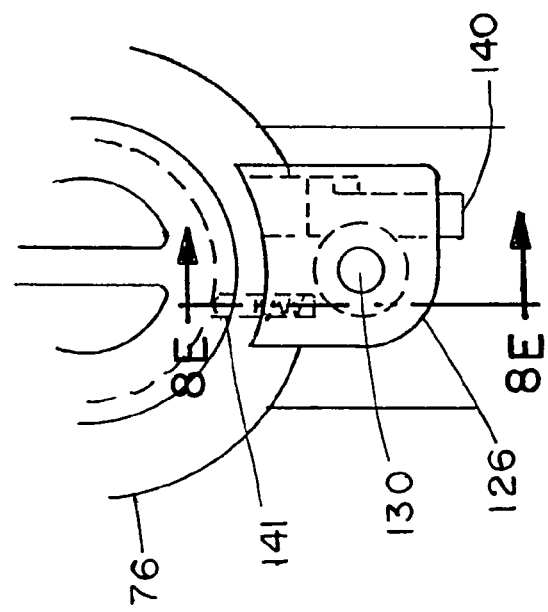
FIG. 8D is a fragmentary front view similar to the front view shown in FIG. 6, but better showing the configuration of the indexing means of the invention.

As the reservoir 44 fills with fluid either from the fill vials or from the filling syringe, any gases trapped within the reservoir will be vented to atmosphere via vent means "V" mounted in portion 78b of the ullage member. This vent means here comprises a gas vent 113 that is bonded to the housing and can be constructed of a suitable hydrophobic porous material such as a porous plastic. Bonded gas vent 113 is held in position within the housing by a retainer ring 113a (FIG. 8B). This alternate fill means can be used to initially fill the reservoir or alternatively can be used to add an injectable fluid such as an adjuvant fluid.

Upon opening the fluid delivery path to the administration set 94 in a manner presently be described, the stored energy means, or member 50, will tend to return to its starting configuration thereby controllably urging fluid flow outwardly of reservoir 44 via passageway 114 and the flow control means of the invention.

As previously discussed, a number of beneficial agents can be contained within liquid vial containers 62 and 66 and can be controllably dispensed to the patient including, by way of example, medicaments of various types, injectable drugs, pharmaceuticals, hormones, antibodies, biologically active materials, elements, chemical compounds, or any other suitable material useful in diagnostic cure, medication, treatment or preventing of diseases or the maintenance of the good health of the patient.

Considering next the important operation of the fluid flow rate control means of the invention, as the fluid contained within the bellows reservoir 44 is urged outwardly thereof by the stored energy means, the fluid will flow into a fluid passageway 114 formed in the first portion 78a of ullage member 78. The fluid will then flow under pressure through a filter means shown here as a filter 116 that is carried in a cavity provided in the flow control member 86 of the flow control subassembly 80. Filter 116 which functions to filter particulate matter, undissolved drugs, or precipitates from the fluid flowing outwardly from reservoir 44, is of a character well known to those skilled in the art and can be constructed from various readily available materials such as polysulfone and polypropylene wafers having a desired porosity. After flowing through filter 116, the fluid will flow, via a stub passageway 118 (FIG. 15) into the distribution means of the invention for distributing fluid from the fluid reservoir to each of the plurality of spiral passageways 90. This distribution means here comprises several radially outwardly extending flow passageways 120 formed in flow control member 86. The filtered fluid will fill passageways 120 and then will flow into the plurality of spiral passageways 90 formed in member 86 via outlets 90b, which communicate with passageways 120 (see FIG. 10). The fluid contained within spiral passageways 90 can flow outwardly of the device housing only when one of the fluid outlets 84 formed in casing 82 is aligned with reservoir outlet 79.

Selection of the passageway 90 from which the fluid is to be dispensed is accomplished by rotation of the selector knob 88 which, as best seen in FIG. 13 includes a reduced diameter portion 88a having a slot 88b formed therein. As illustrated in FIG. 13, slot 88b is adapted to receive a spline 86a (FIG. 10) formed anteriorly of member 86. With this construction, rotation of selector member 88 by gripping a transversally extending finger gripping member 89 will impart part rotation to member 86. As seen in FIG. 13, casing 82 is also provided with an inwardly extending spline segment 82a that is received within a slot 86b formed in the rearward periphery of member 86. Accordingly, rotation of member 86 will also impart concomitant rotation to casing member 82.

As illustrated in FIGS. 12 and 13, selector knob 88 is provided with a plurality of circumferentially spaced apart indexing cavities 88c that closely receive an indexing finger 124 (see FIG. 2B) which forms a part of the indexing means of the invention, which means comprises a locking shaft cover 126 that is connected to third portion 40 of the apparatus housing (see FIGS. 1 and 2B). Indexing finger 124 is continuously urged into engagement with a selected one of the indexing cavities 88c by a coil spring 128 that also forms a part of the indexing means of the invention. Coil spring 128 (FIG. 2B) can be compressed by an inward force exerted on an indexing shaft 130 that is mounted in locking shaft cover 126 and is movable from the extended position shown in FIG. 2B to an inward, finger release position wherein spring 128 is compressed and finger 124 is retracted from a selected indexing cavity 88c. With finger 124 in its retracted position it is apparent that control knob 88 can be freely rotated to a position wherein flow rate indicia 134 (see FIGS. 9 and 13) formed on the periphery of knob 88 (FIG. 9) can be viewed through a viewing window 36a formed in the first portion 36 (see FIG. 1) of the apparatus housing. Locking means, here provided in the form of a locking tab 140 (see FIG. 8C), is also carried by the locking shaft cover and, when moved from the release position shown in FIG. 8G into the locking position shown in FIG. 8H, prevents inward movements of the indexing shaft 130 against the urging of spring 128 (FIGS. 6A, 8B, 8D, 8E and 8F). A spring biased retainer pin 141 (FIG. 8E) functions to retain the selector knob in position within housing 34.

When the selector knob is in the desired position and pressure is released on indexing shaft 130, spring 128 will urge finger 124 of the indexing means of the invention into locking engagement with one of the indexing cavities 88c thereby placing a selected one of the spiral shaped flow control channels 90 in communication with the fluid reservoir 44 via passageways 120, 118 and 114. As the fluid flows outwardly of the apparatus due to the urging of the stored energy means 50, the bellows structure 42 will be collapsed and at the same time member 112 will travel inwardly of housing portion 38. Member 112, which forms a part of the volume indicator means of the invention, includes a radially outwardly extending indicating finger 112a that is visible through a volume indicator window 143 that is provided in second portion 38 of the apparatus housing and also comprises a part of the volume indicator means of the invention (FIG. 1). Indicia 145, which are provided on indicator window 143, function to readily indicate to the caregiver the amount of fluid remaining within fluid reservoir 44.

A safety disabling means is shown here as a disabling shaft 151 that is telescopically movable within a passageway 151*a* formed within the housing functions to disable the device and render it unusable. More particularly, shaft 151 has a distal end 151*b* which, upon insertion of the shaft, will block fluid flow through passageway 79. A retainer 151*c* normally holds shaft 151 in the retracted position (see FIG. 3A).

Figure 19:
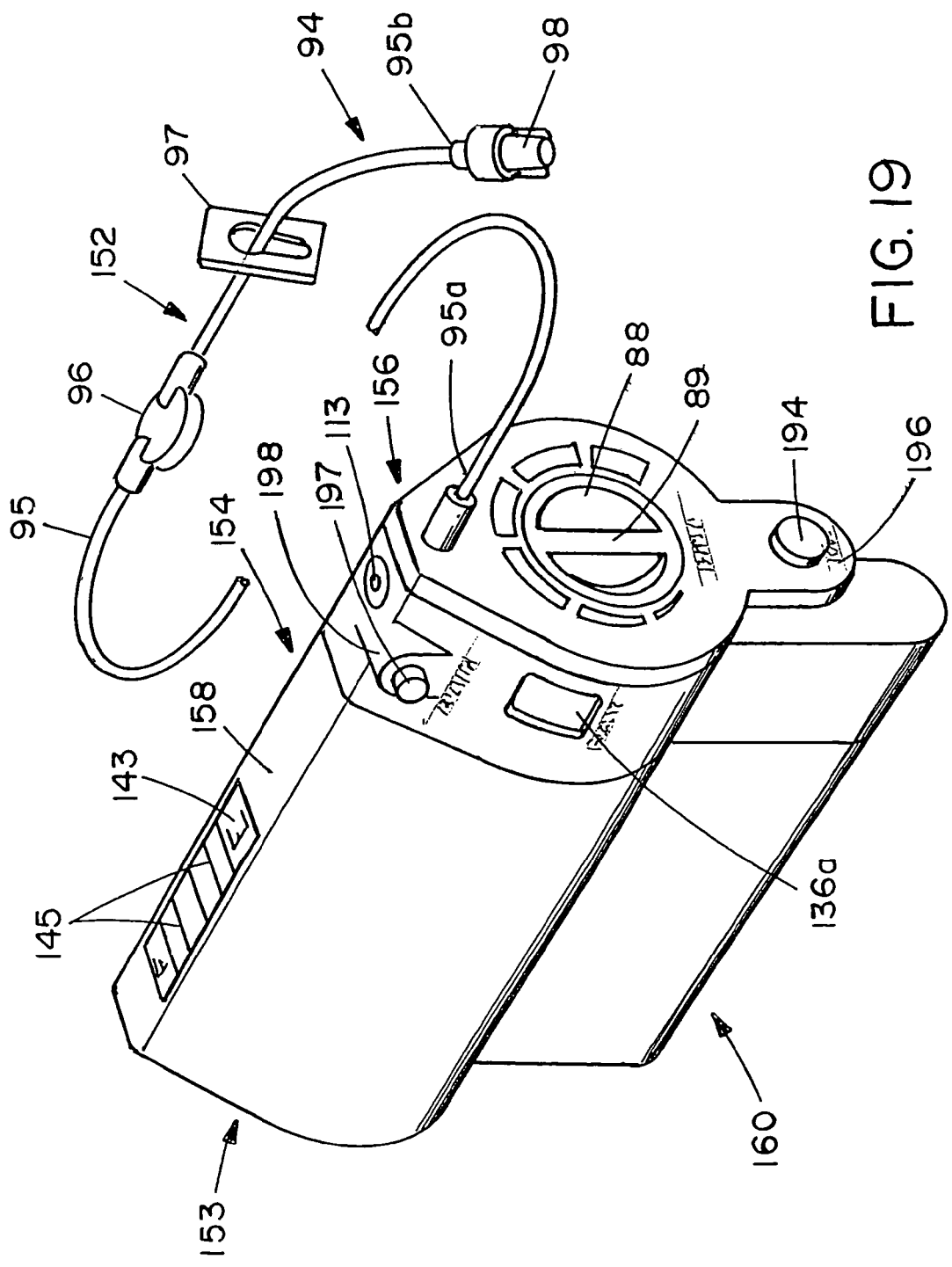
FIG. 19 is a generally perspective view of an alternate embodiment of the fluid delivery apparatus of the present invention for dispensing fluids at a uniform rate.
Figure 20:
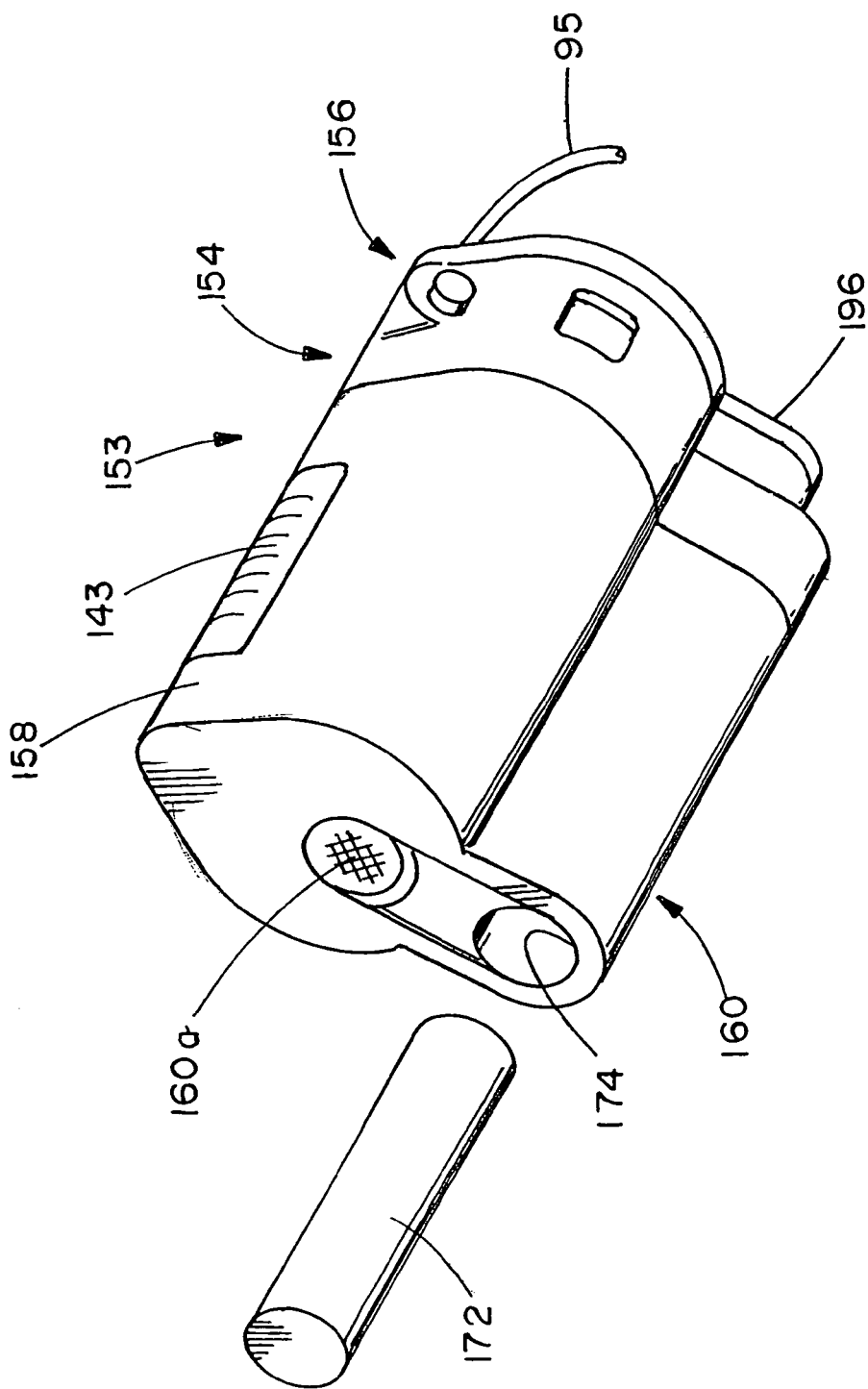
FIG. 20 is a generally perspective exploded rear view of the alternate form of the invention shown in FIG. 19.
Figure 21:
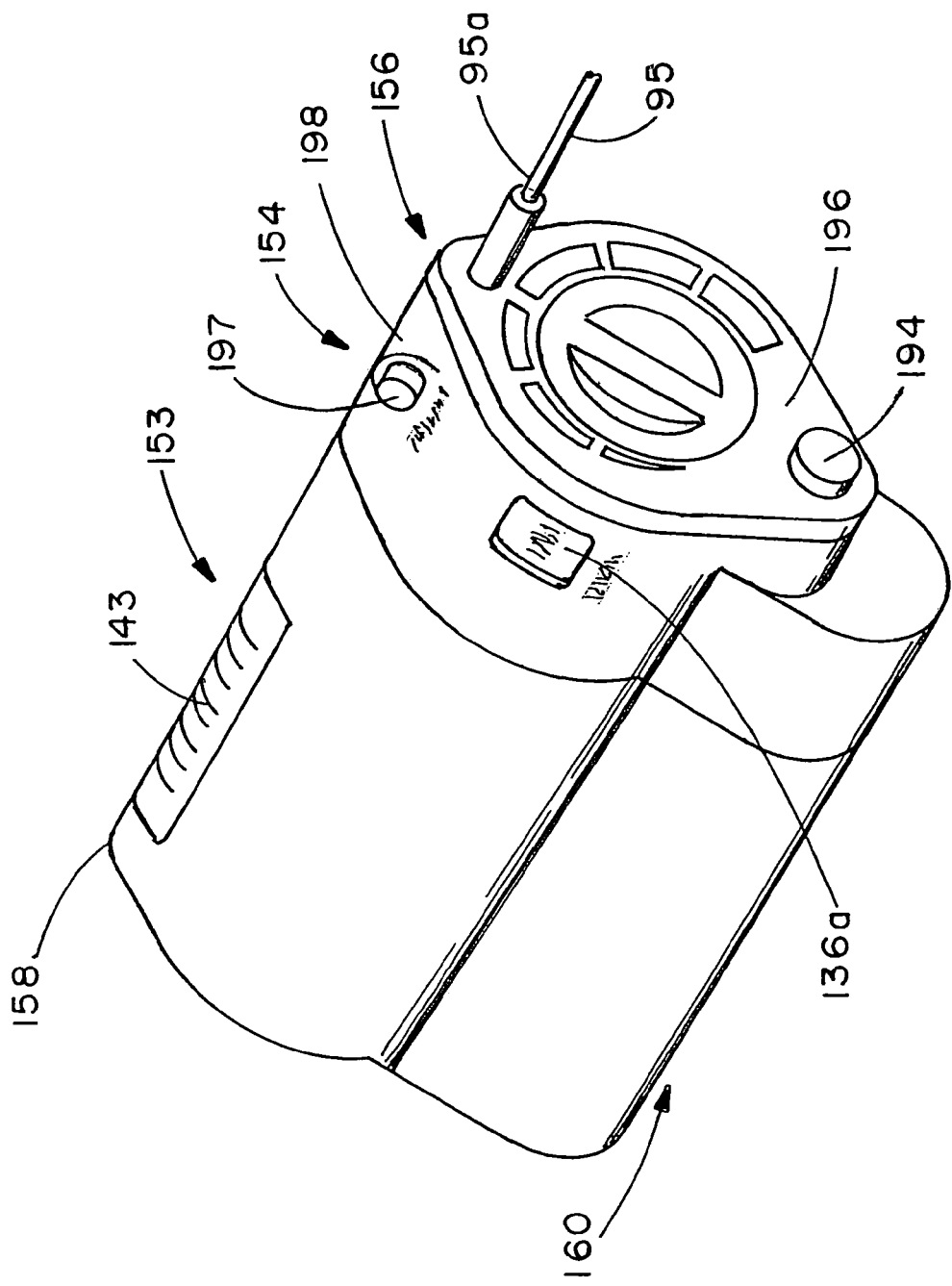
FIG. 21 is a generally perspective front view of the alternate form of the invention shown in FIG. 19.

Turning next to FIGS. 19 through 31, an alternate embodiment of the dispensing apparatus of the present invention is there illustrated and generally designated by the numeral 153. This alternate form of the apparatus of the invention is similar in many respects to that shown in FIGS. 1 through 18 and like numerals are used in FIGS. 19 through 31 to identify like components. As best seen in FIGS. 19, 20 and 21, the apparatus of this alternate form of the invention comprises an outer housing 154 having first, second and third portions 156, 158 and 160 respectively. Disposed within outer housing 154 is an inner, expandable housing 162 that is quite similar in construction and operation to expandable housing 42. Housing 162 includes a fluid reservoir 164 that is provided with an inlet 166 (FIG. 22) for permitting fluid flow into the fluid reservoir. Expandable housing 162, like expandable housing 42, comprises a bellows structure having an expandable and compressible, accordion-like, annular sidewall 162*a* of the character best seen in FIG. 22.

Disposed within second portion 158 of outer housing 154 is the stored energy means of the invention for acting upon inner expandable housing 162 in a manner to cause the fluid contained within fluid reservoir 164 to controllably flow through outlet 185. In this alternate form of the invention, the important stored energy means is also similar in construction and operation to the earlier described stored energy means and here comprises a compressively deformable, elastomeric member 170 that is carried within the second portion 158 of the outer housing. As before, in operation member 170 is first compressed by fluid flowing into reservoir 164 and then is controllably expanded to cause fluid flow from the fluid reservoir. Stored energy member 170 can be constructed from a wide variety of materials including those materials earlier described herein.

As in the earlier described embodiment of the invention, the apparatus of this alternate form of the invention comprises fill means carried by the third portion 160 of outer housing 154 for filling the reservoir 164 with the fluid to be dispensed. This fill means is also similar to the earlier described fill means, save for the fact that the fill means of this latest embodiment comprises only one fill vial 172 which is identical in construction and operation to the earlier described fill vial 62. As before, the fill means also includes an alternate fill means that comprises a pierceable septum 56 that is disposed within a cavity 54 formed in the third portion 160 of outer housing 154. Septum 56 is pierceable by the needle of the syringe which contains the medicinal fluid to be dispensed and which can be used to fill or partially fill reservoir 164 or to recover medicinal fluid therefrom via a passageway 171 formed in third portion 160.

Third portion 160 of housing 154 includes a chamber 174 for telescopically receiving the medicament containing fill vial 172. An elongated support 178, which is mounted within chamber 174, is provided with an internally threaded end portion 175 and a longitudinally extending, elongated hollow needle 180 which has a flow passageway 180*a* that communicates with a fluid passageway 171 via an umbrella type check valve 182 and a stub passageway 171*a*.

The apparatus of this latest form of the invention also includes flow control means that is quite similar in construction and operation to the flow control means described in connection with the embodiment of the invention shown in FIGS. 1 through 18. This flow control means is connected to first portion 156 of outer housing 154 and comprises an ullage defining member 184 having a first portion 184*a* disposed within inner, expandable housing 162 and a second portion 184*b* having a fluid passageway 185 that is in communication with fluid reservoir 164

As before, the flow control means includes a flow control subassembly that is substantially identical in construction and operation to the earlier described flow control subassembly 80 and is of the configuration shown in FIGS. 9, 10, 12 and 13 of the drawings. Accordingly, the details of the construction and operation of the control means of this latest embodiment of the invention will not be here repeated and reference should be made to the earlier description of the flow control subassembly 80.

Turning once again to FIG. 19, also forming a part of the fluid dispensing apparatus of this latest form of the invention is dispensing means for dispensing fluid to the patient. This dispensing means is identical in construction and operation to the previously identified administration set 94 and is connected to the first portion 156 of housing 154.

Turning now to FIGS. 23 and 24, it is to be noted that glass or plastic shell vial 172 is identical in construction to fill vial 66 and includes a fluid chamber 102 for containing an injectable fluid. Chamber 102 is provided with a first open end 100*a* and second closed end 100*b*. First open end 100*a* is sealably closed by closure means here provided in the form of an externally threaded elastomeric plunger 104 which is telescopically movable within the vial from a first location shown in FIG. 24, where the plunger is disposed proximate first open end 100*a*, to a second location where the plunger is disposed proximate second, closed end 100*b*.

Figure 22:
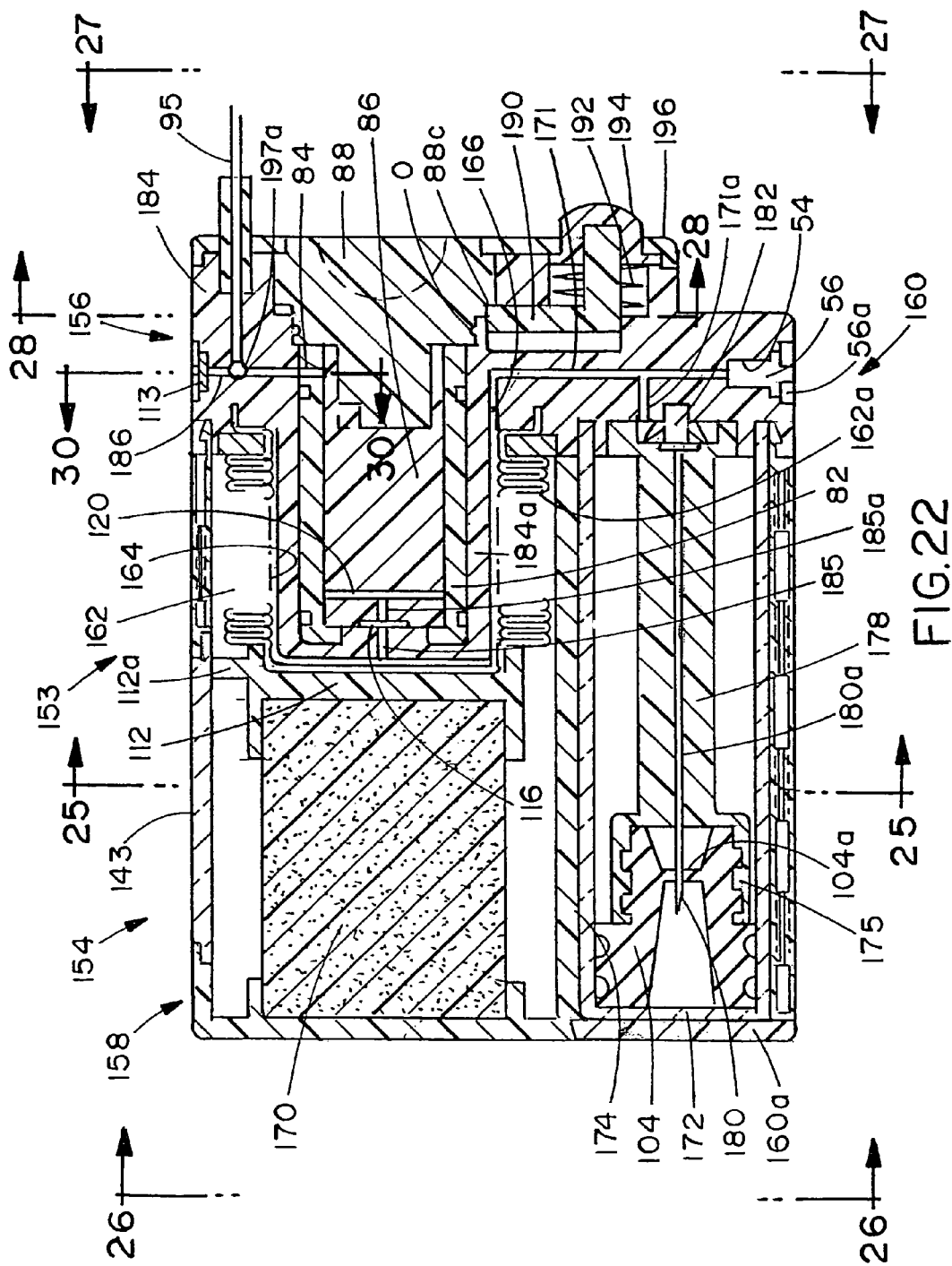
FIG. 22 is an enlarged longitudinal cross-sectional view of the manifold and control apparatus shown in FIG. 19.
Figure 22A:
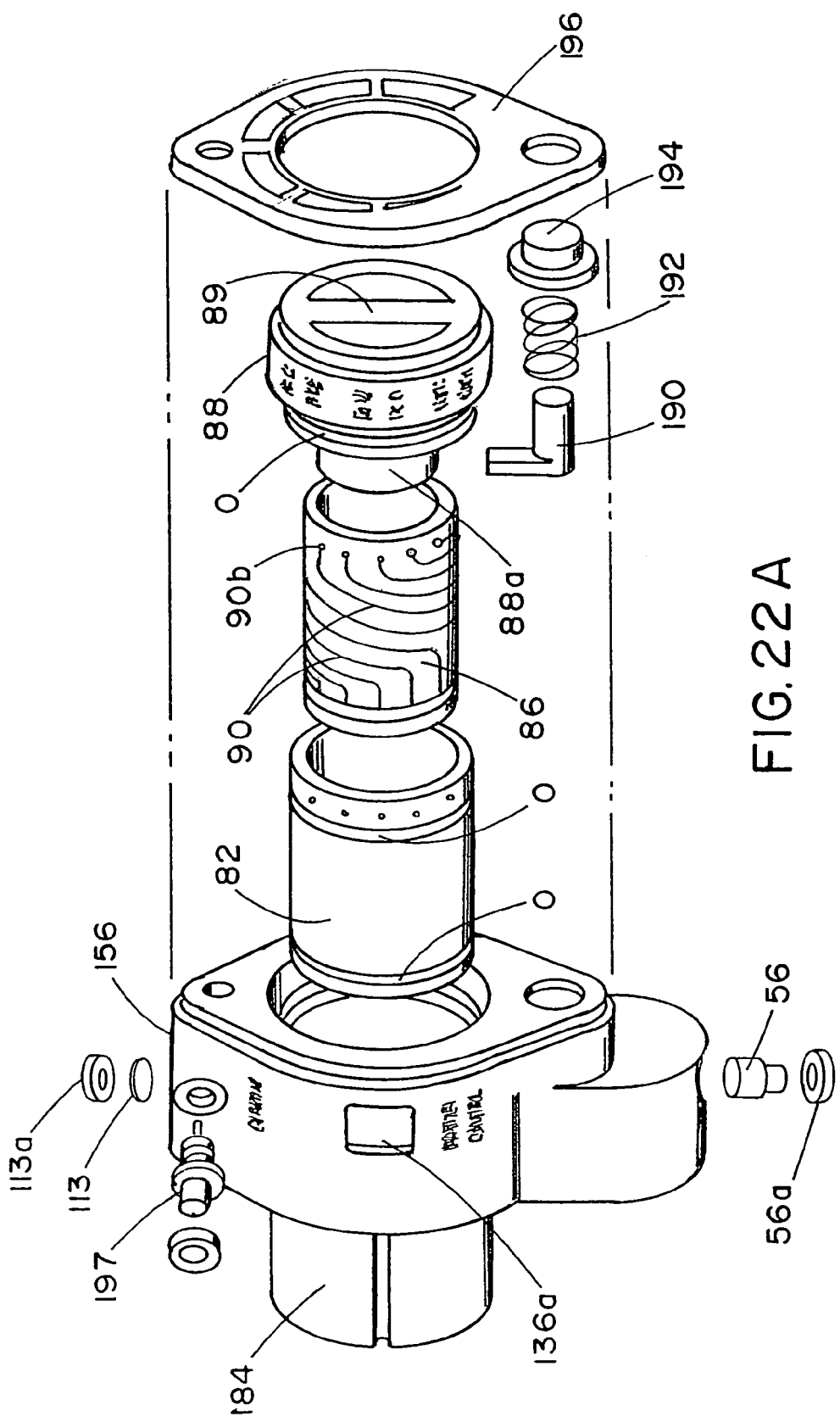
FIG. 22A is a generally perspective exploded view of the apparatus shown in FIG. 22.
Figure 31:
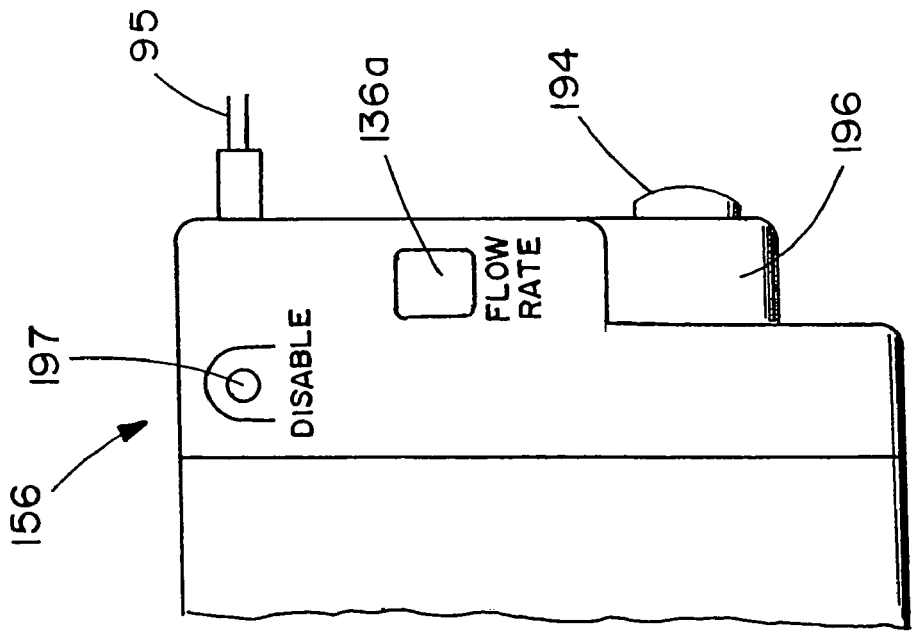
FIG. 31 is a fragmentary side elevational view of the forward portion of the alternate form of the apparatus shown in FIG. 19.

After opening of cover 160*a* (FIG. 22), vial 172 can be inserted into chamber 174. As the fill vial is so introduced and the plunger 104 is threadably interconnected with end 175 of the elongated support, the sharp end of elongated needle 180 will pierce the central wall 104*a* of the elastomeric plunger. Continuous movement of the vial into chamber 174 will cause the structural support 178 to move the elastomeric plunger inwardly of the vial chamber in a direction toward the second closed end 100*b* of the vial. As the plunger is moved inwardly of the vial, the fluid contained within the vial chamber will be expelled therefrom into the hollow elongated needle 180. As best seen in FIG. 22, the fluid will then flow past umbrella type check valve 182 and into passageway 171 formed in third portion 160 of the apparatus housing.

As the fluid flows into the bellows reservoir, the bellows will be expanded from the collapsed configuration shown in FIG. 22 into an expanded configuration. As the bellows member expands it will urge a telescopically movable volume indicator member 112 that is carried within second portion of the housing and in engagement with the stored energy source, or compressible-expandable member 170 causing it to compress. It is also to be understood that, if desired, the reservoir of the bellows component can also be filled by alternate filling means of the character previously described which comprises a syringe having a needle adapted to pierce the pierceable septum 56 which is mounted within third portion 160 of the apparatus housing. As the reservoir 164 fills with fluid either from the fill vial 172 or from the filling syringe, any gases trapped within the reservoir will be vented to atmosphere via vent means "V" which comprises the earlier described gas vent 113.

Upon opening the fluid delivery path to the administration set 94 in a manner presently to be described, the stored energy means, or member 170, will tend to return to its less compressed starting configuration thereby controllably urging fluid flow outwardly of reservoir 164 via passageway 185 and the flow control means of the invention. As the fluid contained within the bellows reservoir 164 is urged outwardly thereof by the stored energy means, the fluid will flow into a fluid passageway 185 formed in the first portion 184a of ullage member 184. The fluid will then flow under pressure through a filter means shown here as a filter 116 that is identical to that previously described. After flowing through filter 116, the fluid will flow, via a stub passageway 185a (FIG. 22) into the several radially outwardly extending flow passageways 120 formed in flow control member 86. The filtered fluid will fill passageways 120 and then will flow into the plurality of spiral passageways 90 formed in member 86 via outlets 90b, which communicate with passageways 120 (see FIG. 10). The fluid contained within spiral passageways 90 can flow outwardly of the device only when one of the fluid outlets 84 formed in casing 82 is aligned with a passageway 186 formed in the ullage member.

Selection of the passageway 90 from which the fluid is to be dispensed is accomplished by rotation of the selector knob 88 in the manner previously described in connection with the embodiment shown in FIGS. 1 through 18. The construction and operation of the selector knob is identical to that previously described and will not be re-described at this time.

As illustrated in FIGS. 22 and 28, as before, the distal portion of selector knob 88 is provided with a plurality of circumferentially spaced apart indexing cavities 88c that closely receive an indexing finger 190 which forms a part of the indexing means of this latest form of the invention which is carried within third portion 160 of the apparatus housing. Indexing finger 190 is continuously urged into engagement with a selected one of the indexing cavities 88c by a coil spring 192 that also forms a part of the indexing means of the invention. Coil spring 192 can be compressed by an inward force exerted on an indexing shaft 194 that is received within front retaining plate 196 and is movable from the extended position shown in FIG. 22 to an inward, finger release position wherein spring 192 is compressed and finger 190 is retracted from a selected indexing cavity 88c. With finger 190 in its retracted position it is apparent that control knob 88 can be freely rotated to a position wherein flow rate indicia 134 formed on the periphery of knob 88 can be viewed through a viewing window 136a formed in the housing. Button 197 disables (stops the flow) to the dispenser line.

When the selector knob 88 is in the desired position and pressure is released on indexing shaft 194, finger 190 of the indexing means of the invention will move into locking engagement with one of the indexing cavities 88c thereby placing a selected one of the spiral shaped flow control channels 90 in communication with outlet 186 of the fluid reservoir 164. As the fluid flows outwardly of the apparatus due to the urging of the stored energy means or elastomeric member 170, the bellows structure 162 will be collapsed and at the same time member 112 will travel inwardly of housing portion 158 and will provide an indication of the volume of fluid remaining in the fluid reservoir in the same manner as earlier described.

Figure 30:
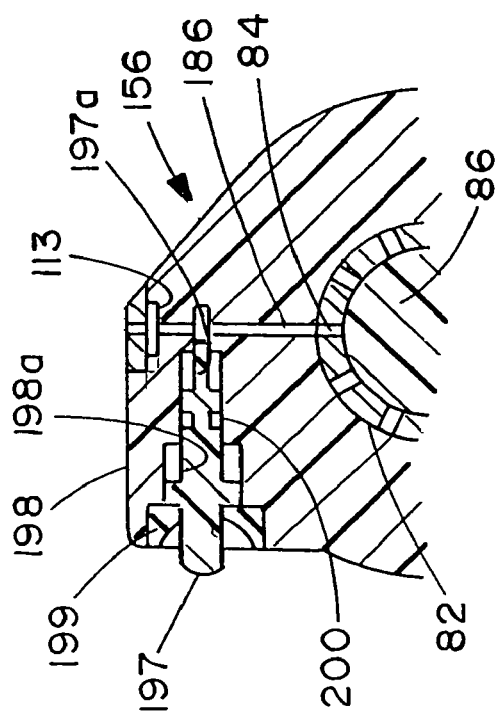
FIG. 30 is a cross-sectional view taken along lines 30-30 of FIG. 22.

The apparatus of this latest form of the invention also includes novel safety disabling means for disabling the apparatus. As best seen in FIGS. 19 and 30, the disabling means here comprises a disable shaft 197 that is telescopically movable within a passageway 198a formed in a housing 198 that forms a part of portion 156 of the outer housing of the apparatus. Shaft 197 includes a distal end 197a, which, upon insertion of shaft 197 inwardly of passageway 198a, will block fluid flow through passageway 186 and outwardly into the fluid dispensing means. A retainer 199 normally holds shaft 197 is the retracted position and an elastomeric O-ring 200 carried by shaft 197 prevents fluid leakage past the shaft.

Referring now to FIGS. 32 through 42, still another embodiment of the dispensing apparatus of the present invention is there illustrated and generally designated by the numeral 202. This alternate form of the apparatus of the invention is similar in many respects to that shown in FIGS. 19 through 31 and like numerals are used in FIGS. 32 through 42 to identify like components. The primary difference between this latest form of the invention and the invention shown in FIGS. 19 through 31 resides in the fact that the fill vial used to fill the fluid reservoir is of different construction. As best seen in FIGS. 32 through 36, the apparatus of this alternate form of the invention comprises an outer housing 202 having mechanically engaged or suitably bonded together first, second and third portions 206, 208 and 210 respectively. Disposed within outer housing 206 is an inner, expandable housing 162 that is of identical construction and operation to the expandable housing of the last described embodiment of the invention. Housing 162 includes a fluid reservoir 164 that is provided with an inlet 166 (FIG. 37) for permitting fluid flow into the fluid reservoir. As before, expandable housing 162 comprises a bellows structure having an expandable and compressible, accordion like sidewall 162a of the character best seen in FIG. 37.

Disposed within second portion 208 of outer housing 202 is the stored energy means of the invention for acting upon inner expandable housing 162 in a manner to cause the fluid contained within fluid reservoir 164 to controllably flow through outlet 185. In this alternate form of the invention, the important stored energy means is identical in construction and operation to that earlier described in stored energy means and here comprises a compressively deformable, elastomeric member 170 that is carried within the second portion 208 of the outer housing. As before, in operation member 170 is first compressed by fluid flowing into reservoir 164 and then is controllably expanded to cause fluid flow from the fluid reservoir.

Figure 32:
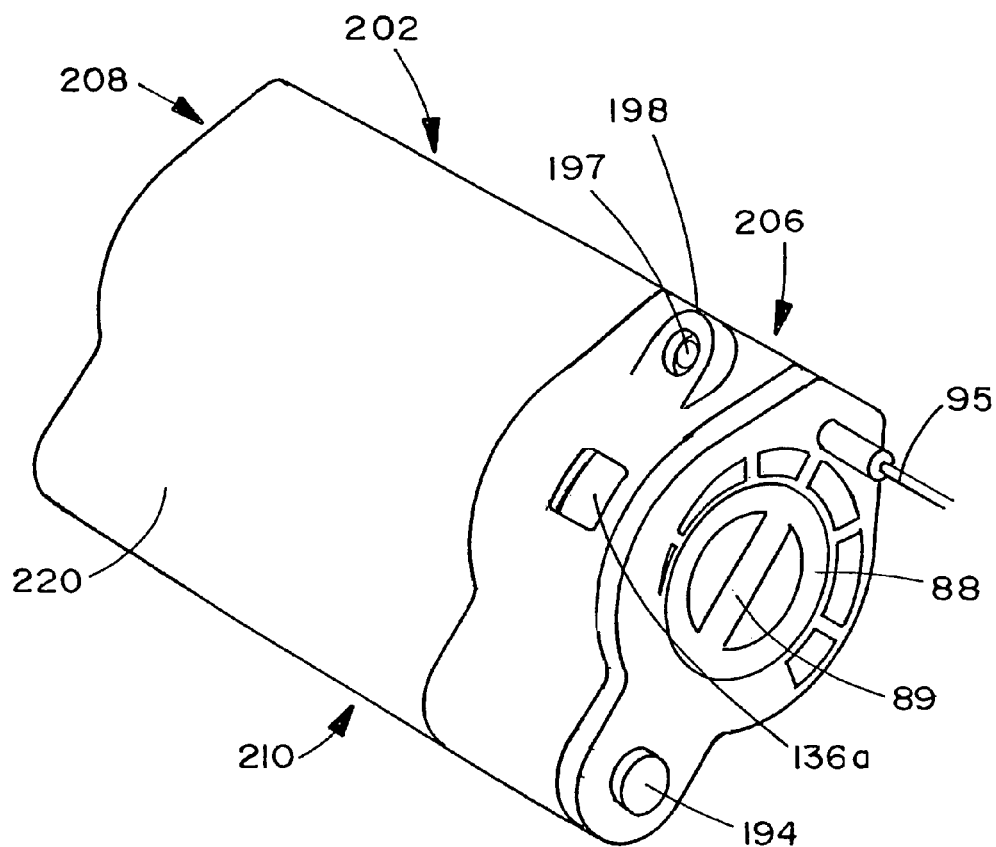
FIG. 32 is a generally perspective view of still another embodiment of the fluid delivery apparatus of the present invention for dispensing fluids at a uniform rate.
Figure 32A:
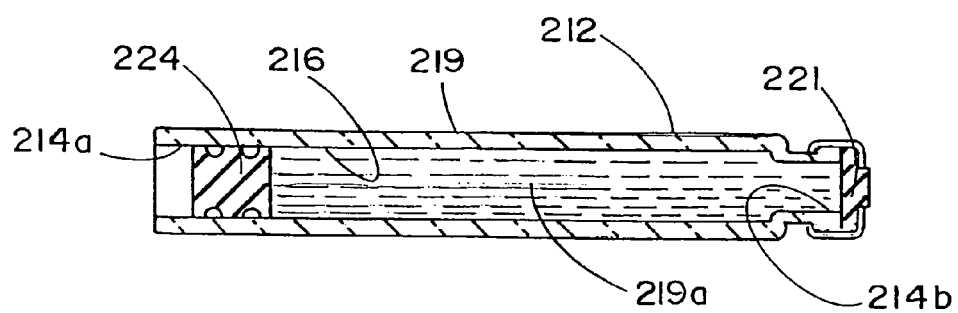
FIG. 32A is a cross-sectional view of the fill vial assembly of the form of the invention shown in FIG. 32.
Figure 36:
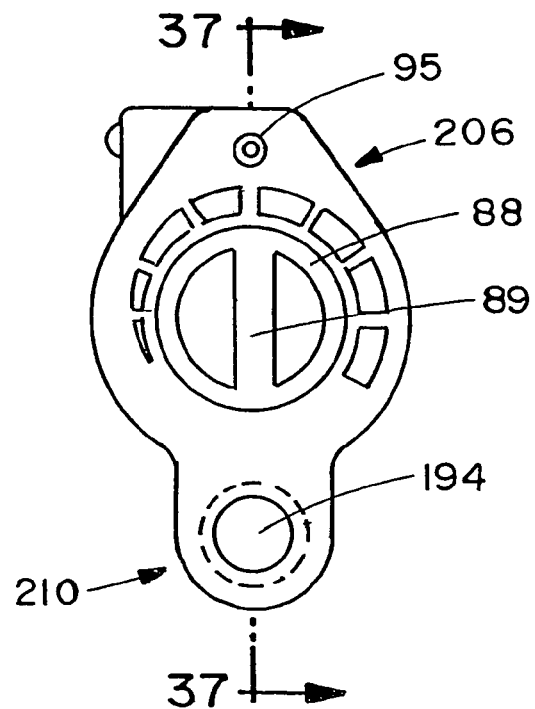
FIG. 36 is a right-end view of the apparatus shown in FIG. 37.
Figure 38:
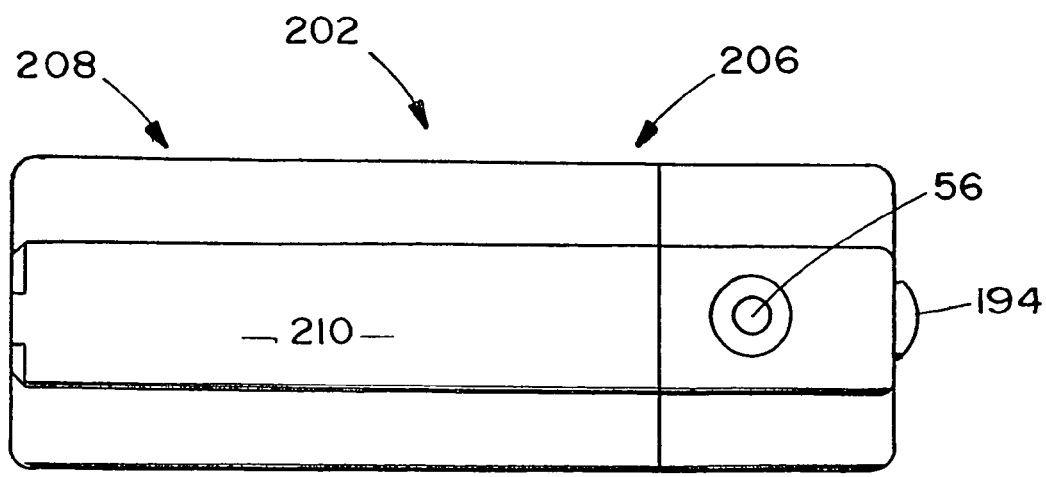
FIG. 38 is a bottom plan view of the alternate form of the apparatus shown in FIG. 32.

As in the last described embodiment of the invention, the apparatus of this alternate form of the invention comprises fill means carried by the third portion 210 of outer housing 202 for filling the reservoir 164 with the fluid to be dispensed. This fill means is also similar to the earlier described fill means, save for the fact that the fill means of this latest embodiment comprises a single cartridge fill vial 212 which is of a slightly different construction and operation from closed-end shell fill vial 172 (see FIG. 32A). As before, the fill means also includes an alternate fill and drug recovery means that comprises a pierceable septum 56 that is disposed within a cavity 54 formed in the third portion 210 of outer housing 202. Septum 56 is pierceable by the needle of the syringe which contains the medicinal fluid to be dispensed and which can be used to fill or partially fill reservoir 164 via a passageway 171 formed in third portion 210.

Figure 37:
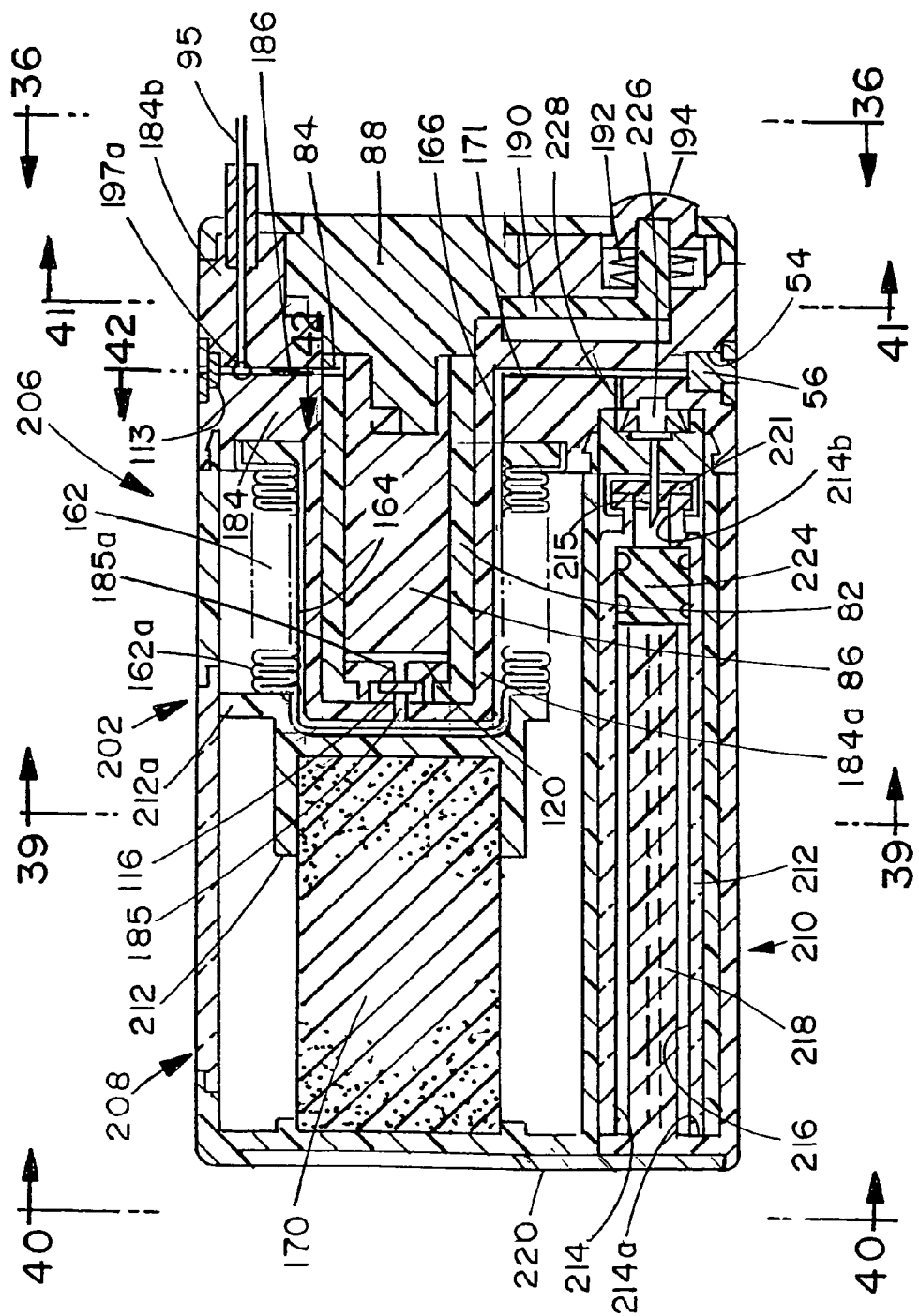
FIG. 37 is cross-sectional view taken along lines 37-37 of FIG. 36.

As best seen in FIG. 37, third portion 210 of housing 202 includes a chamber 214 for telescopically receiving the medicament containing fill cartridge vial 212. As shown in FIG. 34, an elongated support 218 is mounted within a hollow vial cover 220 that removably covers the fill vial in the manner shown in FIG. 37. The purpose of elongated support 218 will presently be described. Fill vial cartridge 212, which is of the generally conventional construction shown in FIG. 32A, comprises a hollow glass or plastic body portion 219 having an inner surface 216 that defines a fluid chamber 219a. The fill cartridge vial has an open first end 214a and a second end 214b that is closed by a pierceable, elastomeric septum 221 secured in place by a conventional crimp closure means (see FIG. 32A). Mounted proximate the inboard end of chamber 214 of housing 202 is a hollow needle 215 (FIG. 37) which is adapted to pierce septum 221 when the fill vial is inserted into chamber 214 in a manner next to be described.

Disposed within fluid reservoir 219a is a plunger 224 that is moved by support 218 of vial cover 220 from a first position proximate end 214a of vial 212 to a second position shown in FIG. 37. More particularly, as the vial cover 220 is mated with the apparatus housing, the inboard 218a of elongated support 218 engages plunger 224 urging the plunger inwardly of fluid chamber 219a (see FIGS. 34 and 32A). As the plunger moves inwardly of the fluid reservoir, the fluid contained in the reservoir will be forced through hollow needle 215, passed an umbrella check valve 226 mounted within third portion 210, into a stub passageway 228, into passageway 171 and finally into fluid reservoir 164. As the fluid flows into reservoir 164 it will compress the stored energy means in the manner previously described.

The apparatus of this latest form of the invention also includes flow control means that is identical in construction and operation to the flow control means described in connection with the embodiment of the invention shown in FIGS. 18 through 31. This flow control means is connected to first portion 206 of outer housing 202 and comprises an ullage defining member 184 having a first portion 184a disposed within inner, expandable housing 162 and a second portion 184b having a fluid passageway 186 that is in communication with the outlet of the fluid reservoir 164

As before, the flow control means includes a flow control subassembly that is substantially identical in construction and operation to the earlier described flow control subassembly 80 and is of the configuration shown in FIGS. 9, 10, 12 and 13 of the drawings. For this reason, the details of the construction and operation of the control means of this latest embodiment of the invention will not be here repeated and reference should be made to the earlier description of the flow control subassembly 80.

Turning once again to FIG. 32, also forming a part of the fluid dispensing apparatus of this latest form of the invention is dispensing means for dispensing fluid to the patient. This dispensing means is identical in construction and operation to the previously identified administration set 94 and is connected to the first portion 206 of housing 202.

Upon opening the fluid delivery path to the administration set 94 in a manner presently to be described, the stored energy means, or member 170, will tend to return to its less compressed starting configuration thereby controllably urging fluid flow outwardly of reservoir 164 via the flow control means of the invention. As the fluid contained within the bellows reservoir 164 is urged outwardly thereof by the stored energy means, the fluid will flow into a fluid passageway 185 formed in the first portion 184a of ullage member 184. The fluid will then flow under pressure through a filter means shown here as a filter 116 that is identical to that previously described. After flowing through filter 116, the fluid will flow, via a stub passageway 185a (FIG. 37) into the several radially outwardly extending flow passageways 120 formed in flow control member 86. The filtered fluid will fill passageways 120 and then will flow into the plurality of spiral passageways 90 formed in member 86 via outlets 90b, which communicate with passageways 120 (see FIG. 10). The fluid contained within spiral passageways 90 can flow outwardly of the device only when one of the fluid outlets 84 formed in casing 82 is aligned with passageway 186 (FIG. 37).

Selection of the passageway 90 from which the fluid is to be dispensed is accomplished by rotation of the selector knob 88 in the manner previously described in connection with the embodiment shown in FIGS. 19 through 31. The construction and operation of the selector knob, the indexing means and the locking means is identical to that previously described and will not be re-described at this time.

As in the earlier described embodiments of the invention, as the fluid flows outwardly of the apparatus due to the urging of the stored energy means or elastomeric member 170, the bellows structure 162 will be collapsed and at the same time member 212 will travel inwardly of housing portion 208 and will provide an indication of the volume of fluid remaining in the fluid reservoir in the same manner as earlier described.

This latest embodiment also includes disabling means, which, as shown in FIG. 42, is substantially identical in construction and operation to that previously described.

Figure 43:
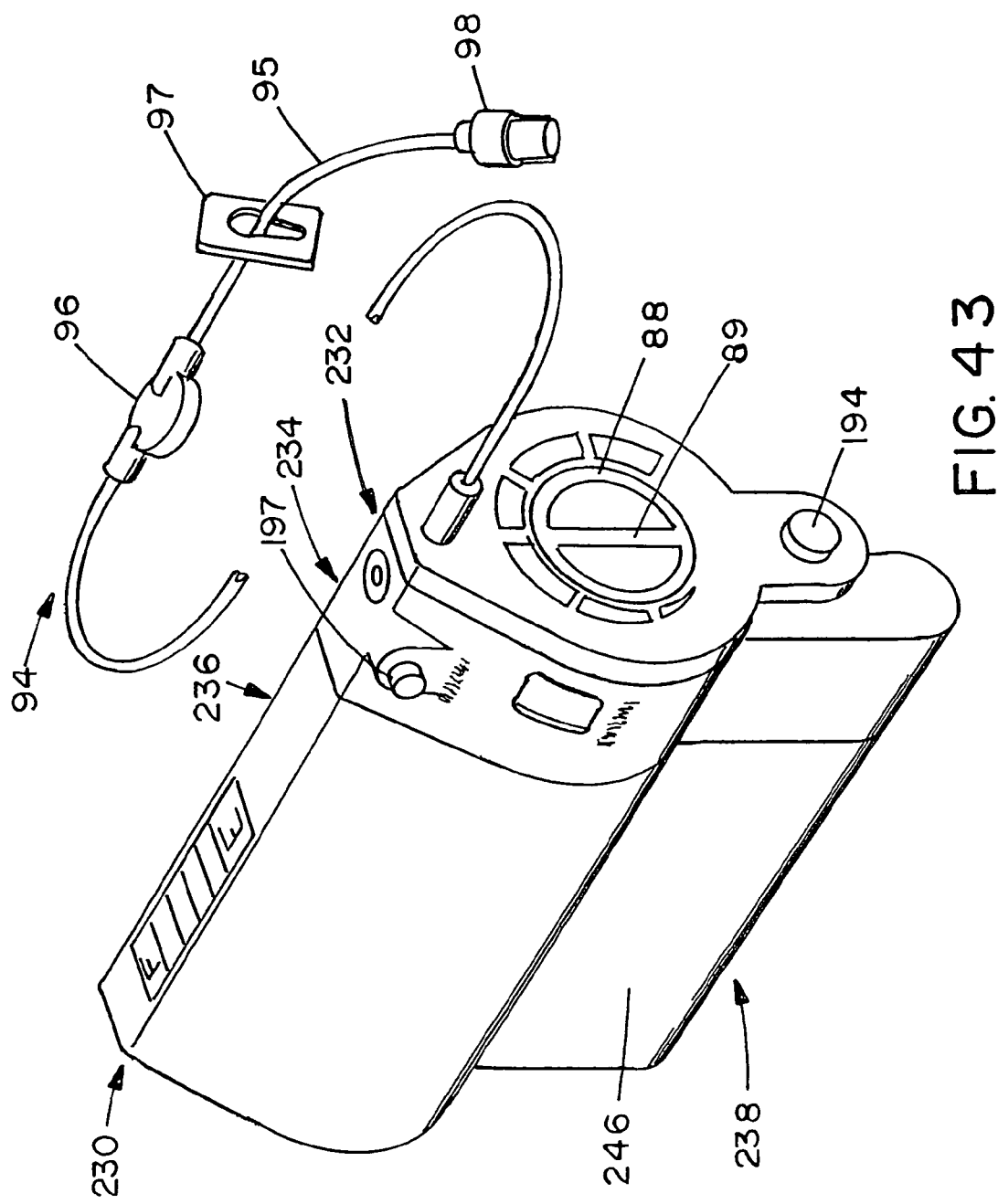
FIG. 43 is a generally perspective view of yet another embodiment of the fluid delivery apparatus of the present invention for dispensing fluids at a uniform rate.
Figure 44:
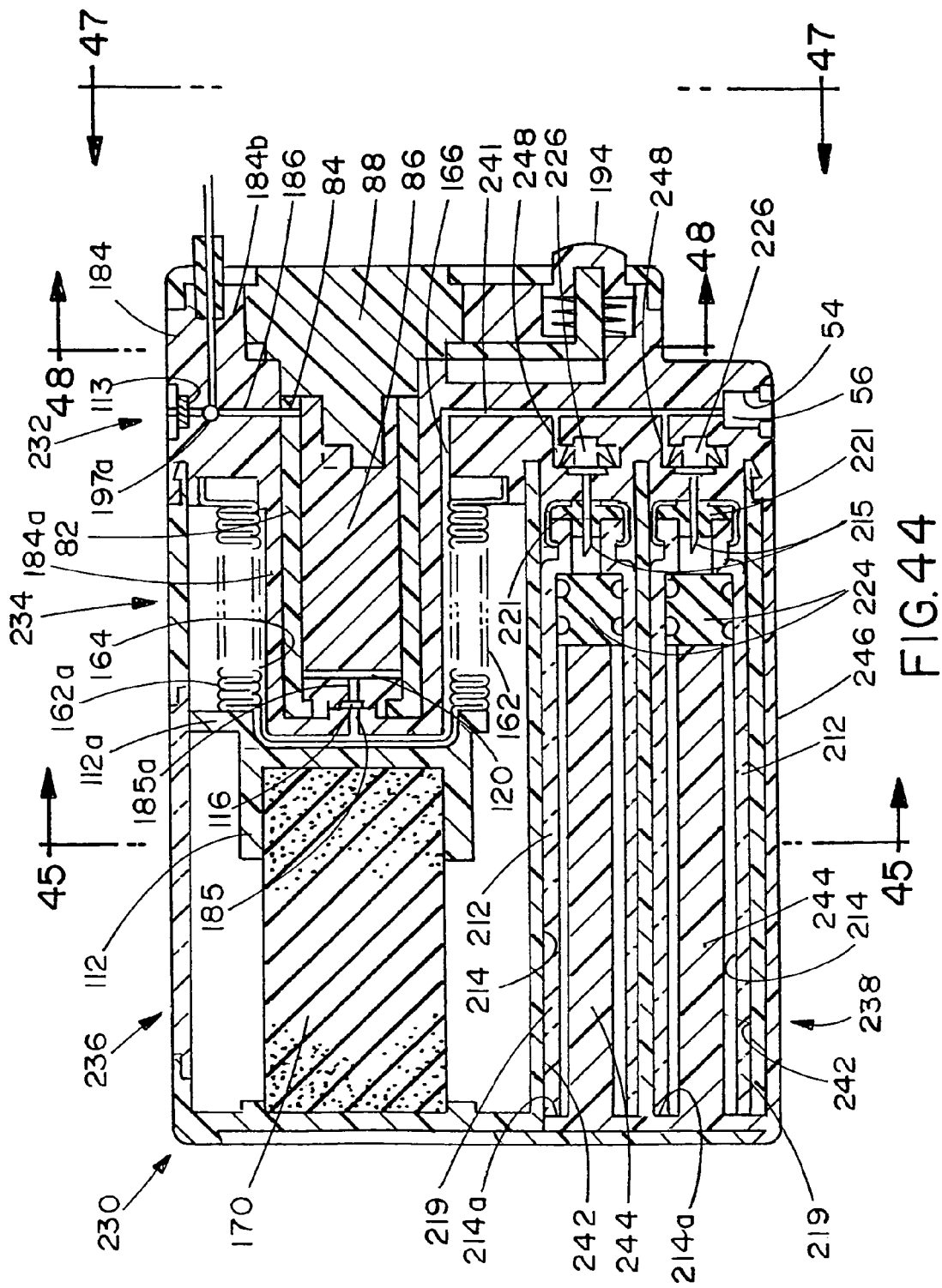
FIG. 44 is an enlarged longitudinal cross-sectional view of the embodiment of the invention shown in FIG. 43.
Figure 45:
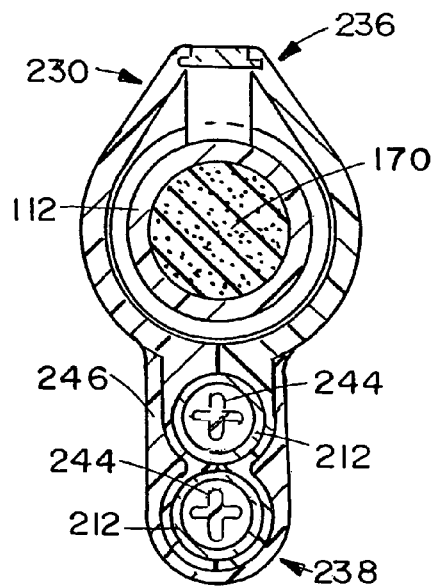
FIG. 45 is a cross-sectional view taken along lines 45-45 of FIG. 44.
Figure 46:
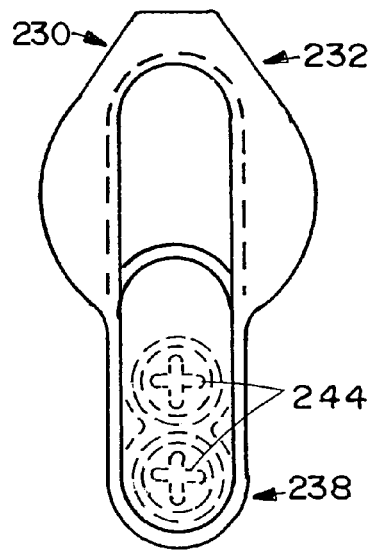
FIG. 46 is a left-end view of the apparatus shown in FIG. 44.
Figure 47:
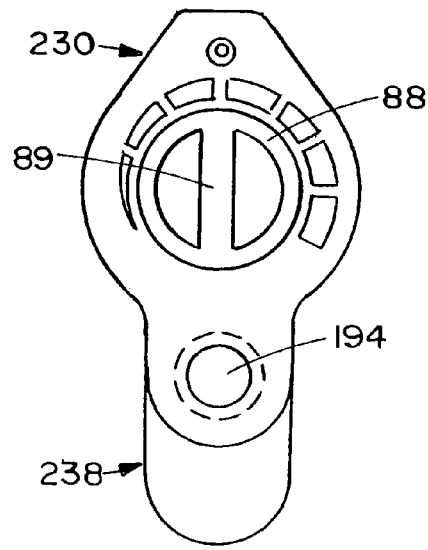
FIG. 47 is view taken along lines 47-47 of FIG. 44.
Figure 48:
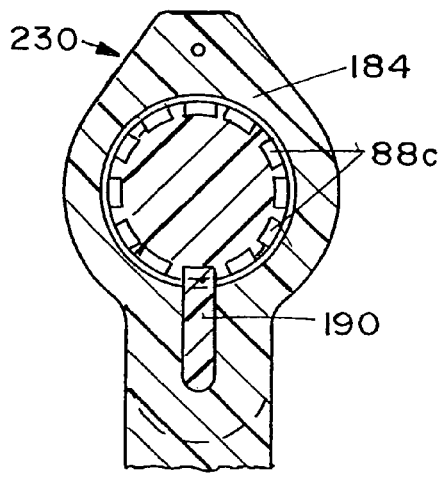
FIG. 48 is a cross-sectional view taken along lines 48-48 of FIG. 44.

Referring now to FIGS. 43 through 50, yet another embodiment of the dispensing apparatus of the present invention is there illustrated and generally designated by the numeral 230. This alternate form of the apparatus of the invention is similar in many respects to that shown in FIGS. 32 through 34 and like numerals are used in FIGS. 43 through 50 to identify like components. The primary difference between this latest form of the invention and the invention shown in FIGS. 32 through 42 resides in the fact that two fill vials are used to fill the fluid reservoir of the apparatus. As before, the apparatus of this alternate form of the invention comprises an outer housing 232 having a first, second and third portions 234, 236, and 238 respectively. Disposed within outer housing 232 is an inner, expandable housing 162 that is of identical construction and operation to the expandable housing of the embodiment of the invention shown in FIGS. 32 through 42. As in the earlier described embodiment, housing 162 includes a fluid reservoir 164 that is provided with an inlet 166 (FIG. 44) for permitting fluid flow into the fluid reservoir. As shown in FIG. 44, expandable housing 162 comprises a bellows structure having an expandable and compressible, accordion-like side wall 162a.

Disposed within second portion 236 of outer housing 232 is the stored energy means of the invention for acting upon inner expandable housing 162 in a manner to cause the fluid contained within fluid reservoir 164 to controllably flow through outlet 186. In this alternate form of the invention, the important stored energy means is identical in construction and operation to the earlier described stored energy means and here comprises a compressively deformable, elastomeric member 170 that is carried within the second portion 236 of the outer housing. As before, in operation member 170 is first compressed by fluid flowing into reservoir 164 and then is controllably expanded to cause fluid flow from the fluid reservoir.

As in the last described embodiment of the invention, the apparatus of this alternate form of the invention comprises fill means carried by the third portion 238 of outer housing 232 for filling the reservoir 164 with the fluid to be dispensed. This fill means is also similar to the earlier described fill means, save for the fact that the fill means of this latest embodiment comprises a pair of identical fill vials or cartridges 212 which are of the same construction and operation as the earlier described fill vial 212. As in the previously described embodiments, the fill means also includes an alternate fill means that comprises a pierceable septum 56 that is disposed within a cavity 54 formed in the third portion 238 of outer housing 232. Septum 56 is pierceable by the needle of the syringe which contains the medicinal fluid to be dispensed and which can be used to fill or partially fill reservoir 164 via a passageway 241 formed in third portion 238.

As best seen in FIGS. 44 and 50, third portion 238 of housing 232 includes a pair of spaced-apart chambers 242 for telescopically receiving the medicament containing fill vials 212. As shown in FIGS. 43, 44, and 50, a pair of elongated supports 244 are mounted within a hollow vial cover 246 that forms a part of the third portion 238 of the housing and removably covers the fill vials in the manner shown in FIG. 44. Each of the fill vial cartridges 212 has a generally conventional construction, shown in FIGS. 49 and 49A, and each comprises a hollow glass or plastic body portion 219 that defines a fluid chamber 220. Each fill vial has an open first end 214a and a second end that is closed by a pierceable, elastomeric septum 221. Mounted proximate the inboard end of each chamber of the housing is a hollow needle 215 which is adapted to pierce septum 221 when the fill vials are inserted into chambers 242 in a manner next to be described.

Disposed within each fluid reservoir 220 is a plunger 224 that is moved by a support 244 of vial cover 246 from a first position proximate end 214a of the vial to a second position. More particularly, as the vial cover 246 is slidably mated with the apparatus housing, the inboard of each of the elongated supports engages a plunger 224 urging the plunger inwardly of fluid chamber 220. As each of the plungers move inwardly of their respective fluid reservoirs, the fluid contained in the reservoir will be forced through hollow needle 215, passed an umbrella check valve 226 mounted within third housing portion 238, into a stub passageway 248, into passageway 241 and finally into fluid reservoir 164 via 166. As the fluid flows into reservoir 164, it will compress the stored energy means in the manner previously described.

The apparatus of this latest form of the invention also includes flow control means that is identical in construction and operation to the flow control means described in connection with the embodiment of the invention shown in FIGS. 32 through 42. This flow control means is connected to first portion 234 of outer housing 232 and comprises an ullage defining member 184 having a first portion 184a disposed within inner, expandable housing 162 and a second portion 184b having a fluid passageway 186 that is in communication with the outlet of the fluid reservoir 164.

As before, the flow control means includes a flow control subassembly that is substantially identical in construction and operation to the earlier described flow control subassembly 80 and is of the configuration shown in FIGS. 9, 10, 12 and 13 of the drawings. For this reason, the details of the construction and operation of the control means of this latest embodiment of the invention will not be here repeated and reference should be made to the earlier description of the flow control subassembly 80.

Turning once again to FIG. 43, also forming a part of the fluid dispensing apparatus of this latest form of the invention is dispensing means for dispensing fluid to the patient. This dispensing means is identical in construction and operation to the previously identified administration set 94 and is connected to the first portion 234 of housing 232.

Upon opening the fluid delivery path to the administration set 94, the stored energy means, or member 170, will tend to return to its less compressed starting configuration thereby controllably urging fluid flow outwardly of reservoir 164 via the flow control means of the invention. As the fluid contained within the bellows reservoir 164 is urged outwardly thereof by the stored energy means, the fluid will flow into a fluid passageway 185 formed in the first portion 184a of ullage member 184. The fluid will then flow under pressure through a filter means shown here as a filter 116 that is identical to that previously described. After flowing through filter 116, the fluid will flow, via a stub passageway 185a (FIG. 44) in the several radially outwardly extending flow passageways 120 formed in flow control member 86. The filtered fluid will fill passageways 120 and then will flow into the plurality of spiral passageways 90 formed in member 86 via outlets 90b, which communicate with passageways 120 (see FIG. 10). The fluid contained within spiral passageways 90 can flow outwardly of the device only when one of the fluid outlets 84 formed in casing 82 is aligned with passageway 186 (FIG. 44).

Selection of the passageway 90 from which the fluid is to be dispensed is accomplished by rotation of the selector knob 88 in the manner previously described in connection with the embodiment shown in FIGS. 19 through 31. The construction and operation of the selector knob, the indexing means and the locking means is identical to that previously described and will not be re-described at this time.

As in the earlier described embodiment of the invention, as the fluid flows outwardly of the apparatus due to the urging of the stored energy means or elastomeric member 170, the bellows structure 162 will be collapsed and at the same time member 112 will travel inwardly of housing portion 236 and will provide an indication of the volume of fluid remaining in the fluid reservoir in the same manner as earlier described.

This latest embodiment also includes a safety defeat disabling means, which is substantially identical in construction and operation to that previously described.

Turning now to FIGS. 51 through 63, another form of the dispensing apparatus of the present invention is there illustrated and generally designated by the numeral 250. This alternate form of the apparatus of the invention is similar in many respects to that shown in FIGS. 43 through 50 and like numerals are used in FIGS. 51 through 63 to identify like components. The primary difference between this latest form of the invention and the invention shown in FIGS. 43 through 50 resides in the fact that one of the two cartridge fill vials used to fill the fluid reservoir of the apparatus is of a different construction. More particularly, one of the fill vials is specially designed to enable the reconstitution and intermixing of a lyophilized drug with a suitable diluent prior to the delivery of the mixture to the fluid reservoir of the device.

Figure 52:
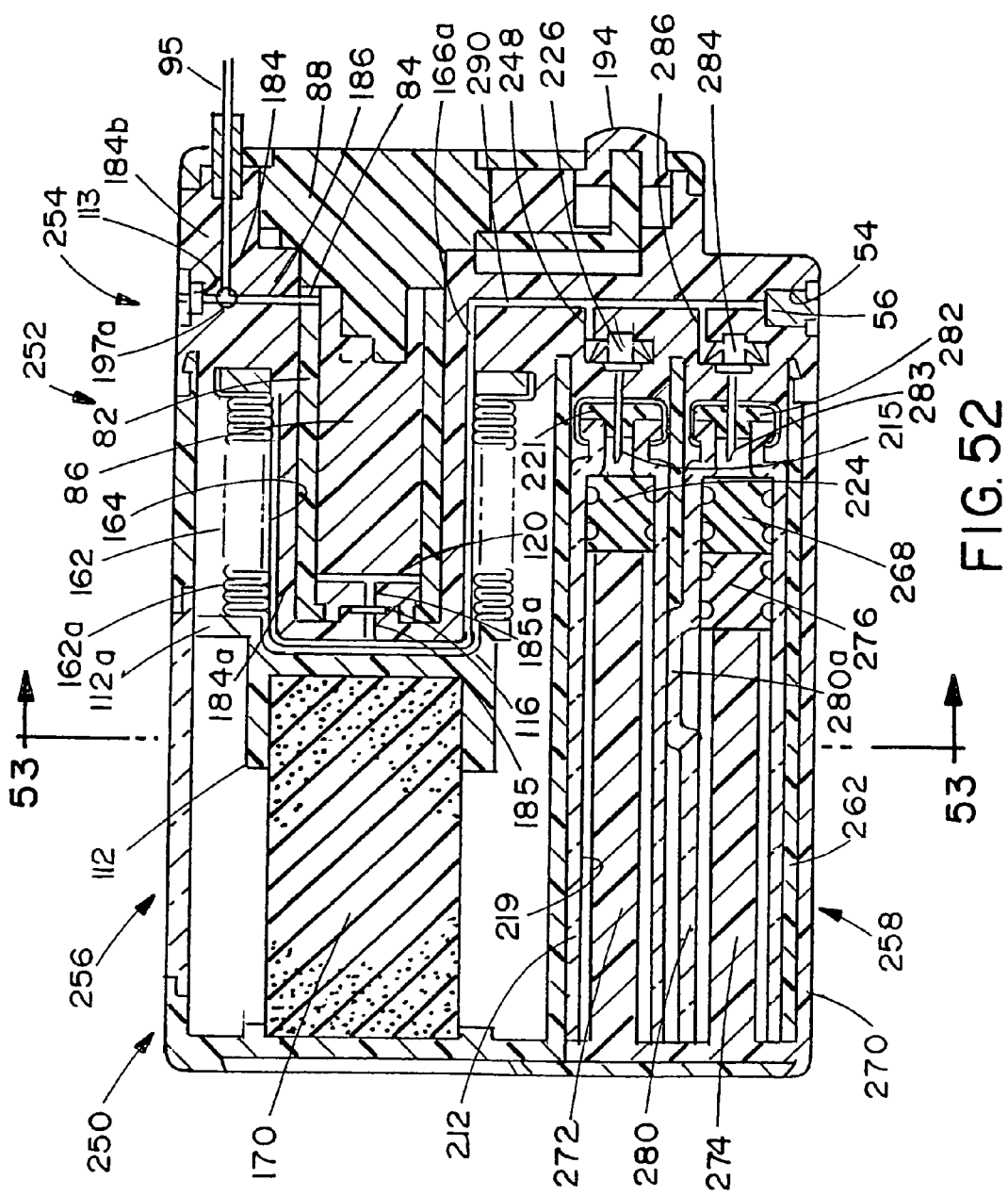
FIG. 52 is an enlarged longitudinal cross-sectional view of the embodiment of the invention shown in FIG. 51.
Figure 63:
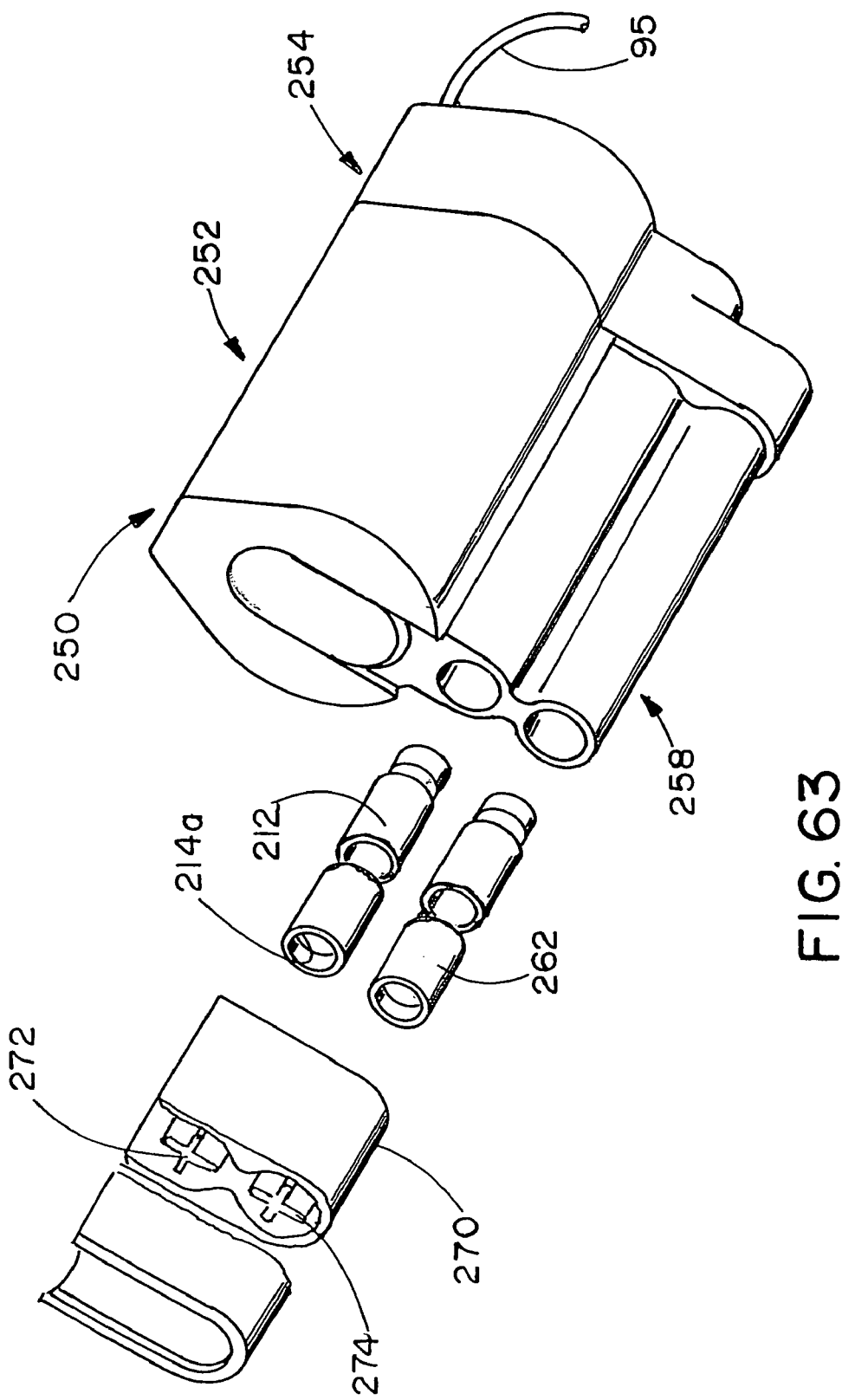
FIG. 63 is a generally perspective exploded view of the embodiment shown in FIG. 51.
Figure 67:
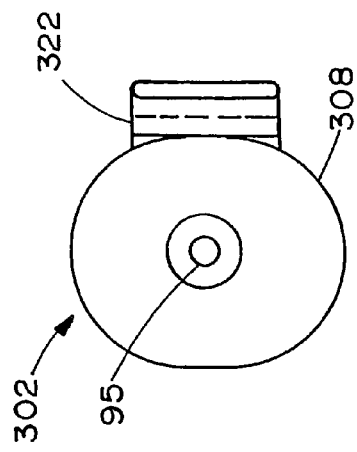
FIG. 67 is a right-end view of the apparatus shown in FIG. 66.
Figure 65:
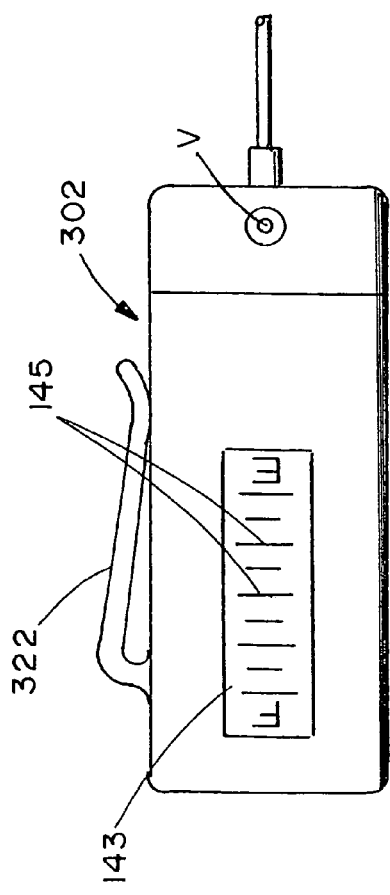
FIG. 65 is a top plan view of the embodiment of the invention shown in FIG. 64.

As in the earlier described embodiments, the apparatus of this latest form of the invention comprises an outer housing 252 having first, second and third portions 254, 256 and 258 respectively. Disposed within outer housing 252 is an inner, expandable housing 162 that is of identical construction and operation to the expandable housing of the embodiment of the invention shown in FIGS. 32 through 42. As in the earlier described embodiment, housing 162 includes a fluid reservoir 164 that is provided with an inlet 166a (FIG. 52) for permitting fluid flow into the fluid reservoir. As shown in FIG. 52, expandable housing 162 comprises a bellows structure having an expandable and compressible, accordion like sidewall 162a.

Disposed within second portion 256 of outer housing 252 is the stored energy means of the invention for acting upon inner expandable housing 162 in a manner to cause the fluid contained within fluid reservoir 164 to controllably flow through outlet 186. In this latest form of the invention, the important stored energy means is identical in construction and operation to the earlier described stored energy means and here comprises a compressively deformable, elastomeric member 170 that is carried within the second portion 256 of the outer housing. As before, in operation, member 170 is further compressed by fluid flowing into reservoir 164 and then is controllably expanded to cause fluid flow from the fluid reservoir.

As previously mentioned, the apparatus of this latest form of the invention comprises fill means of a somewhat different construction that is carried by the third portion 258 of outer housing 252 for filling the reservoir 164 with the fluid to be dispensed. This fill means, like the last described fill means, comprises a pair of fill vials or cartridges one of which, namely fill vial 212, is of identical construction and operation to the earlier described fill vial 212. The second fill vial or cartridge designated by the numeral 262 comprises a container of special design that uniquely contains a lyophilized drug 264 that is separated from a reconstituting fluid 266 by a barrier stopper 268 (FIG. 57). Lyophilized drug 264 can, by way of example, comprise anti-infectives, oncolytics, cardiac drugs or various other types of beneficial agents. Cartridge 262 is telescopically receivable within a vial housing 270 that is of the configuration shown in FIGS. 52, 55 and 56. As before, vial housing 270 includes a pair of spaced apart pusher members 272 and 274 which, upon mating of the vial housing within the apparatus housing, engage plungers 224 (FIG. 59) and 276 (FIG. 57) respectively to push them forwardly of their respective container reservoirs.

Considering in more detail the reconstitution cartridge assembly 262, as best seen in FIG. 57, this cartridge assembly includes a vial 280 that is sealed at one end by a plunger 276 and at the other end by a pierceable septum 282 (FIGS. 54 57, and 61). Formed intermediate the ends of vial 280 is a raised outer wall portion 280a which permits fluid 266 to bypass barrier stopper 268 as the elastomeric barrier stopper is urged inwardly of the container by pressure exerted thereon by the fluid 266. Fluid 266 exerts pressure on barrier member 268 as a result of pusher member 274 exerting inward pressure on plunger 276, which pressure is, in turn, caused by the inward movement of plunger 276 as vial housing 262 is mated with the apparatus housing 270 (FIG. 52).

A continued inward pressure exerted on elastomeric plunger 276 will cause the reconstitution agent 266 to flow past barrier stopper member 268 via wall portion 280a or the bypass chamber, so as to reconstitute lyophilized drug 264. Further pressure exerted on plunger 276 will cause the reconstituted drug formed by the fluid 266 which has been intermixed with drug 264 to flow through a hollow cannula 215, past check valve 284, into a stub passageway 286 then into a passageway 290 then into microgrooves 166a formed in ullage 184a and finally into reservoir 164 (FIG. 52).

As previously mentioned, plunger 224 is disposed within vial 212 and is moved by a support 272 of vial cover 270 as the vial cover is slidably mated with the apparatus housing. As plunger 224 is moved inwardly of fluid reservoir 219, the diluent contained in the reservoir will be forced through hollow needle 215, passed an umbrella check valve 226 mounted within third housing portion 258, into a stub passageway 248, into passageway 290, into micro-channels 166a and finally into fluid reservoir 164. As the fluid flows into reservoir 164, it will compress the stored energy means in the manner previously described.

As in the earlier described embodiments, the fill means also includes an alternate fill and recovery means that comprises a pierceable septum 56 that is disposed within a cavity 54 formed in the third portion 258 of outer housing 252. Septum 56 is pierceable by the needle of the syringe which contains the medicinal fluid to be dispensed and which can be used to fill or partially fill reservoir 164 via a passageway 290 formed in third portion 258.

The apparatus of this latest form of the invention also includes flow control means that is identical in construction and operation to the flow control means described in connection with the embodiment of the invention shown in FIGS. 32 through 42. This flow control means is connected to first portion 254 of outer housing 252 and comprises an ullage defining member 184 having a first portion 184a disposed within inner, expandable housing 162 and a second portion 184b having a fluid passageway 186 that is in communication with outlet 168 of the fluid reservoir 164

As before, the flow control means includes a flow control subassembly that is substantially identical in construction and operation to the earlier described flow control subassembly 80 and is of the configuration shown in FIGS. 9, 10, 12 and 13 of the drawings. For this reason, the details of the construction and operation of the control means of this latest embodiment of the invention will not be here repeated and reference should be made to the earlier description of the flow control subassembly 80.

Turning once again to FIG. 51, also forming a part of the fluid dispensing apparatus of this latest form of the invention is dispensing means for dispensing fluid to the patient. This dispensing means is identical in construction and operation to the previously identified administration set 94 and is connected to the first portion 254 of housing 252.

Upon opening the fluid delivery path to the administration set 94 in a manner presently to be described, the stored energy means, or member 170, will tend to return to its less compressed starting configuration thereby controllably urging fluid flow outwardly of reservoir 164 via the flow control means of the invention. As the fluid contained within the bellows reservoir 164 is urged outwardly thereof by the stored energy means, the fluid will flow into a fluid passageway 185 formed in the first portion 184a of ullage member 184. The fluid will then flow under pressure through a filter means shown here as a filter 116 that is identical to that previously described. After flowing through filter 116, the fluid will flow, via a stub passageway 185a (FIG. 52) into the several radially outwardly extending flow passageways 120 formed in flow control member 86. The filtered fluid will fill passageways 120 and then will flow into the plurality of spiral passageways 90 formed in member 86 via outlets 90b, which communicate with passageways 120 (see FIG. 10). The fluid contained within spiral passageways 90 can flow outwardly of the device only when one of the fluid outlets 84 formed in casing 82 is aligned with passageway 186 (FIG. 52).

Selection of the passageway 90 from which the fluid is to be dispensed is accomplished by rotation of the selector knob 88 in the manner previously described in connection with the embodiment shown in FIGS. 19 through 31. The construction and operation of the selector knob, the indexing means and the locking means is identical to that previously described and will not be re-described at this time.

As in the earlier described embodiments of the invention, as the fluid flows outwardly of the apparatus due to the urging of the stored energy means or elastomeric member 170, the bellows structure 162 will be collapsed and at the same time member 112 will travel inwardly of housing portion 256 and will provide an indication of the volume of fluid remaining in the fluid reservoir in the same manner as earlier described.

This latest embodiment also includes safety defeat disabling means, which, as shown in FIG. 43, is substantially identical in construction and operation to that previously described.

Considering next the alternate form of fill cartridge assembly 292, shown in FIGS. 61 and 62, this fill cartridge is similar in some respects to fill cartridge 262 and includes a vial 294 that is sealed at one end by a plunger 295 and at the other end by a pierceable septum 282. Formed intermediate the ends of vial 294 is a plurality of spaced-apart, angularly inclined fluid flow passageways 296 which permit fluid 266 to bypass a member or barrier stopper 297 as the barrier stopper is urged inwardly of the container by pressure exerted thereon by fluid 266. Fluid 266 exerts pressure on barrier member 297 as a result of pusher member 274 of the vial housing 270 exerting inward pressure on plunger 295, which pressure is, in turn, caused by the inward movement of plunger 295 as vial housing 270 is mated with the housing 252.

A continued inward pressure exerted on elastomeric plunger 295 will cause fluid 266 to flow past elastomeric barrier member 297 via flow passageway 296 so as to reconstitute lyophilized drug 264 (FIG. 61). Further pressure exerted on plunger 295 will cause the reconstituted drug formed by the fluid 266 which has been intermixed with drug 264 to flow through a hollow cannula 283 past check valve 284, into a stub passageway 286, then into a passageway 290 into the micro-channels 166a and, finally, into reservoir 164 (FIG. 52).

Figure 66:
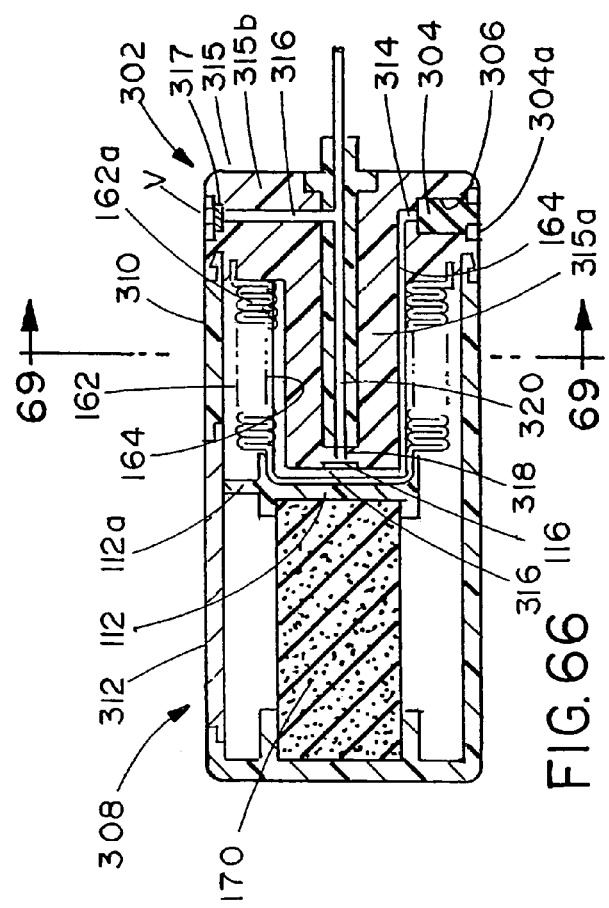
FIG. 66 is a longitudinal cross-sectional view of the embodiment of the invention shown in FIG. 64.

Referring now to FIGS. 64 through 70, yet another embodiment of the dispensing apparatus of the present invention is there illustrated and generally designated by the numeral 302. This alternate form of the apparatus of the invention is somewhat similar to that shown in the previous Figure drawings and like numerals are used in FIG. 64 through 70 to identify like components. The primary difference between this latest form of the invention and the invention shown in earlier Figure drawings resides in the fact that the only fill means comprises a septum 304 that is disposed within a cavity 306 in the device housing 308. Septum 304 is pierceable by the needle of a syringe which contains the medicinal fluid to be dispensed and used to fill the fluid reservoir of the device (FIG. 66).

Figure 68:
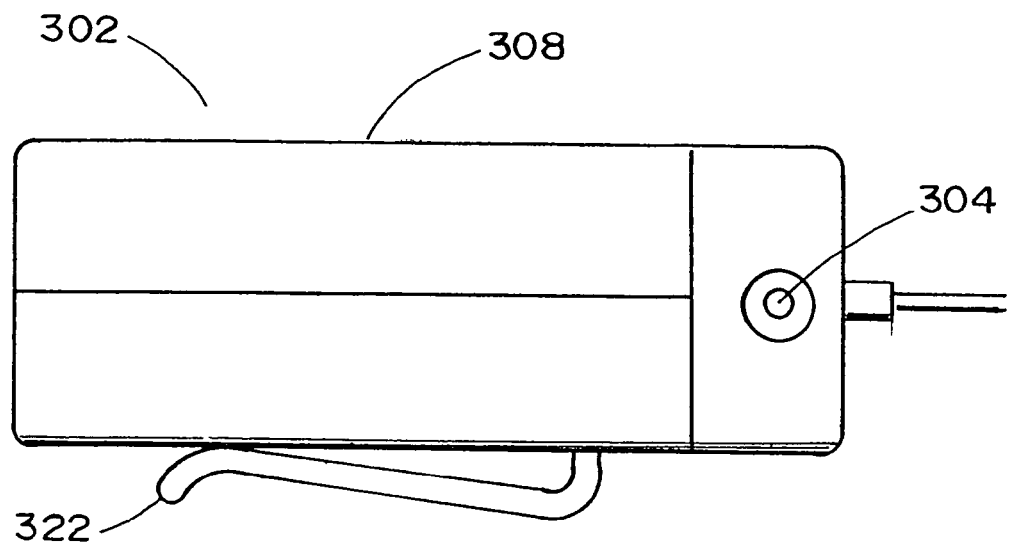
FIG. 68 is a bottom plan view of the apparatus of the invention.
Figure 69:
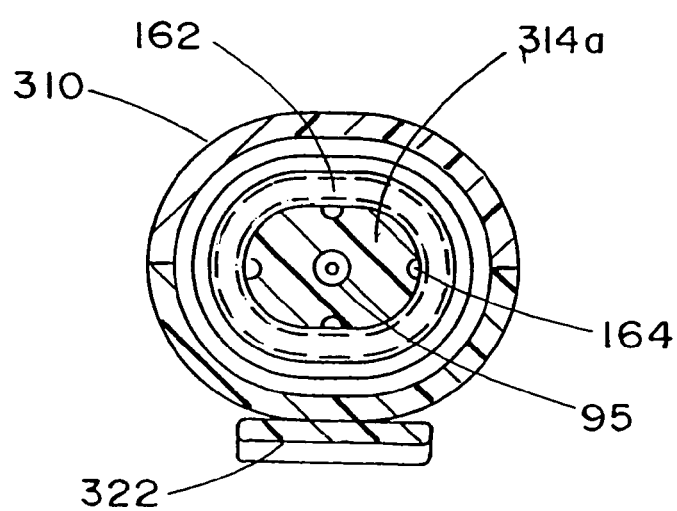
FIG. 69 is a cross-sectional view taken along lines 69-69 of FIG. 66.
Figure 70:
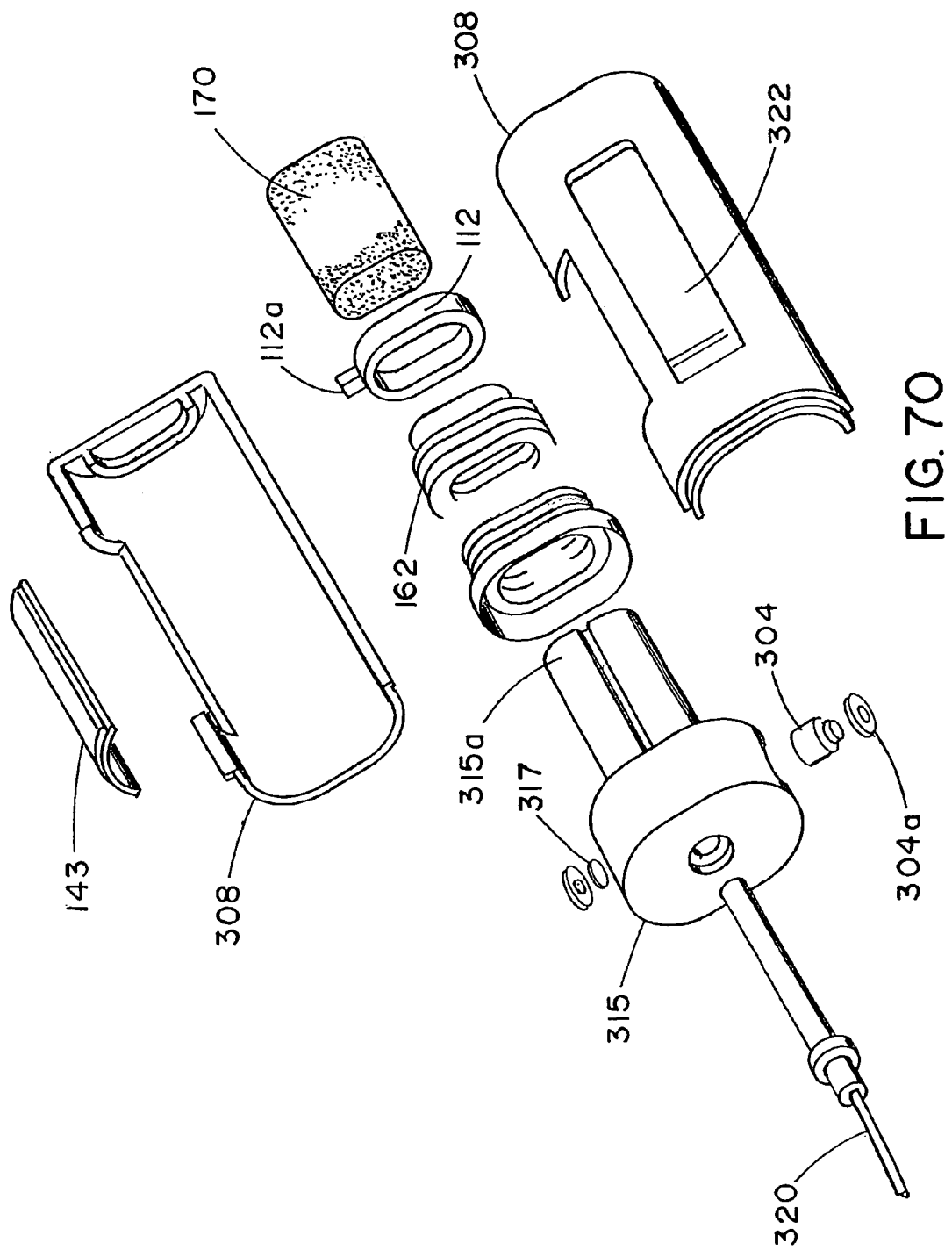
FIG. 70 is a generally perspective exploded view of the apparatus of this latest form of the invention.

As best seen in FIGS. 64 and 68, the outer housing 308 comprises first and second portions 310 and 312 respectively. Disposed within outer housing 308 is an inner, expandable housing 162 that is of identical construction and operation to the expandable housing of the earlier described embodiments of the invention. Housing 162 includes a fluid reservoir 164 that is provided with an inlet 314 (FIG. 66) for permitting fluid flow into the fluid reservoir. As before, expandable housing 162 comprises a bellows structure having an expandable and compressible, accordion like sidewall 162a of the character best seen in FIG. 66.

Disposed within second portion 312 of outer housing 308 is the stored energy means of the invention for acting upon inner expandable housing 162 in a manner to cause the fluid contained within fluid reservoir 164 to controllably flow through an outlet, the character of which will presently be described. Any gases contained within the expandable housing will be substantially vented to atmosphere through a vent "V" via a passageway 316 and a filter 317.

In this alternate form of the invention, the important stored energy means is identical in construction and operation to the earlier described stored energy means and here comprises a compressively deformable, elastomeric member 170 that is carried within the second portion 312 of the outer housing. As before, in operation, member 170 is first compressed by fluid flowing into reservoir 164 and then is controllably expanded to cause fluid flow from the fluid reservoir.

As previously mentioned, in the last described embodiment of the invention, the fill means which is carried by the second portion 312 of outer housing 308 for filling the reservoir 164 with the fluid to be dispensed comprises the septum 304. Septum 304 is pierceable by the needle of the syringe which contains the medicinal fluid that can be used to fill or partially fill reservoir 164 via passageway 314 formed in second portion 312 of the housing.

Turning once again to FIG. 64, also forming a part of the fluid dispensing apparatus of this latest form of the invention is dispensing means for dispensing fluid to the patient. This dispensing means is identical in construction and operation to the previously identified administration set 94 and is connected to the ullage defining means of the invention that comprises a part of the housing 308. This ullage means is provided in the form of an ullage defining member 315 that includes a first portion 315a that is disposed within inner expandable housing 162 and a second portion 315b having a passageway 316 that is in communication with fluid reservoir 164.

Upon opening the fluid delivery path to the administration set 94, the stored energy means, or member 170, will tend to return to its uncompressed starting configuration thereby controllably urging fluid flow outwardly of reservoir 164. As the fluid contained within the bellows reservoir 164 is urged outwardly thereof by the stored energy means, the fluid will flow under pressure through a filter means shown here as filter 116 that is identical to that previously described. After flowing through filter 116, the fluid will flow, via a stub passageway 318 (FIG. 66) and into a fluid passageway 320, which comprises a fine bore capillary line portion of the administration set 94. The capillary line portion can be of various diameters and lengths to thereby enable precise fluid flow rate control.

As in the earlier described embodiments of the invention, as the fluid flows outwardly of the apparatus due to the urging of the stored energy means or elastomeric member 170, the bellows structure 162 will be collapsed and at the same time a member 112 will travel inwardly of housing portion and will provide an indication of the volume of fluid remaining in the load reservoir in the same manner as earlier described.

This latest embodiment also uniquely includes fastening means for releasably fastening the device to the clothing of the patient, such as a shirt pocket or a belt. This fastening means is here provided in the form of a spring clip 322 that is affixed to one side of the housing 308.

Figure 71:
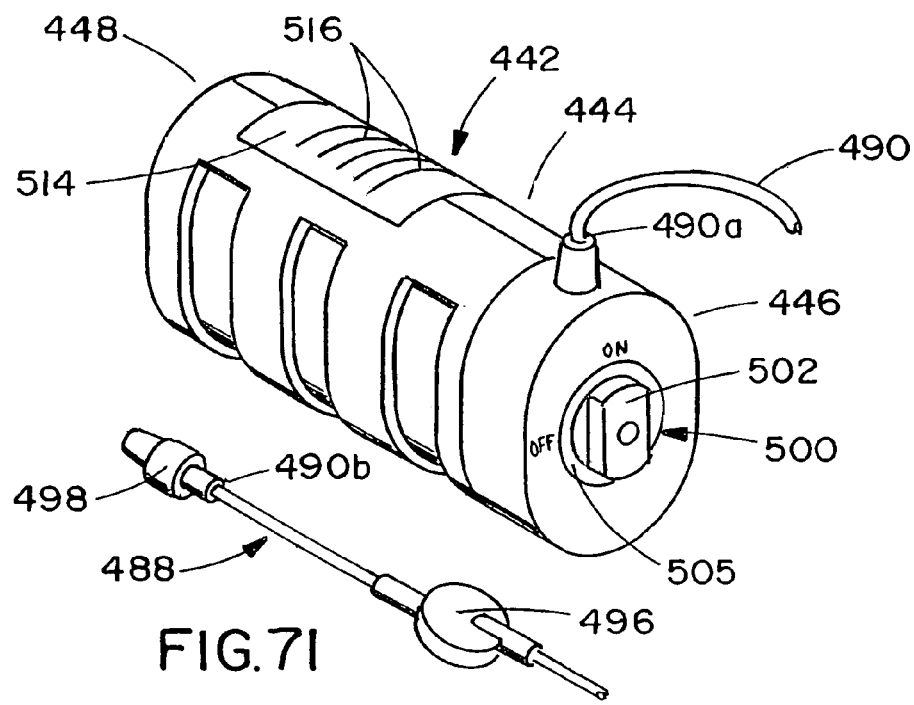
FIG. 71 is a generally perspective front view of yet another embodiment of the fluid delivery apparatus of the present invention for dispensing fluids at a uniform rate.
Figure 72:
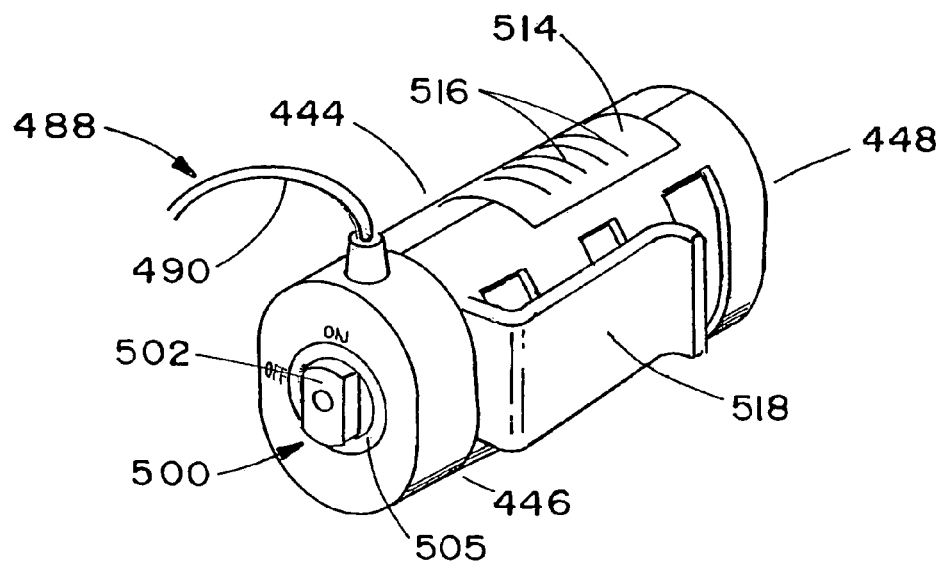
FIG. 72 is a generally perspective rear view of the embodiment shown in FIG. 71.
Figure 73:
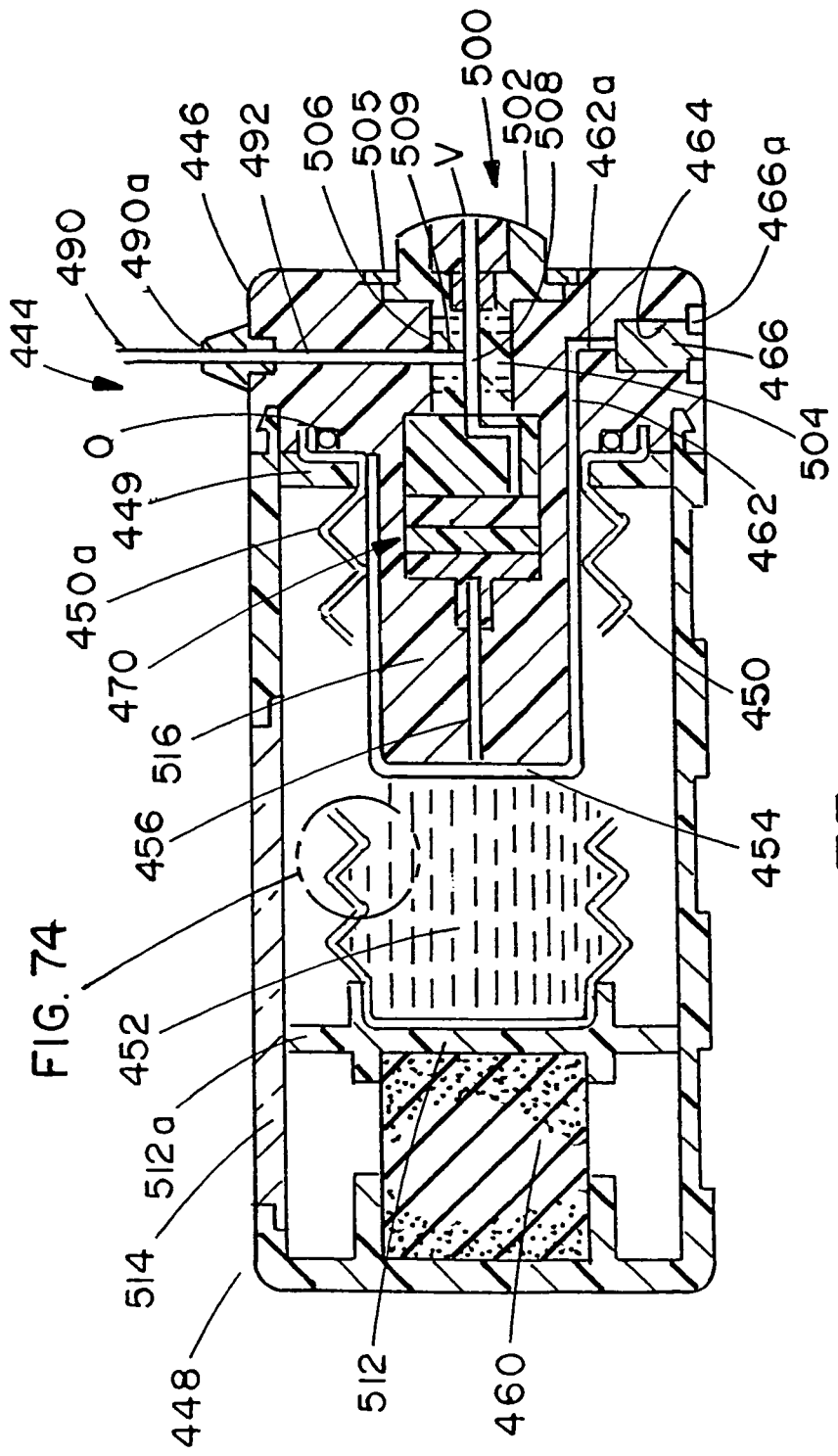
FIG. 73 is an enlarged longitudinal cross-sectional view of the apparatus shown in FIG. 71.
Figure 74:
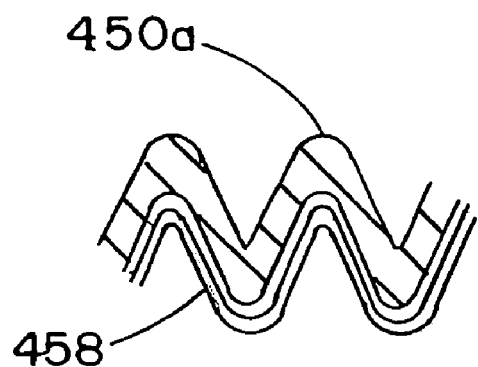
FIG. 74 is an enlarged cross-sectional view of the area designated as "74" in FIG. 73.

Referring next to FIGS. 71 through 85, yet another embodiment of the dispensing apparatus of the present invention is there illustrated and generally designated by the numeral 442. As best seen in FIGS. 71 and 72, the apparatus here comprises an outer housing 444 having first and second portions 446 and 448 respectively. Disposed within outer housing 444 is an inner, expandable housing 450 having a fluid reservoir 452 provided with an inlet 454 (FIG. 73) for permitting fluid flow into the fluid reservoir and an outlet 456 for permitting fluid flow from the fluid reservoir. Expandable housing 450, which can be constructed from a metal or plastic material, comprises a bellows structure having an expandable and compressible, accordion-like, annular-shaped sidewall 450a, the configuration of which is best seen in FIGS. 73 and 74. As best seen in FIG. 74, the inner wall of the bellows is provided, in the manner previously described herein, with one or more layers of a protective coating 458 that is compatible with the fluids contained within reservoir 452.

Disposed within second portion 448 of outer housing 444 is the novel stored energy means of the invention for acting upon inner expandable housing 450 in a manner to cause the fluid contained within fluid reservoir 452 to controllably flow outwardly of the housing. In the present form of the invention, this important stored energy means comprises a compressively deformable, elastomeric member 460 that is carried within the second portion 448 of the outer housing. In a manner presently to be described, member 460 is first compressed by fluid flowing into reservoir 452 and then is controllably expanded to cause fluid flow from the outer housing through the dispensing means of the invention. Stored energy member 460 can be constructed from a wide variety of materials including metals and plastics. By way of example, stored energy member 460 can be constructed from a wide variety of foam-like, solid and cellular materials including rubbers, molded or extruded plastics and other thermoplastic elastomers (TPE) and thermoplastic urethane (TPU) and polyethylene. By way of example, suitable materials include latex rubber, rubber polyolefins, polyisoprene (natural rubber), butyl rubber, nitrile rubber, polyurethane, vinyls, vinyl-end-blocked polydimethylsiloxanes, other homopolymer, copolymers (random alternating, block, graft, cross-link and star block), silicones and other flouropolymers, mechanical polyblends, polymer alloys and other thermoplastic elastomers (TPE) and thermoplastic urethane (TPU) and polyethylene.

Forming an important aspect of the apparatus of the present invention is fill means carried by outer housing 444 for filling the reservoir 452 with the fluid to be dispensed. As best seen in FIG. 73, first portion 446 includes a fluid passageway 462 in communication with inlet 454 of fluid reservoir 452. Proximate its lower end 462a, fluid passageway 462 communicates with a cavity 464 formed within portion 446 of the housing 444. Disposed within cavity 464 is a pierceable septum 466 that comprises a part of one form of the fill means of the invention. Septum 466 is held in position by a retainer 466a and is pierceable by the needle of the syringe which contains the medicinal fluid to be dispensed and which can be used in a conventional manner to fill or partially fill reservoir 452 via passageway 462.

Figure 81:
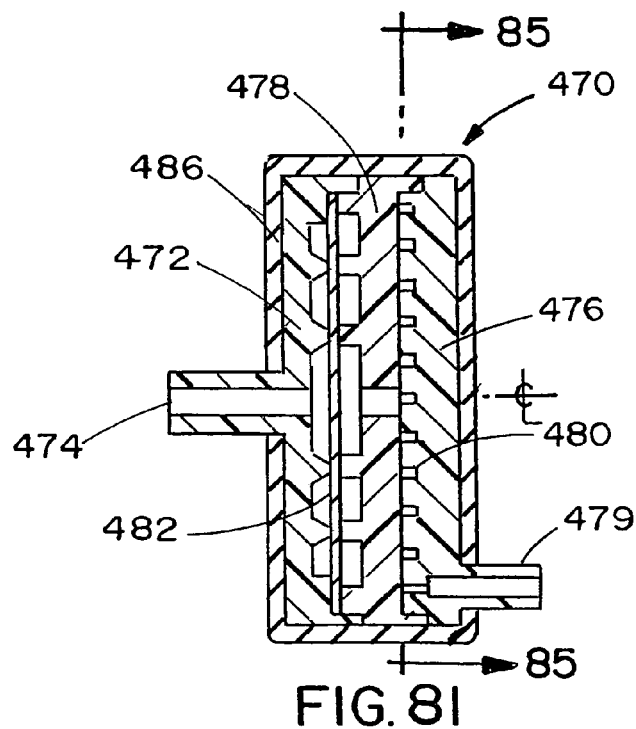
FIG. 81 is a greatly enlarged cross-sectional view of one form of the rate control assembly of the invention.
Figure 82:
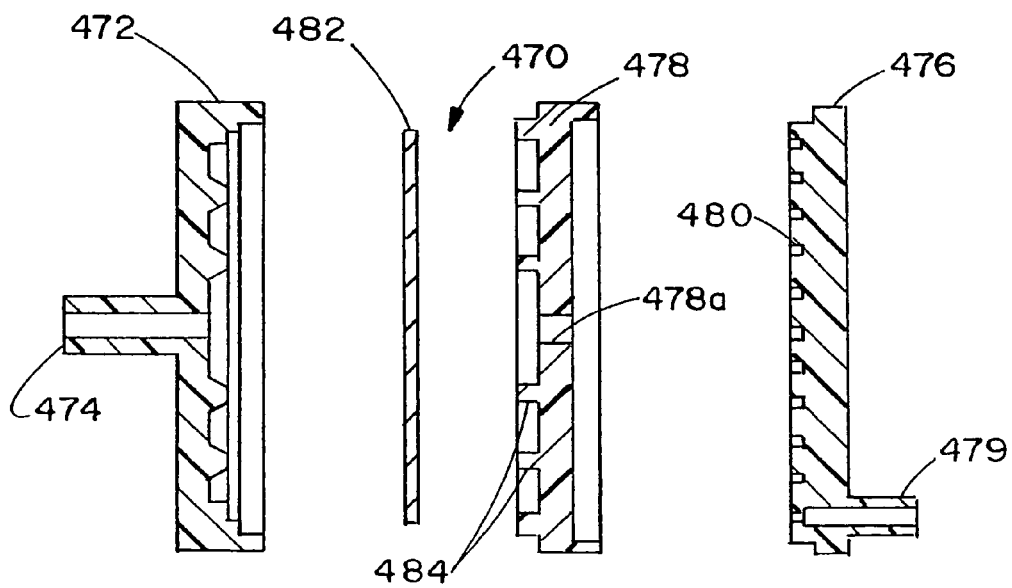
FIG. 82 is an exploded, cross-sectional view of the rate control assembly shown in FIG. 81.
Figure 86A:
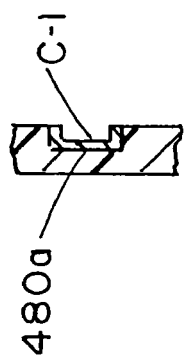
FIG. 86A is an enlarged cross-sectional view taken along lines 86A-86A of FIG. 86.
Figure 86:
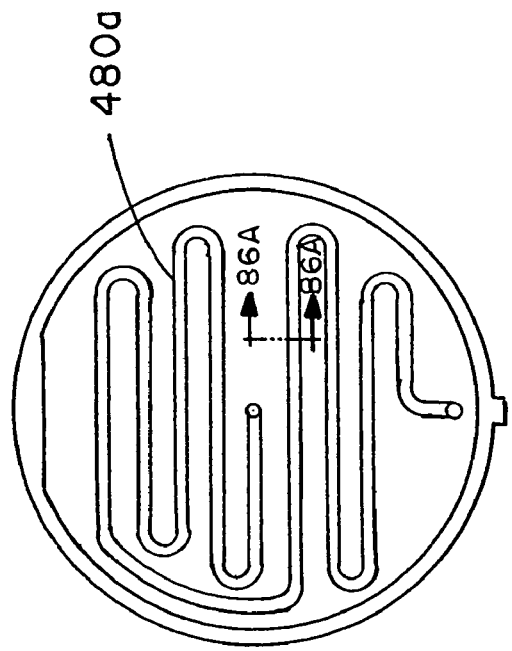
FIG. 86 is a view similar to FIG. 85, but showing an alternate form of the fluid flow control member of the rate control assembly of the invention.
Figure 85:
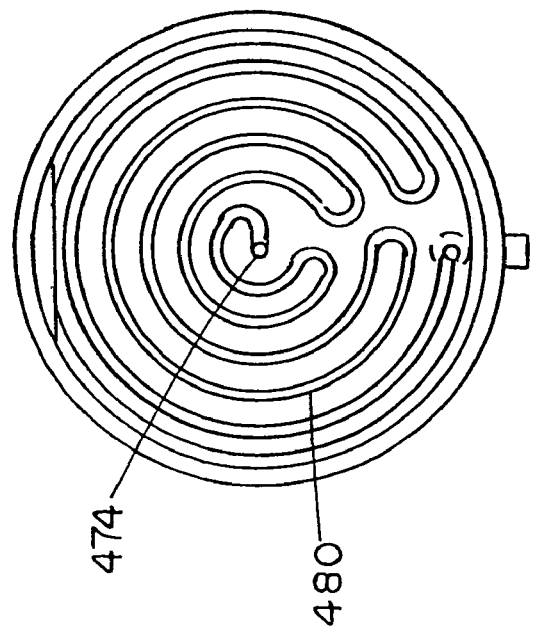
FIG. 85 is a cross-sectional view taken along lines 85-85 of FIG. 81.

Forming another very important aspect of the apparatus of the present invention is a novel flow control means that is disposed interiorly of outer housing 444. This flow control means functions to precisely control the outwardly rate of fluid flow from reservoir 452 and toward the patient. In the form of the invention shown in FIGS. 71 through 88 the flow control means comprises a flow control assembly generally designated in the drawings by the numeral 470. As best seen in FIGS. 81 and 82, this novel flow control assembly here comprises an inlet manifold 472 having an inlet port 474 that is in communication with the outlet 456 of the fluid reservoir 452 and an outlet manifold 476 that is interconnected with intake manifold 472 by means of a separator plate 478. As indicated in FIGS. 81 and 82, outlet manifold 476 as an outlet port 479 that is in communication with the outlet of the apparatus and is provided with an elongated micro-channel 480 that is coated with a coating C-1 (FIG. 86A) and is in communication both with inlet port 474 and with the outlet port 479 of the outlet manifold. Disposed intermediate inlet manifold 472 and a generally circular shaped separator plate 478 is filter means, here provided as a filter member 482 that functions to filter fluid flowing toward outlet port 479 of the outlet manifold. Generally disk shaped filter member 482 can be formed from various porous materials, including porous metals, plastics and porous ceramics.

As best seen in FIG. 82, separator plate 478 is provided with standoff ribs 484 for supporting filter member 482 in the manner shown in FIG. 81. The assemblage made up of inlet manifold 472, outlet manifold 476, separator plate 478 and filter 482 is preferably encapsulated within an outer metal or plastic casing 486 (see FIG. 81).

As indicated in FIG. 81, the flow rate control means, or assemblage 470, has an axial centerline "C" with which the inlet port 474 of the inlet manifold 472 is coaxial aligned. However, the outlet port 479 of the outlet manifold is radially spaced from the axial centerline. With this construction, fluid will flow from reservoir 452 into inlet port 474, through filter member 482, through a central opening 478a formed in separator plate 478 and thence into micro-channel 480 (see also FIG. 85). By controlling the length, depth and width of the micro-channel 480, the rate of fluid flow flowing outwardly of outlet 479 can be precisely controlled. In this regard, the micro-channel can take several forms as for example that illustrated in FIG. 86 of the drawings and generally designated therein by the numeral 480a. Where required for drug compatibility purposes, the micro channel 480a can be coated with a compatibility coating "C-1" of the character previously described. This coating can be accomplished in several ways, including the plasma coating process earlier described herein.

Turning once again to FIGS. 71, 72 and 73, also forming a part of the fluid dispensing apparatus of the present invention, is dispensing means for dispensing fluid to the patient. In the present form of the invention, this dispensing means comprises an administration set 488 that is connected to the first portion 446 of housing 444 in the manner shown in the drawings. The proximal end 490a of administration line 490 of the administration set 488 is in communication with an outlet fluid passageway 492 which is formed in housing portion 446 in the manner best seen in FIG. 73. Disposed between the proximal and 490a and the distal end 490b of the administration line is a conventional gas vent and filter 496. Provided at the distal end 490b of the administration line is a luer connector 498 of conventional construction (see FIG. 71).

Figure 75:
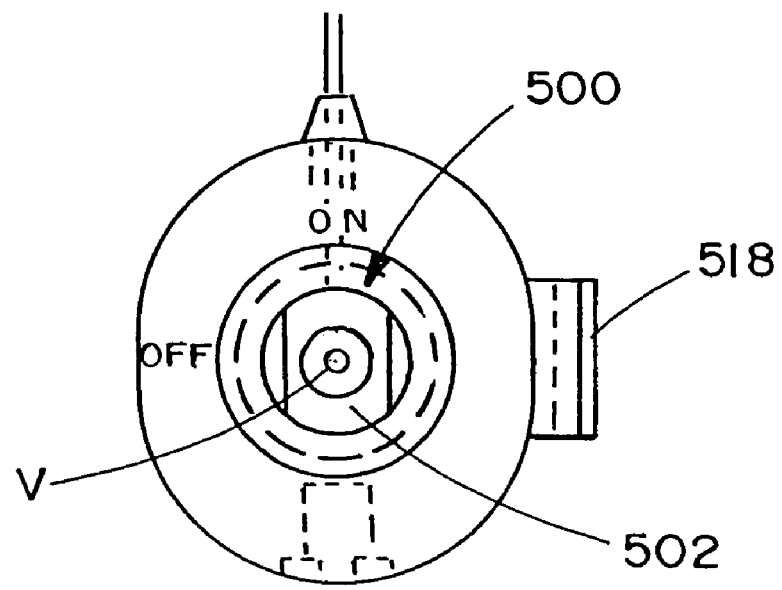
FIG. 75 is a right end view of the apparatus shown in FIG. 73.
Figure 76:
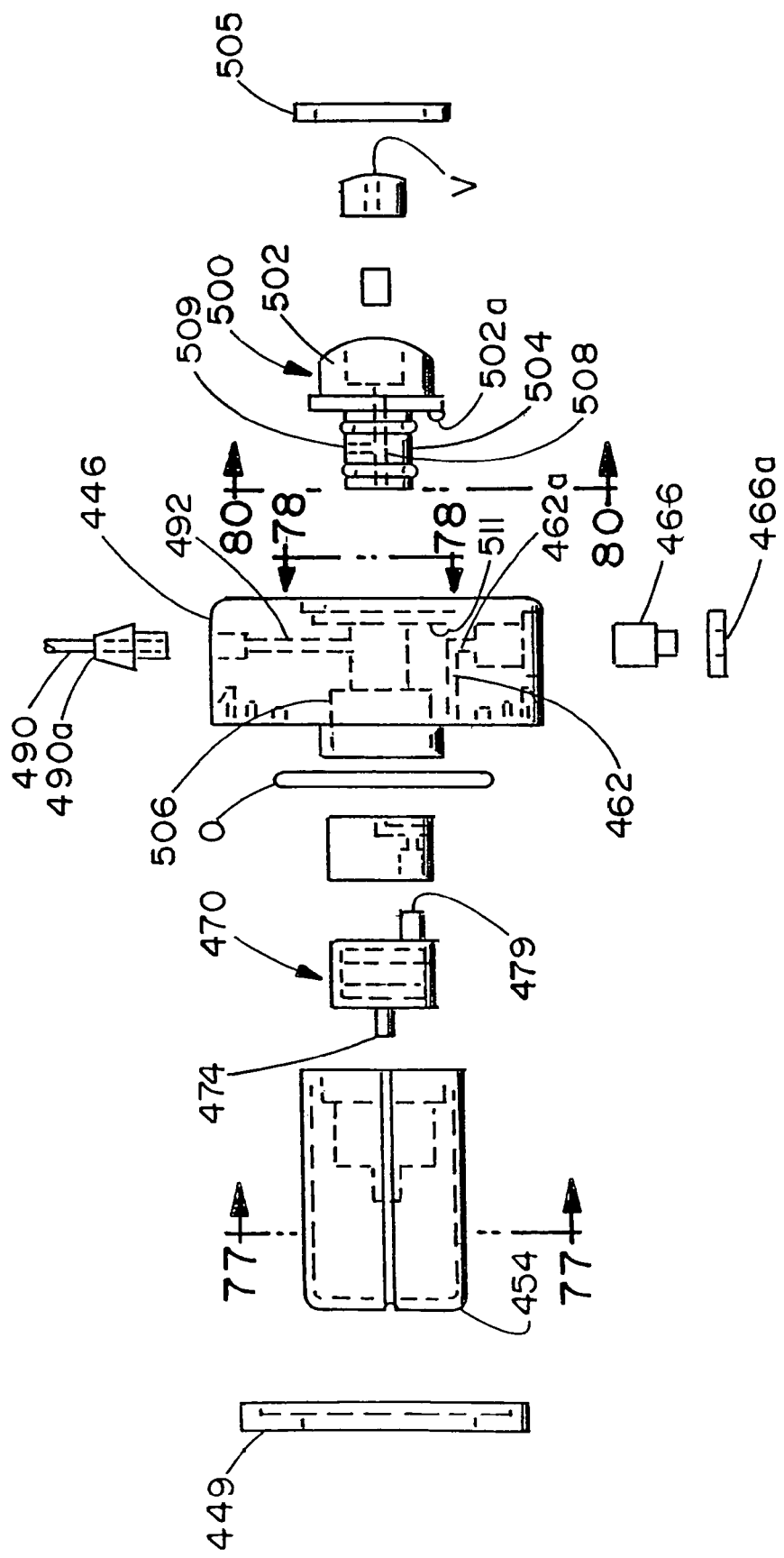
FIG. 76 is an exploded view of the forward section of the apparatus shown in FIG. 73.
Figure 77:
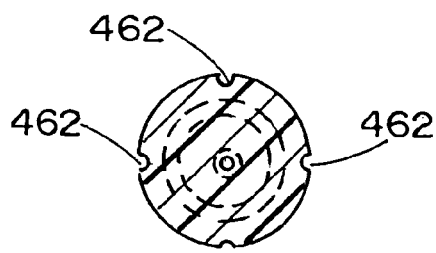
FIG. 77 is a cross-sectional view taken along lines 77-77 of FIG. 76.
Figure 78:
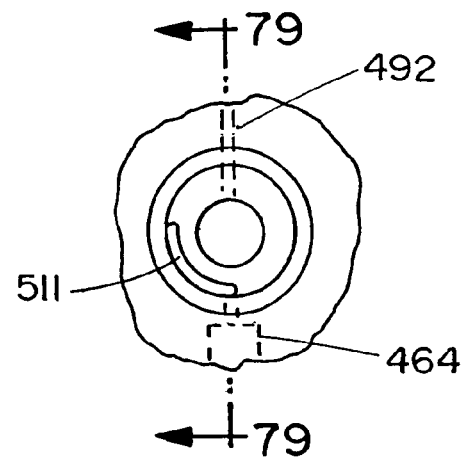
FIG. 78 is a view taken along lines 78-78 of FIG. 76.
Figure 79:
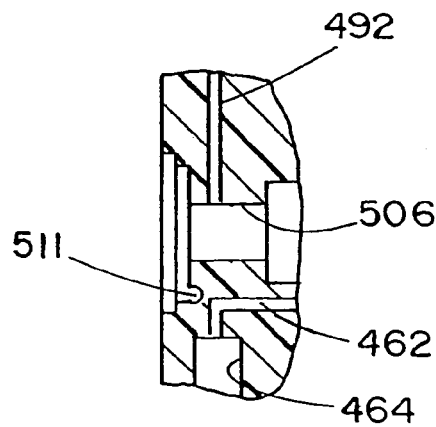
FIG. 79 is a cross-sectional view taken along lines 79-79 of FIG. 78.
Figure 80:
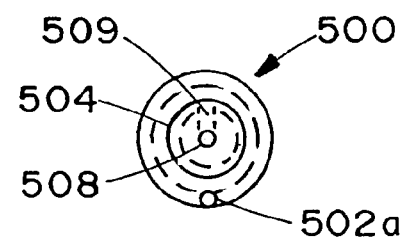
FIG. 80 is a view taken along lines 80-80 of FIG. 76.

To control fluid flow from the outlet 479 of the flow rate control means toward outlet passageway 492, novel operating means are provided. This operating means here comprises a control knob assembly 500 that includes a finger gripping portion of 502 and a generally cylindrically shaped shank portion 504 that is rotatably received within a bore 506 formed in housing portion 446 (FIG. 73). As indicated in FIG. 75, control knob assembly 500 is rotatable from a first "on", or fluid flow position, to a second "off" position as indicated by indicia provided on the forward face of housing portion 446. The control knob assembly is retained in position with a housing 446 by a retainer ring 505. Shank portion 504 of the control knob assembly includes an axial flow passageway 508 that communicates with the earlier identified outlet flow passageway 492 via a stub passageway 509. The flow passageway 508 also communicates with outlet 479 of flow rate control assembly 470 when the control assembly is in the "on" position shown in FIG. 75. In this position, fluid can flow from reservoir 452, through outlet 456, through flow rate control assembly 470, into central passageway 508 of the control knob assembly and then toward the administration set via passageway 492. As indicated in FIGS. 76 and 78, to guide the travel of the control knob assembly, the control knob assembly is provided with a protuberance 502a that travels within a groove 511 provided in the housing portion 446.

In using the apparatus of the invention, with the control knob assembly in the "off" position, the reservoir 452 of the bellows component 450 can be filled by filling means which comprises a conventional syringe having a needle adapted to pierce the pierceable septum 466 which is mounted within portion 446 of the apparatus housing. As the fluid flows into the bellows reservoir, the bellows will be expanded from a collapsed into an expanded configuration, such as is shown in FIG. 73. As the bellows member expands it will urge a telescopically movable volume indicator member 512 that is carried within a second portion 448 of the housing into engagement with the stored energy source causing it to compress. As the reservoir 452 fills with fluid from the filling syringe, any gases trapped within the reservoir will be vented to atmosphere via vent means "V" mounted in knob 502.

With the infusion apparatus interconnected with the patient's clothing by means of a spring clip assembly 518, which is affixed to the side of the device housing in the manner shown in FIGS. 72 and 75, and with the administration set 488 interconnected with the patient, opening the fluid delivery path to the administration set can be accomplished by rotating the control knob from the "off" position to the "on" position. Upon opening the fluid delivery path, the stored energy means, or member 460, will tend to return to its starting configuration thereby controllably urging fluid flow outwardly of reservoir 452 via the flow rate control means of the invention, passageway 508 of the control knob assembly and delivery passageway 492 formed in housing portion 446. As the fluid flows outwardly of the apparatus due to the urging of the stored energy means, the bellows structure 450 will be collapsed and at the same time member 512 will travel inwardly of housing portion 448. Member 512, which forms a part of the volume indicator means of the invention, includes a radially outwardly extending indicating finger 512*a* that is visible through a volume indicator window 514 that is provided in a second portion 448 of the apparatus housing and also comprises a part of the volume indicator means of the invention (FIGS. 71 and 72). Indicia 516, which are provided on indicator window 514, function to readily indicate to the caregiver the amount of fluid remaining within fluid reservoir 452.

As previously discussed, a number of beneficial agents can be introduced into reservoir 452 and can be controllably dispensed to the patient including, by way of example, medicaments of various types, drugs, pharmaceuticals, hormones, antibodies, biologically active materials, elements, chemical compounds, or any other suitable material useful in diagnostic cure, medication, treatment or preventing of diseases or the maintenance of the good health of the patient.

Referring next to FIG. 87, an alternate form of flow control means of the invention is there shown. This flow control means can be mounted within a modified housing 444 that will accommodate off-set, in-line input and output ports of the diameter shown in FIGS. 77 and 78. This latter flow control means functions to precisely control the rate of fluid flow from reservoir 452 toward the patient. In the form of the invention shown in FIG. 87, the flow control means comprises a flow control assembly generally designated in the drawings by the numeral 520. Flow control assembly 520 here comprises a first component or inlet manifold 522 having an inlet port 524 that can be placed in communication of the outlet 456 of the fluid reservoir 452 and an outlet manifold 526 that can be interconnected with first component 522 by means of a pair of separator plates or components 528 and 529. Outlet manifold component 526 has an outlet port 543 that is in communication with the outlet 542 of separator plate 529 and also in communication with the outlet of the apparatus. Intake manifold 522 has an inner surface 522*a* that is provided with a plurality of interconnected, imbedded capillaries 532. Capillaries 532 are in communication both with inlet port 524 and with an outlet port 534 formed in the inlet manifold. Disposed adjacent manifold 522 is separator plate 528. Separator plate 528 has an inner, uninterrupted surface 528*a* that is also provided with a plurality of imbedded capillaries 536 that are in communication with outlet port 534 formed in the inlet manifold. Fluid flowing from capillaries 532 flows into capillaries 536 via an inlet port 537 and then outwardly of separator plate 528 via an outlet port 536*a*.

Separator plate 529, which is disposed intermediate separator plate 528 and outlet manifold 526, has an inner, uninterrupted surface 529*a* that is provided with a plurality of interconnected capillaries 540 that receive the fluid flowing outwardly of outlet port 536*a*. After the fluid flow through capillaries 540, it will flow toward outlet 543 of outlet manifold 526 via an outlet port 542.

By controlling the length, width and depth of capillaries 532, 536, and 540, the rate of fluid flow flowing outwardly of outlet 543 can be precisely controlled. In this regard, it is to be understood that the capillaries of the flow control assembly can take several forms depending upon the end use of the fluid delivery device.

Turning now to FIG. 88, still another form of flow control means of the invention is there shown. This flow control means can also be mounted within housing 444 in place of flow control assembly 470 and functions to precisely control the rate of fluid flow from reservoir 452 and toward the patient. In the form of the invention shown in FIG. 88, the flow control means comprises a flow control assembly generally designated in the drawings by the numeral 550. Flow control assembly 550 here comprises a first component or inlet manifold 552 having an inlet port 554 that can be placed in communication with the outlet 456 of the fluid reservoir 452 and a second component or outlet manifold 556 that can be interconnected with intake manifold 552 by means of a separator component or plates 558 and 559. Outlet manifold 556 has an outlet port 557 that is in communication with the outlet 560 of separator plate 559 and also in communication with the outlet of the apparatus. Intake manifold 552 has an inner surface 552*a* that is provided with a plurality of interconnected imbedded capillaries 562. Capillaries 562 are in communication both with inlet port 554 and with an outlet port 564 formed in the inlet manifold. Disposed adjacent manifold 552 is a separator plate 558. Separator plate 558 has an inner surface 558*a* that is provided with a plurality of imbedded capillaries 566 that are in communication with outlet port 564 formed in the inlet manifold. Fluid flowing from capillaries 562 flows into capillaries 566 via an inlet port 569 and then outwardly of separator plate 558 via an outlet port 567.

Separator plate 559, which is disposed intermediate separator plate 558 and outlet manifold 556, has an inner surface 559*a* that is provided with a plurality of interconnected capillaries 570 that receive the fluid flowing outwardly of outlet port 567. After the fluid flows through capillaries 570, it will flow toward outlet 557 of outlet manifold 556 via an outlet port 560.

As before, by controlling the length, width and depth of capillaries 562, 566, and 570 the rate of fluid flow flowing outwardly of outlet 557 can be precisely controlled.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A dispensing apparatus for dispensing fluids to a patient comprising:
   (a) an outer housing having a first, second and third portions;
   (b) an inner, expandable housing disposed within said outer housing, said inner expandable housing having a fluid reservoir provided with an inlet for permitting fluid flow into said fluid reservoir;
   (c) stored energy means disposed within said second portion of said outer housing for acting upon said inner expandable housing to cause the fluid contained within said fluid reservoir to controllably flow outwardly toward the patient, said stored energy means comprising a compressively deformable, substantially continuous, semisolid member carried within said second portion of said outer housing, said semisolid member being expandable to cause fluid flow from said fluid reservoir;

(d) fill means carried by said outer housing for filling said reservoir with the fluid to be dispensed;
(e) flow control means connected to said first portion of said outer housing for controlling fluid flow from said reservoir, said flow control means comprising a flow control assembly including:
  (i) an ullage defining member having a first portion disposed within said inner, expandable housing and a second portion having a fluid passageway in communication with said outlet of said fluid reservoir;
  (ii) a fluid flow control member rotatably mounted within said first portion of said ullage defining member, said flow control member having an inlet passageway in communication with said fluid reservoir, a plurality of elongated fluid flow control channels, each of said plurality of elongated fluid flow control channels having an inlet and an outlet and distribution means formed in said flow control member for distributing fluid from said reservoir to each of said plurality of elongated flow control channels;
  (iii) an outer casing circumscribing said flow control member;
  (iv) filter means carried by said flow control member for filtering fluid flowing toward said distribution means;
  (v) selector means rotatably connected to said second portion of said ullage defining member for rotating said fluid flow control member to selectively align an outlet of one of said elongated fluid flow control channels with said fluid passageway in said second portion of said ullage defining member; and
  (vi) dispensing means for dispensing fluid to the patient, said dispensing means being connected to said second portion of said ullage defining member, and being in communication with said fluid passageway of said second portion of said ullage defining member; and
(f) volume indicator means carried by said outer housing for indicating the volume of fluid remaining in said fluid reservoir.

2. The apparatus as defined in claim 1 further including disabling means carried by said outer housing for preventing fluid flow toward said dispensing means.

3. The apparatus as defined in claim 1 in which said housing includes a cavity in communication with said inlet of said fluid reservoir and in which said fill means comprises a pierceable septum disposed within said cavity.

4. The apparatus as defined in claim 3 in which said fill means comprises a first fill vial receivable within said third portion of said outer housing.

5. The apparatus as defined in claim 4 in which said fill means comprises a second fill vial receivable within said third portion of said outer housing.

6. The apparatus as defined in claim 5 in which said third portion of said outer housing includes:
  (a) a fluid passageway in communication with said inlet of said fluid reservoir;
  (b) a first chamber for telescopically receiving said first fill vial;
  (c) an elongated support mounted within said first chamber, said elongated support having an elongated hollow needle, said hollow needle defining a flow passageway in communication with said fluid passageway;
  (d) a second chamber for telescopically receiving said second fill vial; and
  (e) an elongated support mounted within said second chamber, said elongated support having an elongated hollow needle, said hollow needle defining a flow passageway in communication with said fluid passageway.

7. The apparatus as defined in claim 6 in which each of said first and second fill vials has a first open end, a closed second end and each includes;
  (a) a fluid reservoir disposed between said first and second ends; and
  (b) a pierceable plunger disposed within said fluid reservoir for movement between first and second positions.

8. A dispensing apparatus for dispensing fluids to a patient comprising:
  (a) an outer housing having a first, second and third portions;
  (b) an inner, expandable housing disposed within said outer housing, said inner expandable housing having a fluid reservoir provided with an inlet for permitting fluid flow into said fluid reservoir;
  (c) stored energy means disposed within said second portion of said outer housing for acting upon said inner expandable housing to cause the fluid contained within said fluid reservoir to controllably flow outwardly toward the patient, said stored energy means comprising a compressively deformable, elastomeric member carried within said second portion of said outer housing said, said elastomeric member being expandable to cause fluid flow from said fluid reservoir;
  (d) fill means carried by said outer housing for filling said reservoir with the fluid to be dispensed;
  (e) flow control means connected to said first portion of said outer housing for controlling fluid flow from said reservoir, said flow control means comprising a flow control assembly including:
    (i) an ullage defining member having a first portion disposed within said inner, expandable housing and a second portion having a fluid passageway in communication with said outlet of said fluid reservoir;
    (ii) a flow control member rotatably mounted within said first portion of said ullage defining member, said flow control member having a plurality of elongated micro fluidic flow control channels, each of said plurality of elongated micro fluidic flow control channels having an inlet and an outlet;
    (iii) an outer casing circumscribing said flow control member;
    (iv) distribution means formed in said flow control member for distributing fluid from said fluid reservoir to each of said plurality of elongated micro fluidic flow control channels, said distribution means comprising a plurality of radially extending flow passageways formed in said flow control member;
    (v) selector means rotatably connected to said second portion of said ullage defining member for rotating said flow control member to selective align an outlet of one of said elongated flow control channels with said fluid passageway of said second portion of said ullage defining member, said selector means comprising a selector knob connected to said flow control member, said selector knob having finger gripping means for imparting rotation to said selector knob to align said outlet of a selected one of said elongated micro fluidic flow control channels with said outlet of said fluid passageway in said second portion of said ullage defining member;
    (vi) dispensing means for dispensing fluid to the patient, said dispensing means being connected to said second portion of said ullage defining member, and being in communication with said fluid passageway of said second portion of said ullage defining member; and (f) volume indicator means for indicating the volume of fluid remaining in said fluid reservoir.

9. The apparatus as defined in claim 8 further including disabling means carried by said outer housing for preventing fluid flow toward said dispensing means.

10. The apparatus as defined in claim 8 in which said outer housing includes a cavity in communication with said inlet of said fluid reservoir and in which said fill means comprises a pierceable septum disposed within said cavity.

11. The apparatus as defined in claim 8 further including locking means carried by said outer housing for blocking rotation of said selector knob.

12. The apparatus as defined in claim 8 in which said fill means comprises a cartridge fill vial receivable within said third portion of said outer housing.

13. The apparatus as defined in claim 12 in which said third portion of said outer housing includes;

(a) a removable vial cover;
(b) a fluid passageway in communication with said inlet of said fluid reservoir;
(c) a chamber for telescopically receiving said cartridge fill vial; and
(d) an elongated support mounted within said removable vial cover.

14. The apparatus as defined in claim 13 in which said cartridge fill vial has first and second ends and includes:

(a) a pierceable septum closing one of said first and second ends;
(b) a fluid reservoir disposed between said first and second ends; and
(c) a plunger disposed within said fluid reservoir for movement between first and second positions.

\* \* \* \* \*